United States Patent [19]

Mori et al.

[11] Patent Number: 5,250,219
[45] Date of Patent: Oct. 5, 1993

[54] MESOMORPHIC COMPOUND, LIQUID CRYSTAL COMPOSITION CONTAINING SAME AND LIQUID CRYSTAL DEVICE USING SAME

[75] Inventors: Shosei Mori, Atsugi; Takao Takiguchi, Tokyo; Takashi Iwaki, Isehara; Yoko Yamada, Atsugi; Takeshi Togano, Yokohama; Masataka Yamashita, Hiratsuka; Masahiro Terada, Atsugi; Kazuharu Katagiri, Tama, all of Japan

[73] Assignee: Canon Kabushiki Kaisha, Tokyo, Japan

[21] Appl. No.: 863,325

[22] Filed: Apr. 2, 1992

Related U.S. Application Data

[63] Continuation of Ser. No. 518,941, May 4, 1990, abandoned.

[30] Foreign Application Priority Data

May 8, 1989 [JP] Japan ................ 1-115682
Jan. 26, 1990 [JP] Japan ................ 2-16557

[51] Int. Cl.$^5$ ............ C09K 19/34; C09K 19/30; C09K 19/52; G02F 1/13
[52] U.S. Cl. ............ 252/299.61; 252/299.01; 252/299.62; 252/299.63; 252/299.64; 252/299.65; 252/299.66; 252/299.67; 259/103; 259/104
[58] Field of Search ............ 252/299.01, 299.5, 299.6, 252/299.61, 299.62, 299.63 299.64, 299.65, 299.66, 299.67; 359/103, 104

[56] References Cited

U.S. PATENT DOCUMENTS

| 4,367,924 | 1/1983 | Clark et al. ............ 350/334 |
| 4,721,367 | 1/1988 | Yoshinaga et al. ............ 350/350 |
| 4,728,458 | 3/1988 | Higuchi et al. ............ 252/299.65 |
| 4,775,223 | 10/1988 | Yoshinaga et al. ............ 350/333 |
| 4,798,680 | 1/1989 | Nohira et al. ............ 252/299 |
| 4,812,259 | 3/1989 | Yoshinaga et al. ............ 252/299 |
| 4,816,178 | 3/1989 | Katagiri et al. ............ 252/299 |
| 4,820,839 | 4/1989 | Krause et al. ............ 544/316 |
| 4,873,018 | 10/1989 | Nohira et al. ............ 252/299 |
| 4,876,027 | 10/1989 | Yoshinaga et al. ............ 252/299 |
| 4,880,560 | 11/1989 | Yoshinaga et al. ............ 252/299 |
| 4,882,085 | 11/1989 | Yoshinaga et al. ............ 252/299 |
| 4,904,410 | 2/1990 | Nohira et al. ............ 252/299 |
| 4,917,817 | 4/1990 | Nohira et al. ............ 252/299 |
| 4,917,821 | 4/1990 | Mori et al. ............ 252/299 |
| 4,918,213 | 4/1990 | Nohira et al. ............ 558/271 |

FOREIGN PATENT DOCUMENTS

| 0268198 | 11/1987 | European Pat. Off. . |
| 0293910 | 6/1988 | European Pat. Off. . |
| 0307880 | 9/1988 | European Pat. Off. . |
| 0308794 | 9/1988 | European Pat. Off. . |
| 3518734 | 5/1985 | Fed. Rep. of Germany . |
| 0095892 | 12/1971 | German Democratic Rep. . |
| 107216 | 8/1981 | Japan . |
| 193426 | 11/1984 | Japan . |
| 193427 | 11/1984 | Japan . |
| 156046 | 8/1985 | Japan . |
| 156047 | 8/1985 | Japan . |
| 5434 | 2/1987 | Japan . |
| 22042 | 1/1988 | Japan . |
| 122651 | 5/1988 | Japan . |
| 04060 | 7/1986 | PCT Int'l Appl. . |
| 87/105012 | 8/1987 | World Int. Prop. O. . |

OTHER PUBLICATIONS

Applied Phys. Letters, vol. 18, No. 4 (Feb. 1971) pp. 127–128.

*Primary Examiner*—Robert L. Stoll
*Assistant Examiner*—Shean C. Wu
*Attorney, Agent, or Firm*—Fitzpatrick, Cella, Harper & Scinto

[57] ABSTRACT

A mesomorphic compound represented by the following formula (I):

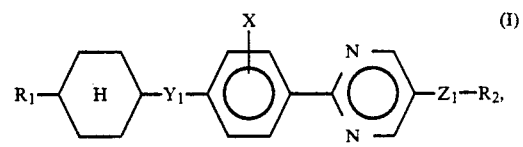

wherein $R_1$ and $R_2$ respectively denote a linear or branched alkyl group having 1-16 carbon atoms capable of having a substituent; $Y_1$ denotes —COO—, —OCO—, —CH$_2$O— or —OCH$_2$—; $Z_1$ denotes a single bond, —O—, —COO—, —OCO— or —OCOO—; and X denotes a halogen, cyano group for methyl group.

30 Claims, 2 Drawing Sheets

MESOMORPHIC COMPOUND, LIQUID CRYSTAL COMPOSITION CONTAINING SAME AND LIQUID CRYSTAL DEVICE USING SAME

This application is a continuation of application Ser. No. 518,941, filed May 4, 1990, now abandoned.

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and are vertically oriented with respect to the electrode surface only when an electric field is effectively applied) is driven (i.e. repeatedly scanned) by using a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density with respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4367924, instance, as the liquid crystals having bistability, ferroelectric liquid crystals having chiral smectic C-phase (SmC*) or H-phase (SmH*) are generally used. These liquid crystals have bistable states of first and second optically stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric field and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps.E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity η or increase the spontaneous polarization Ps.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°-40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

SUMMARY OF THE INVENTION

An object of the present invention is to provide a mesomorphic compound, a liquid crystal composition, particularly a ferroelectric chiral smectic liquid crystal composition, containing the mesomorphic compound for providing a practical ferroelectric liquid crystal device, and a liquid crystal device using the liquid crystal composition and having a high response speed and a smaller temperature-dependence of the response speed.

According to the present invention, there is provided a mesomorphic compound represented by the formula (I)

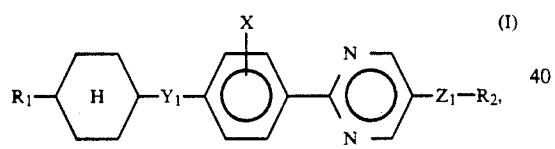

wherein $R_1$ and $R_2$ respectively denote a linear or branched alkyl group having 1-16 carbon atoms capable of having a substituent; $Y_1$ denotes —COO—, —OCO—, —CH$_2$O— or —OCH$_2$—; $Z_1$ denotes a single bond, —O—, —COO—, —OCO— or —OCOO—; and X denotes a halogen, cyano group or methyl group.

According to the present invention, there is also provided a liquid crystal composition, comprising: at least one mesomorphic compound represented by the above formula (I); and optionally at least one of the mesomorphic compounds represented by the following formula (II) and/or formula (III):

Formula (II):

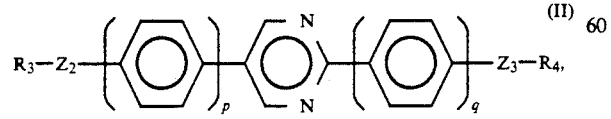

wherein $R_3$ and $R_4$ respectively denote a linearn or branched optically inactive alkyl group having 1-18 carbon atoms capable of having $C_1$-$D_{12}$ alkoxy group; $Z_2$ and $Z_3$ respectively denote a single bond, —O—, —OCO—, —COO— or —OCOO—; and p and q are respectively 0, 1 or 2;

Formula (III):

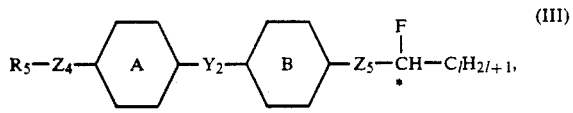

wherein $R_5$ denotes a linear or branched alkyl group having 1-18 carbon atoms capable of having a substituent; $Y_2$ denotes a single bond, —COO—, —OCO—, —COS—, —SCO—, —CH$_2$O—, —OCH$_2$— or —CH=CH—COO—; $Z_4$ denotes a single bond, —O—, —COO— or —OCO—; $Z_5$ denotes —OCH$_2$—, —COOCH$_2$—, —OCO— or —O(CH$_2$)$_x$O—CH$_2$—;

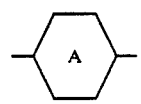

denotes

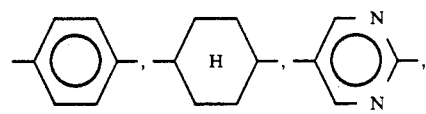

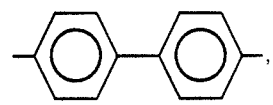

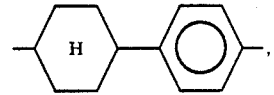

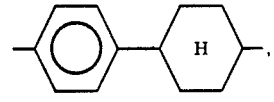

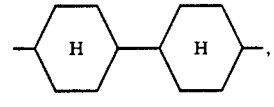

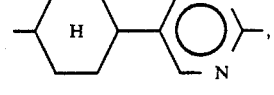

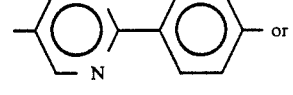

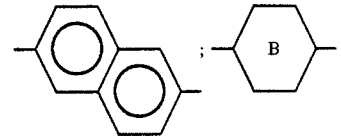

denotes

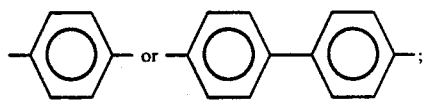

$l$ is 1–12 and $k$ is 1–4.

The present invention further provides liquid crystal devices comprising a pair of substrates and any one of the liquid crystal compositions as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
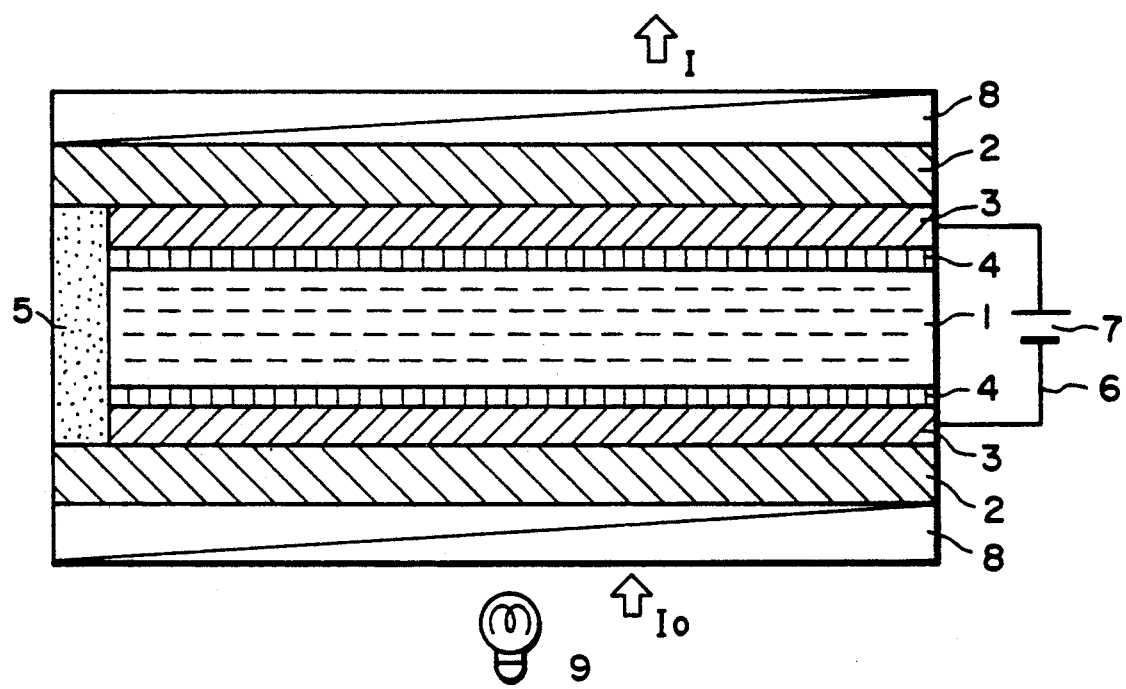
FIG. 1 is a schematic sectional view of a liquid crystal display device using a ferroelectric liquid crystal.

Preferred examples of the compounds represented by the above-mentioned general formula (I) may include those represented by the following formulas (I-a) and (I-b):

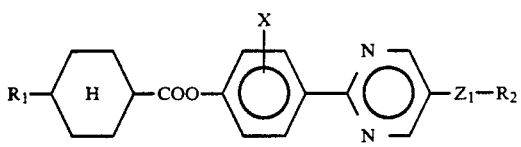

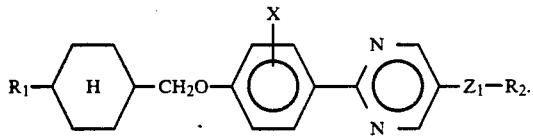

In the above formulas (I-a) and (I-b), $R_1$, $R_2$, X and $Z_1$ are the same as in the general formula (I). A particularly preferred class of compounds among the compounds represented by the-above formulas (I-a) and (I-b) may include those represented by the following formula (I-c):

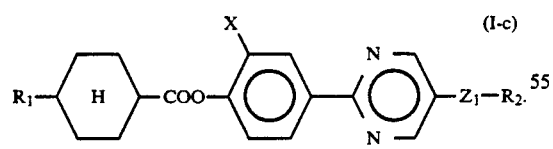

In the above-mentioned formula (I), $R_1$ may preferably be a group of (i) below and $R_2$ may preferably be a group selected from the following groups (i) to (iv).

(i) n-alkyl group having 1–16 carbon atoms;
(ii)

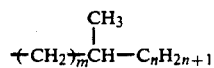

wherein m is 1–7 and n is 2–9 with proviso that $3 \leq m+n \leq 14$ (optically active or inactive);
(iii)

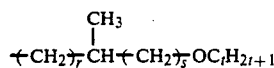

wherein r is 0–7, s is 0 or 1 and t is 1–14 with proviso that $1 \leq r+s+t \leq 14$ (optically active or inactive); and
(iv)

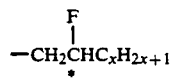

wherein x is 1–14. Herein * denotes an optically active center.

Further, in the above-mentioned formula (I), preferred examples of X may include halogens such as fluorine, chlorine and bromine, among which fluorine is particularly preferred.

Still further, in the above-mentioned formula (I), preferred examples of $Z_1$ may include a single bond, —O—, —COO— and —OCO—, among which a single bond or —O— is particularly preferred.

Preferred examples of the compounds represented by the above-mentioned formula (II) may include those represented by the following formulas (II-a) to (II-e):

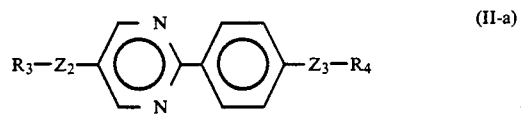

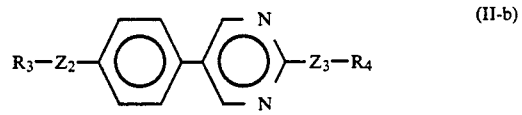

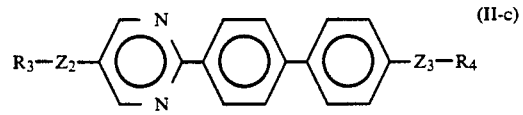

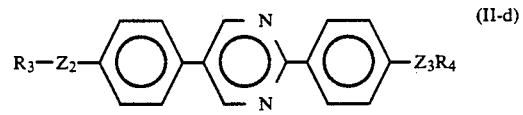

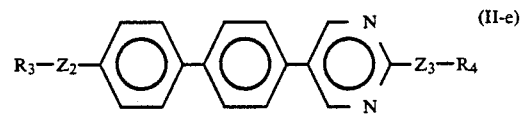

In the above formulas (II-a) to (II-e), $R_3$, $R_4$, $Z_2$ and $Z_3$ are the same as in the general formula (II). Preferred examples of $Z_2$ and $Z_3$ may include those of the following combinations (II-i) to (II-viii):

(II-i) $Z_2$ is a single bond and $Z_3$ is a single bond,
(II-ii) $Z_2$ is a single bond and $Z_3$ is —O—,
(II-iii) $Z_2$ is a single bond and $Z_3$ is —OCO—,
(II-iv) $Z_2$ is a single bond and $Z_3$ is —COO—,
(II-v) $Z_2$ is —O— and $Z_3$ is a single bond,
(II-vi) $Z_2$ is —O— and $Z_3$ is —O—,
(II-vii) $Z_2$ is —O— and $Z_3$ is —OCO—, and
(II-Viii) $Z_2$ is —O— and $Z_3$ is —COO—.

Further, in the above formulas (II-a) to (II-e), each of $R_3$ and $R_4$ may preferably be a linear or branched alkyl group having 4–14 carbon atoms capable of having a $C_1$-$C_{12}$ alkyl substituent. Particularly preferred examples of $R_3$ and $R_4$ may include those of the following combinations (II-ix) to (II-xi):

wherein y is 0–7, u is 0 or 1, and $R_6$ denotes a linear or branched alkyl group.

Preferred examples of the compounds represented by the above-mentioned general formula (III) may include those represented by the following formulas (III-a) to (III-f):

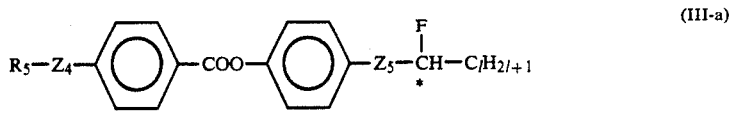 (III-a)

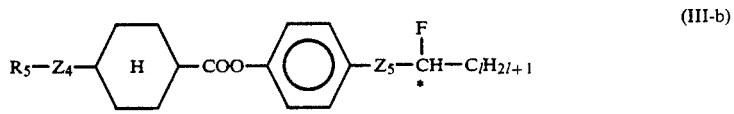 (III-b)

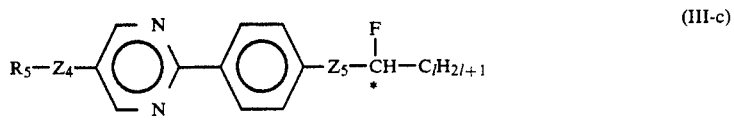 (III-c)

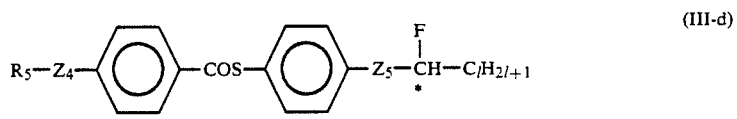 (III-d)

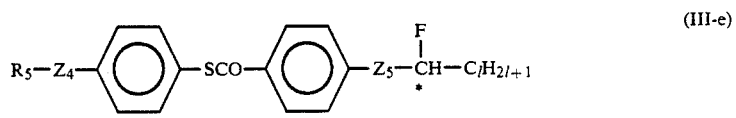 (III-e)

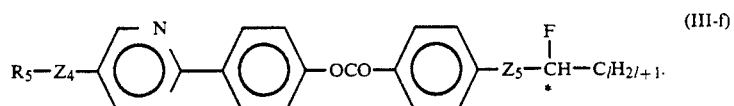 (III-f)

(II-ix) $R_3$ is an n-alkyl group having 4–14 carbon atoms and $R_4$ is an n-alkyl group having 4–14 carbon atoms, (II-x) $R_3$ is an n-alkyl group having 4–14 carbon atoms and $R_4$ is $$\text{---}(CH_2)_u\text{---}\underset{|}{\overset{CH_3}{CH}}\text{---}R_6,$$

wherein u is 0–7 and $R_6$ denotes a linear or branched alkyl group, (II-xi) $R_3$ is an n-alkyl group and $R_4$ is $$\text{---}(CH_2)_y\text{---}\underset{|}{\overset{CH_3}{CH}}\text{---}(CH_2)_u\text{---}OR_6$$

In the above formulas (III-a) to (III-f), $R_5$, $Z_4$, $Z_5$ and l are the same as in the general formula (III). Particularly preferred compounds among the compounds represented by the above formulas (III-a) to (III-f) may include those represented by the formulas (III-a) to (III-c).

Further, in the above formulas (III-a) to (III-f), preferred examples of $Z_4$ and $Z_5$ may include those of the following combinations (III-i) to (III-v):

(III-i) $Z_4$ is a single bond and $Z_5$ is —OCH$_2$—,
(III-ii) $Z_4$ is a single bond and $Z_5$ is —COOCH$_2$—,
(III-iii) $Z_4$ is a single bond and $Z_5$ is —OCO—,
(III-iv) $Z_4$ is —O— and $Z_5$ is —OCH$_2$—,
(III-v) $Z_4$ is —O— and $Z_5$ is —COOCH$_2$—.

Representative reaction schemes for producing the mesomorphic compounds represented by the above formula (I) are shown below.

(Case where $Y_1$ is —COO— or —CH$_2$O—)

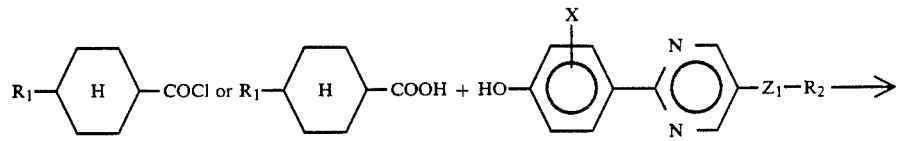

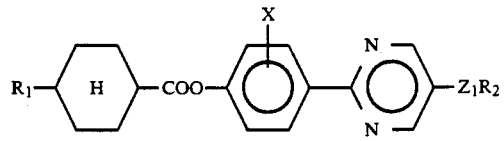
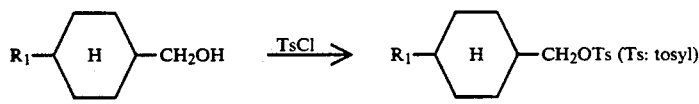
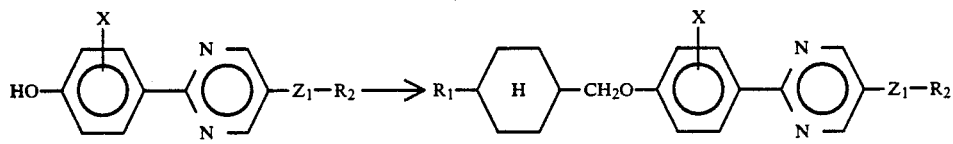
(Case where $Y_1$ is —OCO— or —OCH$_2$—)
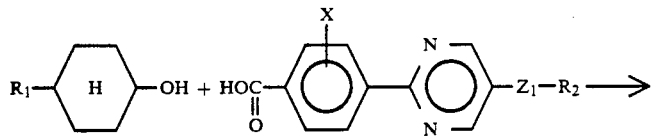
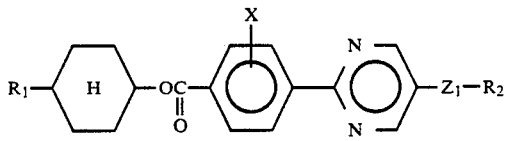
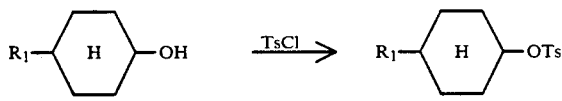
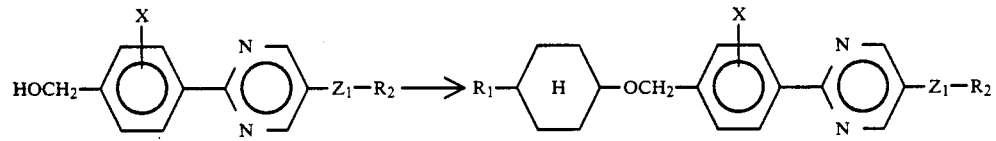
Specific examples of the mesomorphic compounds represented by the above-mentioned general formula (I) may include those shown by the following structural formulas.
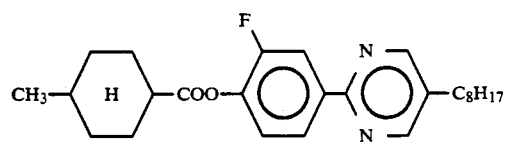
1-1
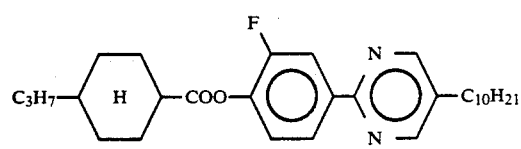
1-2

-continued
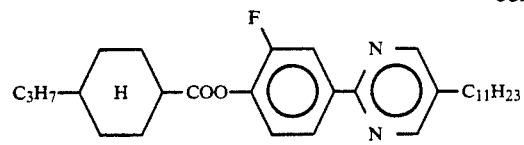
1-3
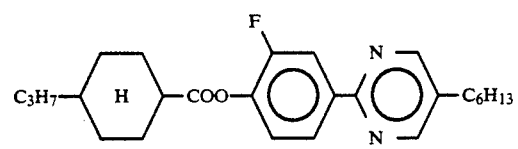
1-4
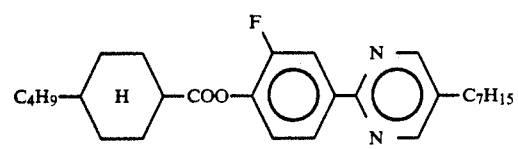
1-5
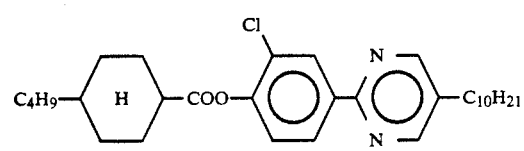
1-6
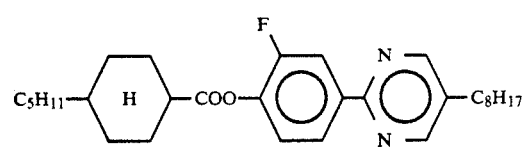
1-7
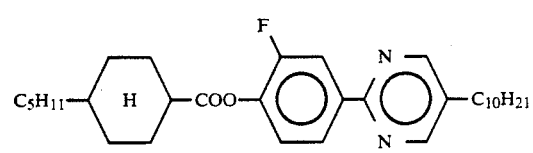
1-8
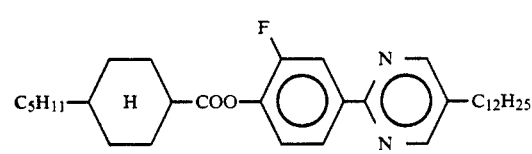
1-9
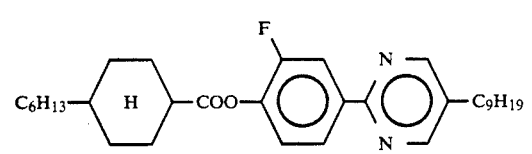
1-10
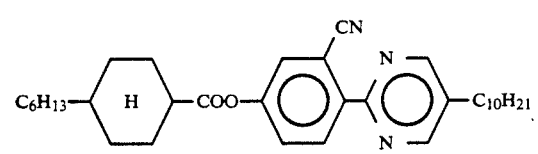
1-11
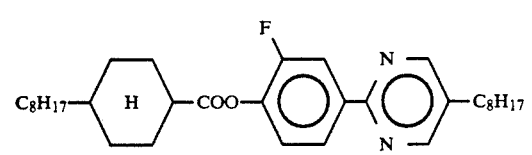
1-12
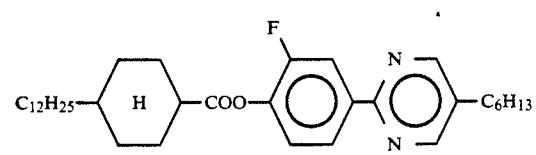
1-13

-continued
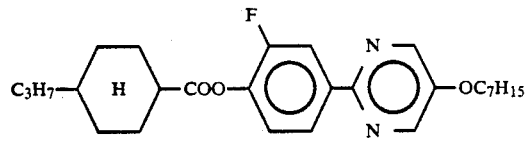
1-14
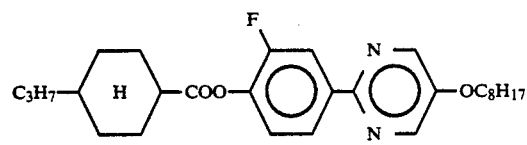
1-15
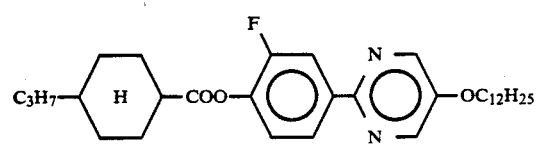
1-16
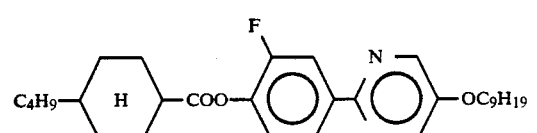
1-17
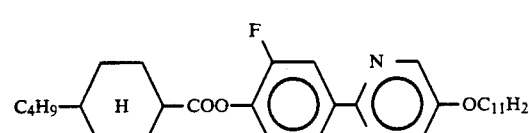
1-18
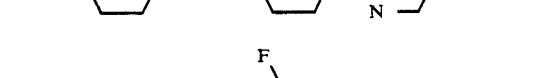
1-19
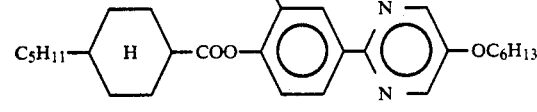
1-20
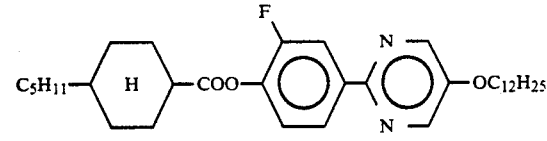
1-21
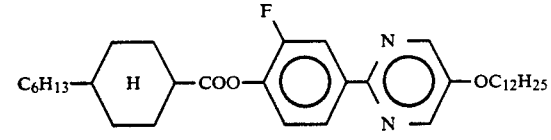
1-22
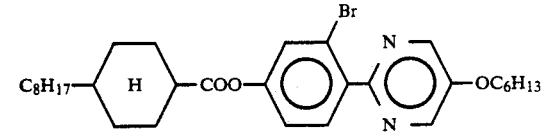
1-23
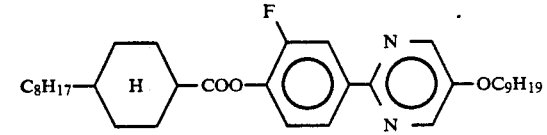
1-24
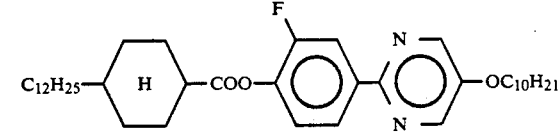

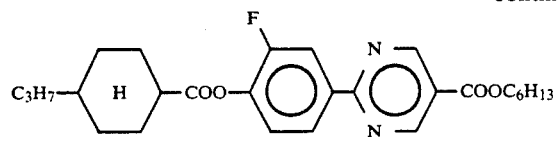
1-25
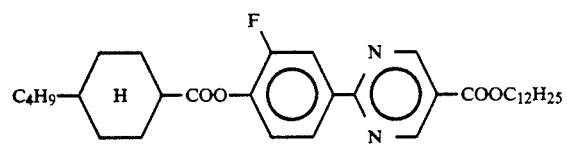
1-26
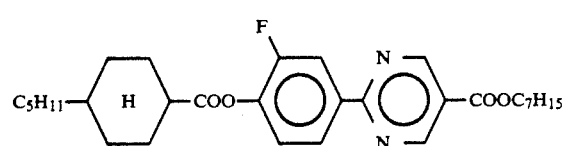
1-27
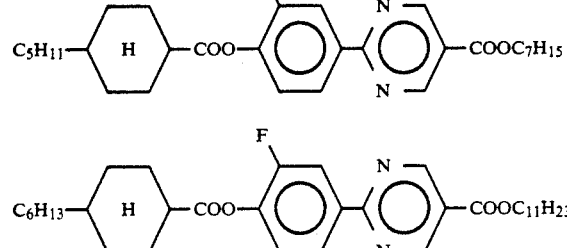
1-28
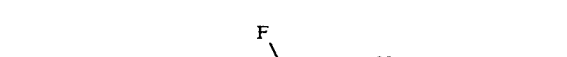
1-29
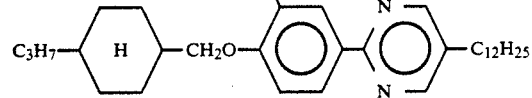
1-30
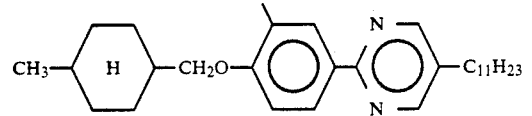
1-31
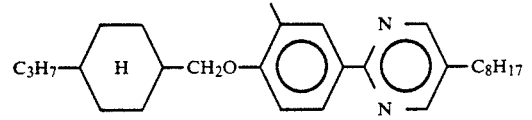
1-32
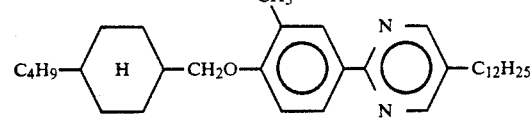
1-33
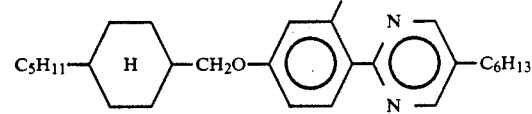
1-34
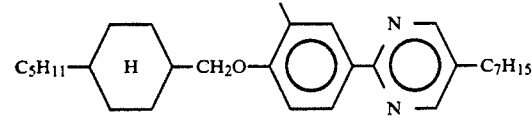
1-35
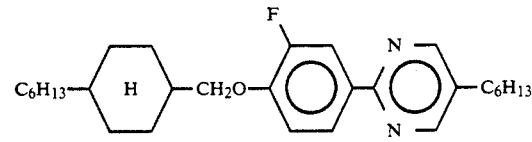

-continued
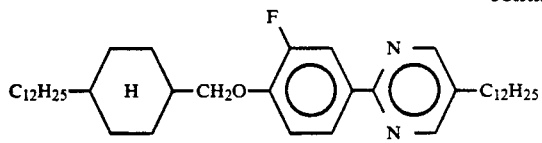 1-36
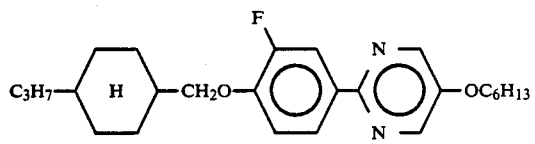 1-37
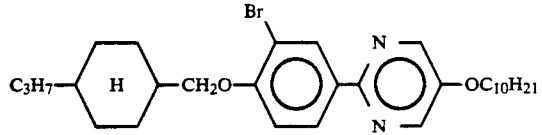 1-38
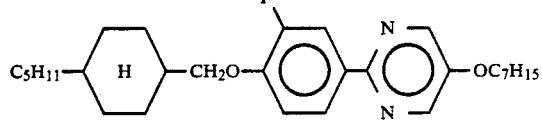 1-39
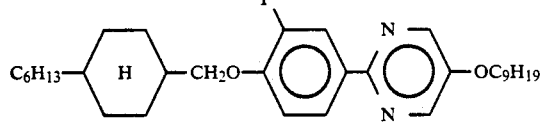 1-40
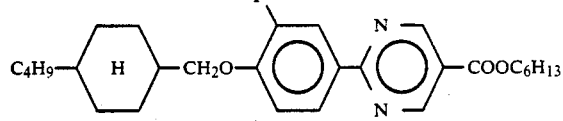 1-41
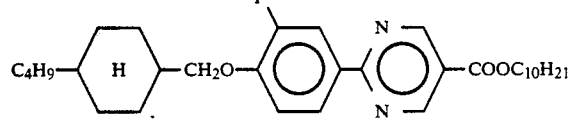 1-42
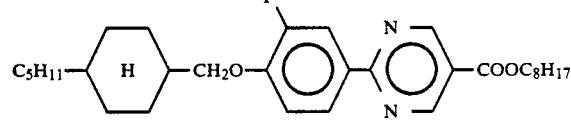 1-43
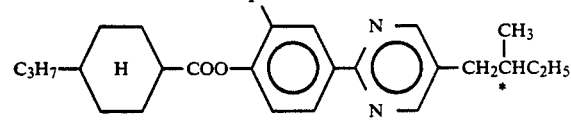 1-44
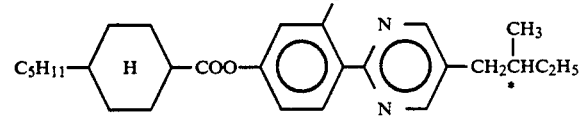 1-45
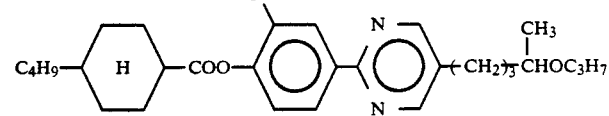 1-46

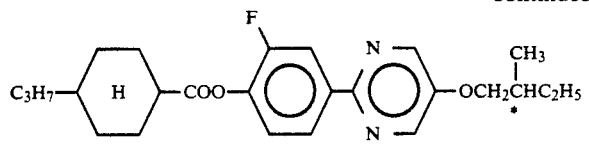 1-47
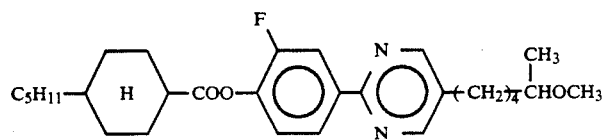 1-48
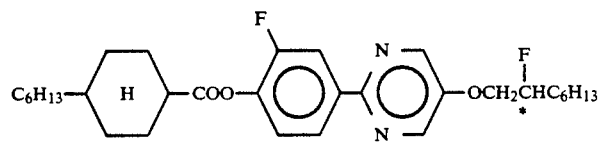 1-49
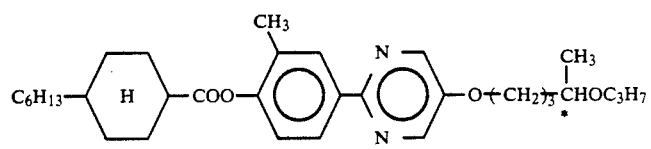 1-50
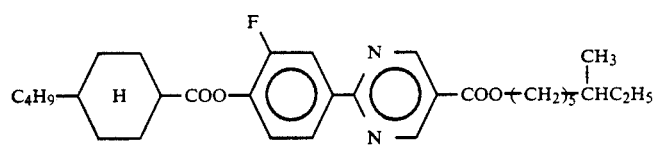 1-51
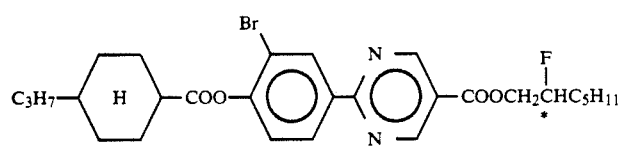 1-52
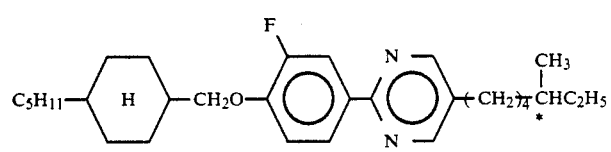 1-53
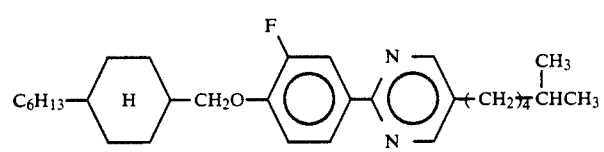 1-54
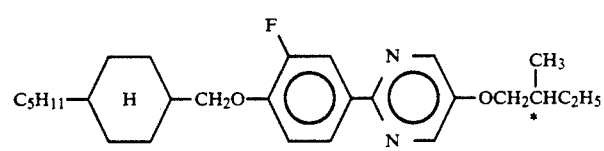 1-55
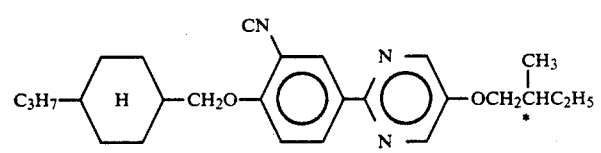 1-56
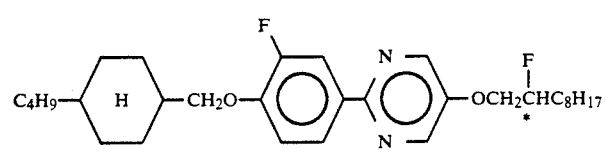 1-57

-continued
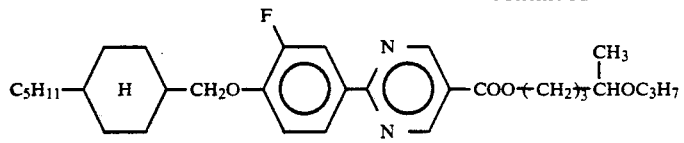 1-58
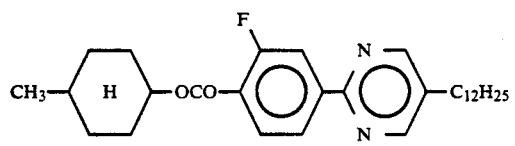 1-59
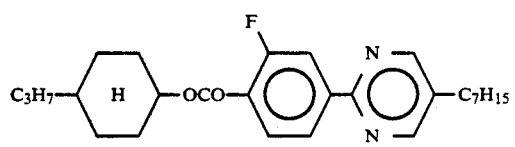 1-60
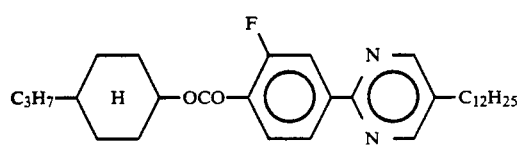 1-61
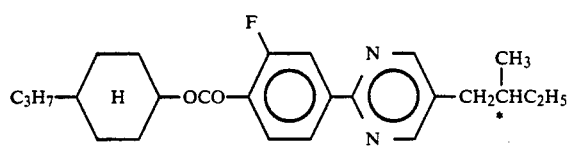 1-62
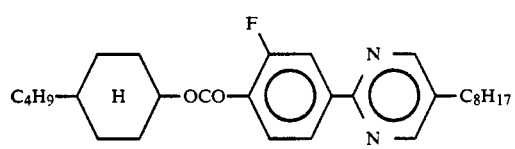 1-63
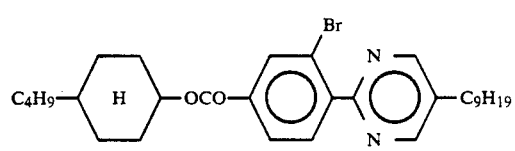 1-64
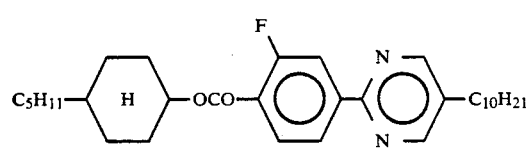 1-65
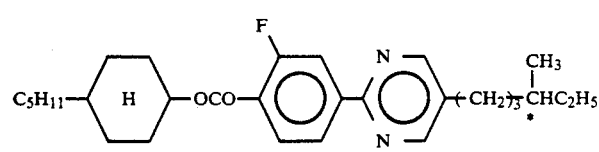 1-66
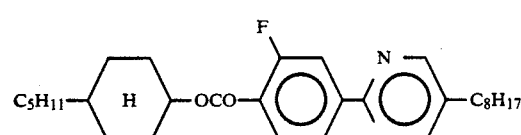 1-67
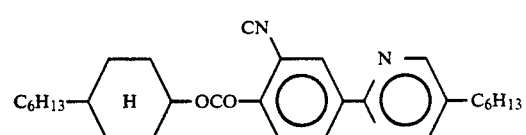 1-68

1-69
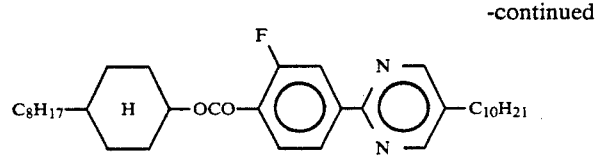
1-70
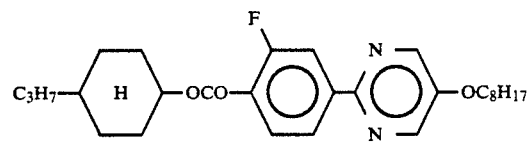
1-71
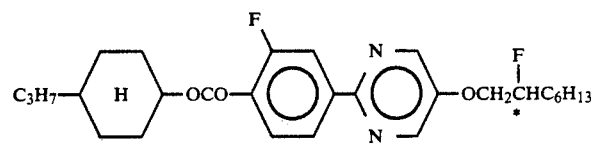
1-72
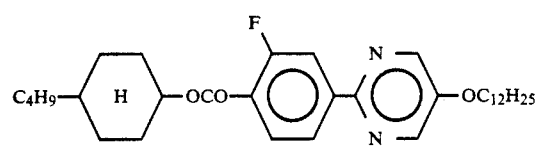
1-73
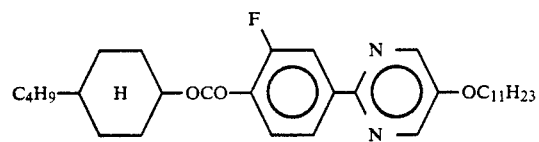
1-74
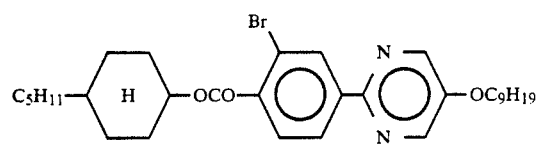
1-75
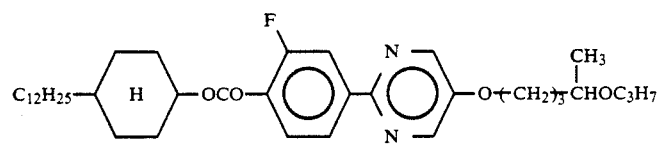
1-76
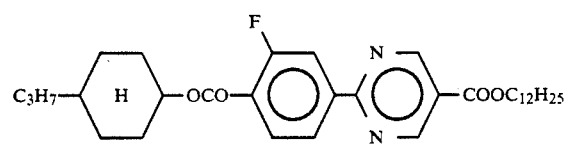
1-77
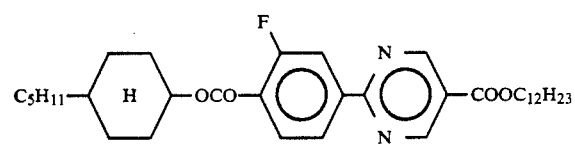
1-78
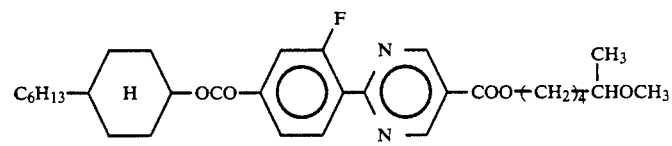
1-79
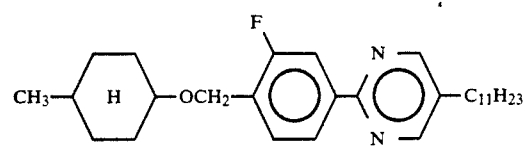

-continued
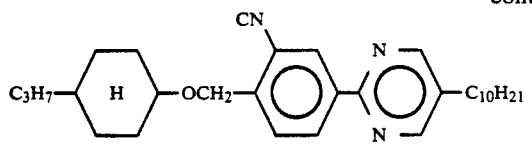
1-80
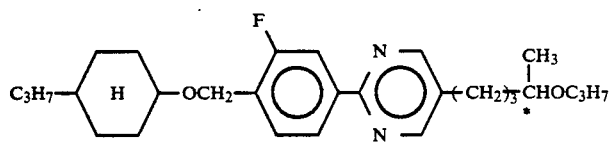
1-81
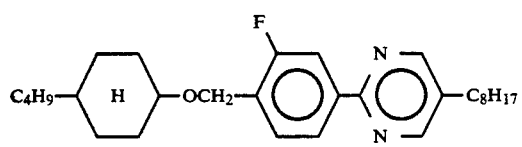
1-82
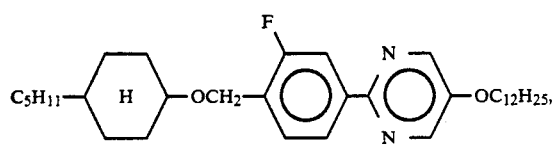
1-83
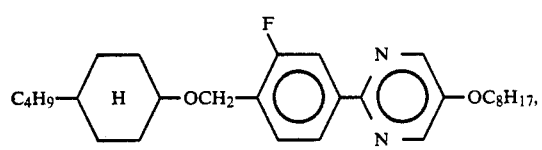
1-84
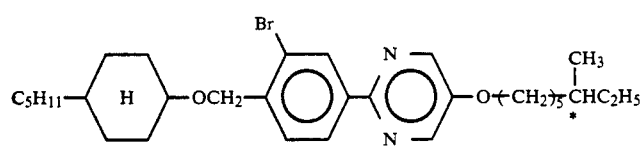
1-85
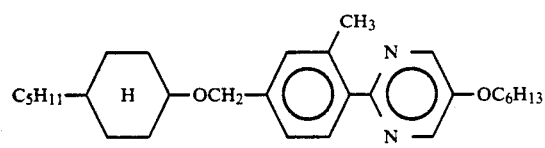
1-86
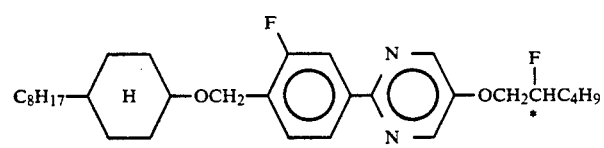
1-87
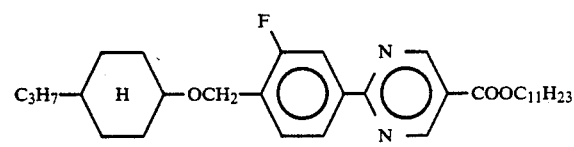
1-88
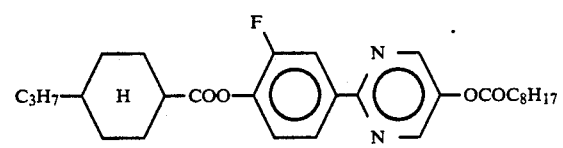
1-89
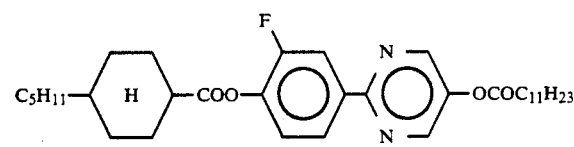
1-90

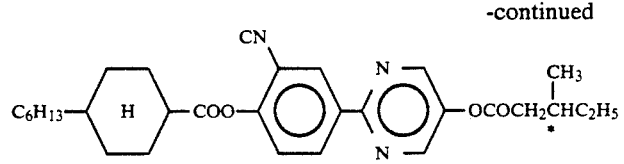
1-91
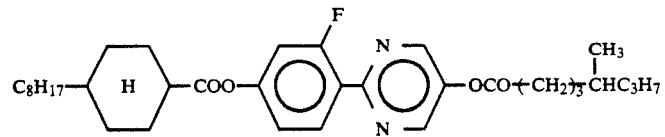
1-92
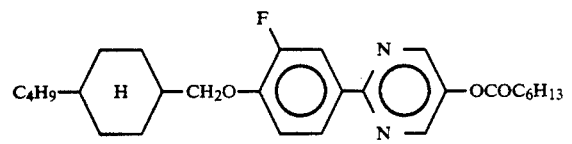
1-93
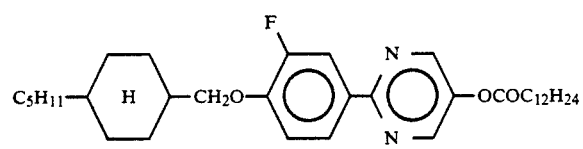
1-94
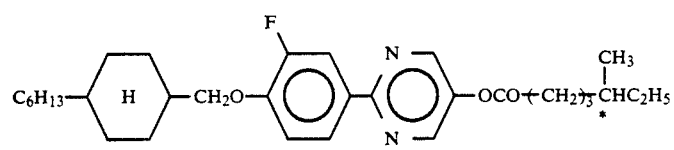
1-95
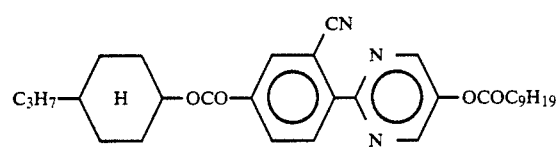
1-96
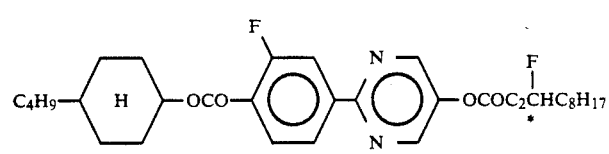
1-97
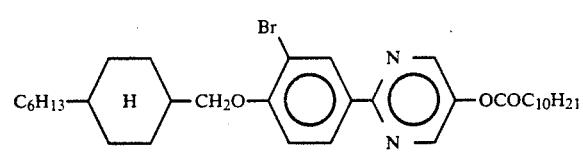
1-98
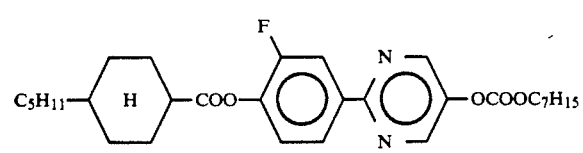
1-99
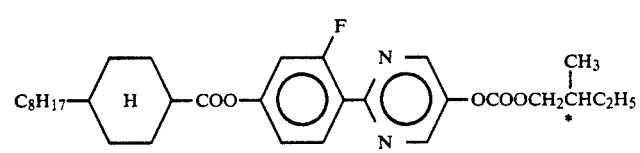
1-100
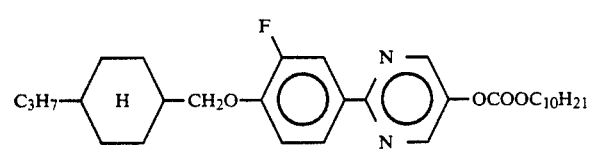
1-101

-continued
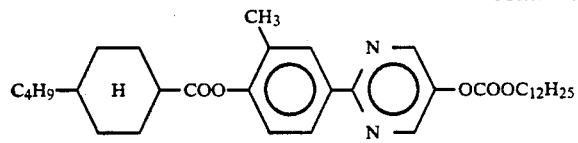 1-102
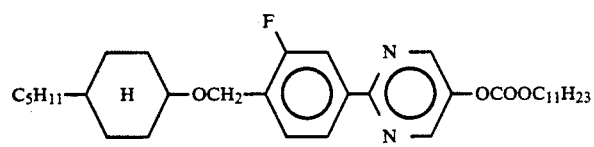 1-103
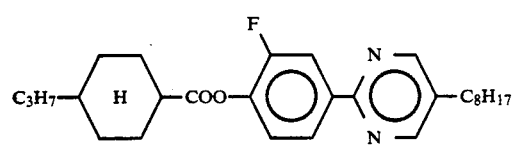 1-104
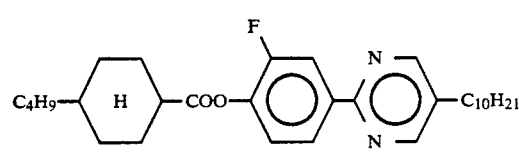 1-105
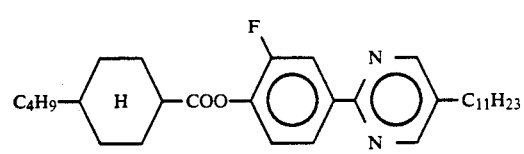 1-106
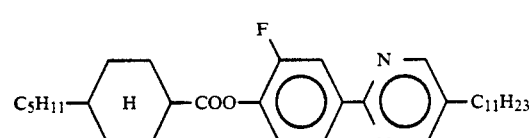 1-107
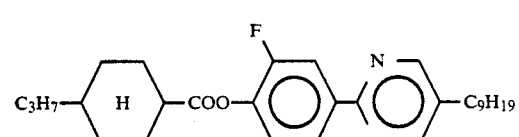 1-108
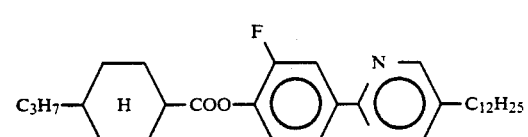 1-109
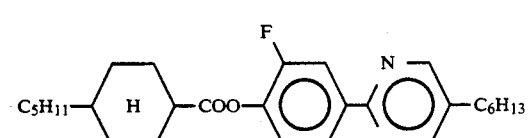 1-110
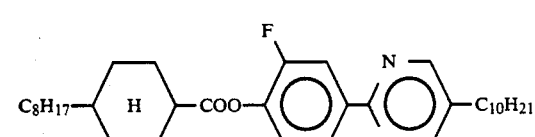 1-111
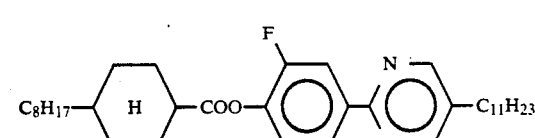 1-112

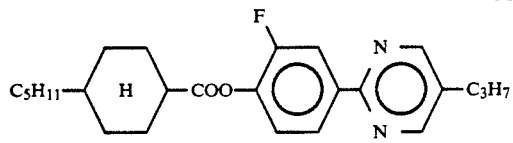
1-113

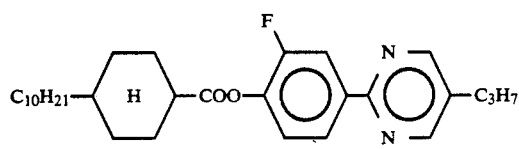
1-114

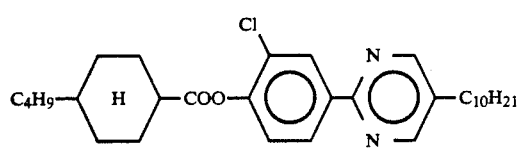
1-115

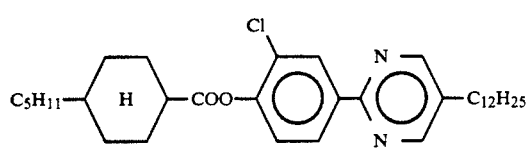
1-116

The compounds represented by the formula (II) may be synthesized through processes as disclosed by, e.g., East German Patent 95892 (1973) and Japanese Patent Publication (KOKOKU) 5434/1987. For example, the compound represented by the following formula:

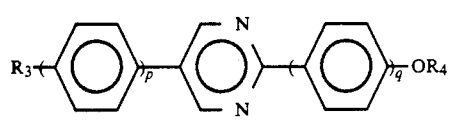

may be synthesized through the following reaction scheme.

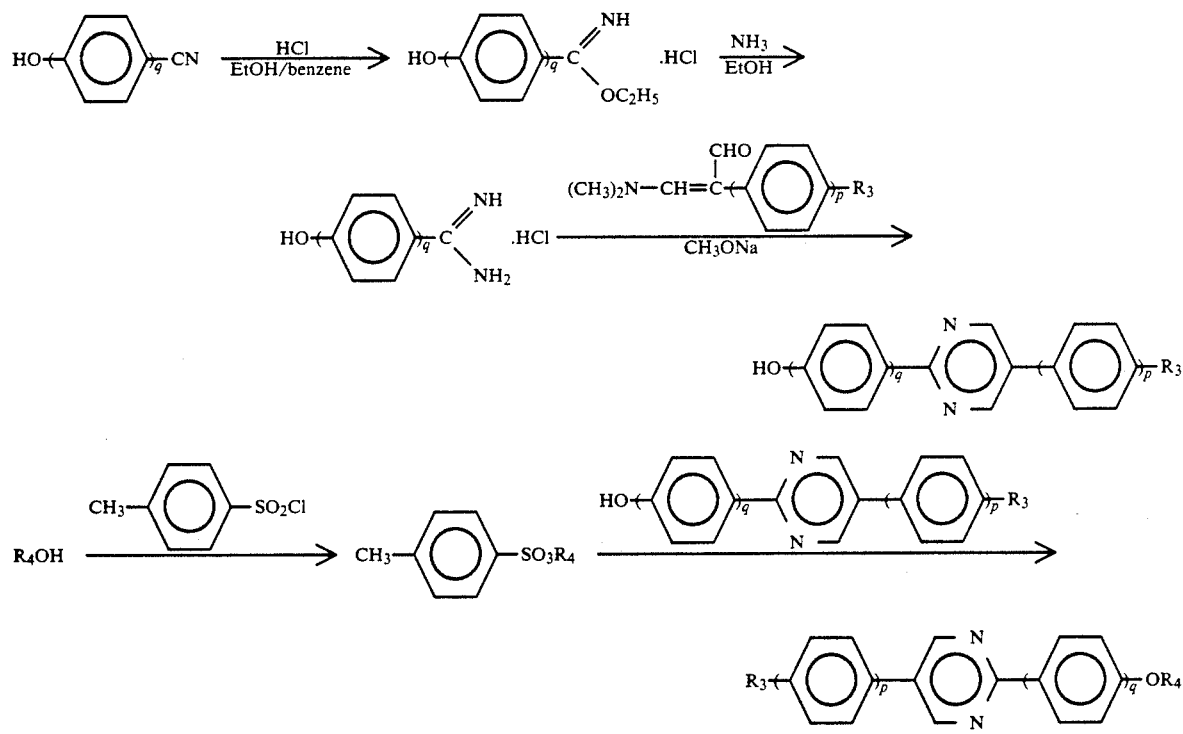

In the above, $R_3$, $R_4$, p and q are the same as defined above.

A representative example of synthesis of a compound represented by the formula (II) is described below.

SYNTHESIS EXAMPLE 1

Synthesis or compound Example No. 2-54 shown below

A solution of 1.83 g (9.6 mmol) of p-toluene-sulfonic acid chloride in 5 ml of pyridine was added dropwise to a solution of 1.06 g (8.0 mmol) of 5-methoxyhexanol in 5 ml of pyridine below 5° C. on an iced water bath. After stirring for 6 hours at room temperature, the reaction mixture was injected into 100 ml of cold water and, after being acidified with 6N-hydrochloric acid, was extracted with isopropyl ether. The organic layer was washed with water and dried with anhydrous magnesium sulfate, followed by distilling-off of the solvent to obtain 5-methoxyhexyl-p-toluenesulfonate.

Separately, 2.0 g (6.41 mmol) of 5-decyl-2-(p-hydroxyphenyl)pyrimidine and 0.61 g of potassium hydroxide were added to 10 ml of dimethylformamide, and the mixture was stirred for 40 min. at 100° C. To the mixture was added the above-prepared 5-methoxyhexyl-p-toluenesulfonate followed by 4 hours of stirring under heating at 100° C. After the reaction, the reaction mixture was poured into 100 ml of cold water and extracted with benzene, followed by washing with water, drying with anhydrous magnesium sulfate and distilling-off of the solvent, to obtain a pale yellow oily product. The product was purified by column chromatography (silica gel—ethyl acetate/benzene=1/9) and recrystallized from hexane to obtain 1.35 g of 5-decyl-2-[4-(5'-methoxyhexyloxy)phenyl]pyrimidine.

Phase transitions temperature (°C.)

Cryst. $\underset{<0.2}{\overset{3.5}{\rightleftarrows}}$ SmC $\underset{26.7}{\overset{27.9}{\rightleftarrows}}$ SmA $\underset{37.6}{\overset{40.3}{\rightleftarrows}}$ Iso.

Cryst.: crystal phase,
SmC: smectic C phase,
SmA: smectic A phase, and
Iso.: isotropic phase.

Specific examples of the mesomorphic compounds represented by the above-mentioned general formula (II) may include those shown by the following structural formulas.

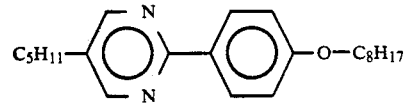 (2-1)

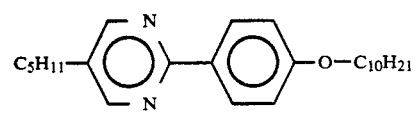 (2-2)

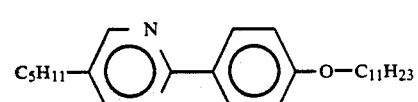 (2-3)

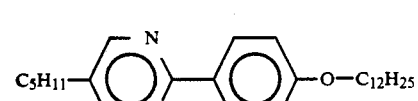 (2-4)

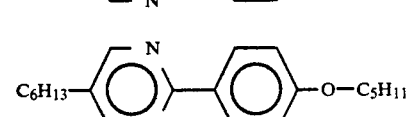 (2-5)

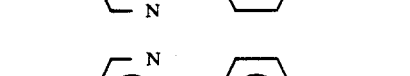 (2-6)

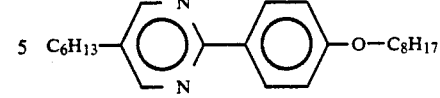 (2-7)

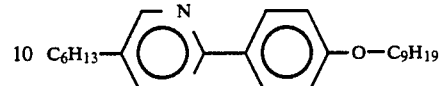 (2-8)

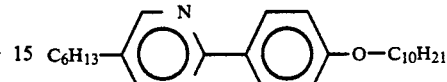 (2-9)

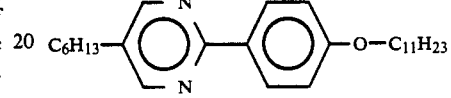 (2-10)

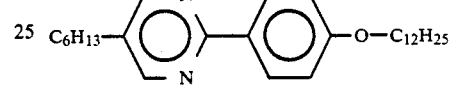 (2-11)

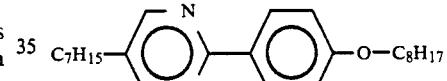 (2-12)

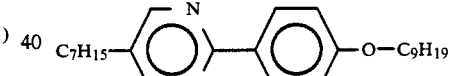 (2-13)

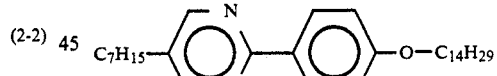 (2-14)

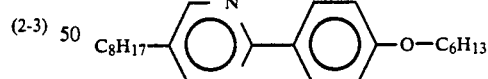 (2-15)

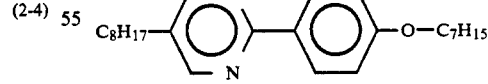 (2-16)

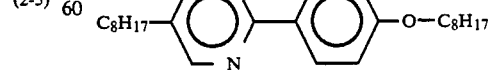 (2-17)

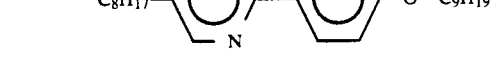 (2-18)

 (2-19)

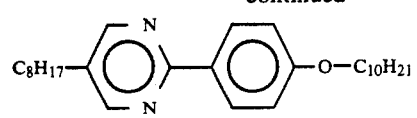 (2-20)
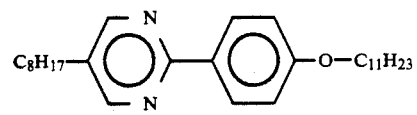 (2-21)
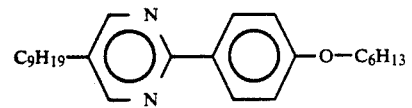 (2-22)
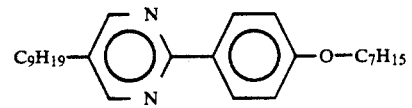 (2-23)
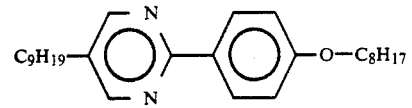 (2-24)
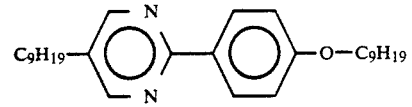 (2-25)
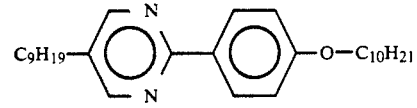 (2-26)
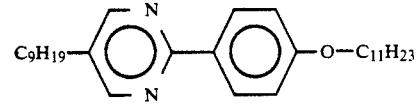 (2-27)
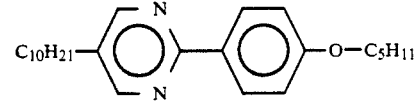 (2-28)
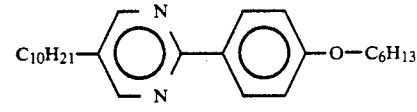 (2-29)
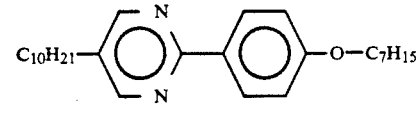 (2-30)
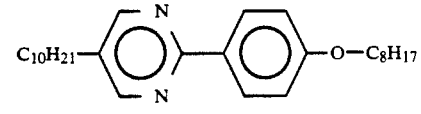 (2-31)
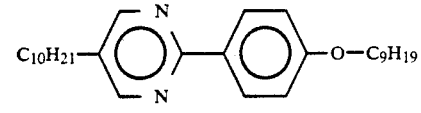 (2-32)

(2-46) C8H17O-[pyrimidine]-C6H4-C7H15

(2-47) C8H17O-[pyrimidine]-C6H4-C9H19

(2-48) C9H19O-[pyrimidine]-C6H4-C8H17

(2-49) C9H19O-[pyrimidine]-C6H4-C9H19

(2-50) C9H19O-[pyrimidine]-C6H4-C10H21

(2-51) C10H21O-[pyrimidine]-C6H4-C6H13

(2-52) C8H17-[pyrimidine]-C6H4-O(CH2)3CH(CH3)-O-C3H7

(2-53) C10H21-[pyrimidine]-C6H4-O(CH2)3CH(CH3)-O-C3H7

(2-54) C10H21-[pyrimidine]-C6H4-O(CH2)4CH(CH3)-O-CH3

(2-55) C12H25-[pyrimidine]-C6H4-O(CH2)4CH(CH3)-O-CH3

(2-56) C6H13-[pyrimidine]-C6H4-OC(=O)-C8H17

(2-57) C6H13-[pyrimidine]-C6H4-OC(=O)-C10H21

(2-58) C7H15-[pyrimidine]-C6H4-OC(=O)-C8H17

(2-59) C7H15-[pyrimidine]-C6H4-OC(=O)-C10H21

(2-60) C8H17-[pyrimidine]-C6H4-OC(=O)-C4H9

(2-61) C8H17-[pyrimidine]-C6H4-OC(=O)-C6H13

(2-62) C8H17-[pyrimidine]-C6H4-OC(=O)-C7H15

(2-63) C8H17-[pyrimidine]-C6H4-OC(=O)-C8H17

(2-64) C8H17-[pyrimidine]-C6H4-OC(=O)-C9H19

(2-65) C8H17-[pyrimidine]-C6H4-OC(=O)-C10H21

(2-65) C8H17-[pyrimidine]-C6H4-OC(=O)-C12H25

(2-66) C9H19-[pyrimidine]-C6H4-OC(=O)-C6H13

(2-67) C9H19-[pyrimidine]-C6H4-OC(=O)-C7H15

(2-68) C9H19-[pyrimidine]-C6H4-OC(=O)-C8H17

(2-69) C9H19-[pyrimidine]-C6H4-OC(=O)-C9H19

(2-70) C9H19-[pyrimidine]-C6H4-OC(=O)-C12H25

(2-71) C₁₀H₂₁–[pyrimidine]–[phenyl]–OC(=O)C₃H₇

(2-72) C₁₀H₂₁–[pyrimidine]–[phenyl]–OC(=O)C₄H₉

(2-73) C₁₀H₂₁–[pyrimidine]–[phenyl]–OC(=O)C₅H₁₁

(2-74) C₁₀H₂₁–[pyrimidine]–[phenyl]–OC(=O)C₆H₁₃

(2-75) C₁₀H₂₁–[pyrimidine]–[phenyl]–OC(=O)C₇H₁₅

(2-76) C₁₀H₂₁–[pyrimidine]–[phenyl]–OC(=O)C₈H₁₇

(2-77) C₁₀H₂₁–[pyrimidine]–[phenyl]–OC(=O)C₉H₁₉

(2-78) C₁₀H₂₁–[pyrimidine]–[phenyl]–OC(=O)C₁₀H₂₁

(2-79) C₁₀H₂₁–[pyrimidine]–[phenyl]–OC(=O)C₁₁H₂₃

(2-80) C₁₀H₂₁–[pyrimidine]–[phenyl]–OC(=O)C₁₄H₂₉

(2-81) C₁₁H₂₃–[pyrimidine]–[phenyl]–OC(=O)C₆H₁₃

(2-82) C₁₁H₂₃–[pyrimidine]–[phenyl]–OC(=O)C₇H₁₅

(2-83) C₁₁H₂₃–[pyrimidine]–[phenyl]–OC(=O)C₈H₁₇

(2-84) C₁₁H₂₃–[pyrimidine]–[phenyl]–OC(=O)C₉H₁₉

(2-85) C₁₁H₂₃–[pyrimidine]–[phenyl]–OC(=O)C₁₀H₂₁

(2-86) C₁₂H₂₅–[pyrimidine]–[phenyl]–OC(=O)C₆H₁₃

(2-87) C₁₂H₂₅–[pyrimidine]–[phenyl]–OC(=O)C₈H₁₇

(2-88) C₁₂H₂₅–[pyrimidine]–[phenyl]–OC(=O)C₁₀H₂₁

(2-89) C₁₄H₂₉–[pyrimidine]–[phenyl]–OC(=O)C₆H₁₃

(2-90) C₉H₁₉–O–[pyrimidine]–[phenyl]–OC(=O)C₇H₁₅

(2-91) C₁₀H₂₁–O–[pyrimidine]–[phenyl]–OC(=O)C₆H₁₃

(2-92) C₁₂H₂₅–[pyrimidine]–[phenyl]–OC(=O)CH(CH₃)–OC₅H₁₁

(2-93) C₁₀H₂₁–[pyrimidine]–[phenyl]–OC(=O)CH(CH₃)–C₂H₅

(2-94) C₁₀H₂₁–[pyrimidine]–[phenyl]–O–CH(CH₃)CH₂–O–C₃H₇

(2-95) C₅H₁₁–[pyrimidine]–[phenyl]–[phenyl]–C₆H₁₃

(2-96) C₇H₁₅–[pyrimidine]–[phenyl]–[phenyl]–C₆H₁₃

-continued

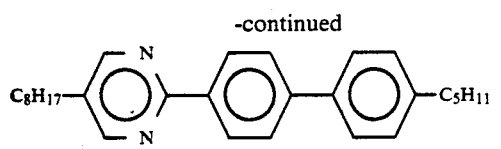 (2-97)

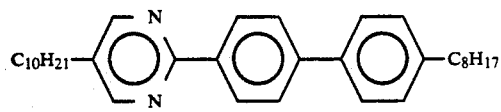 (2-98)

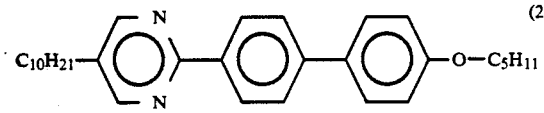 (2-99)

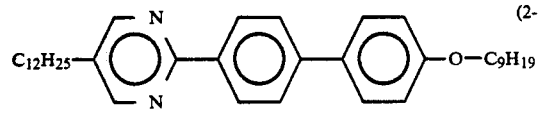 (2-100)

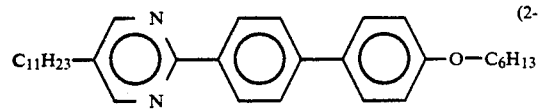 (2-101)

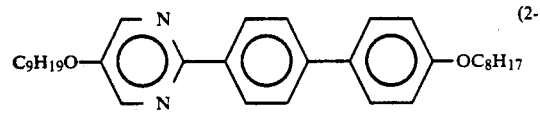 (2-102)

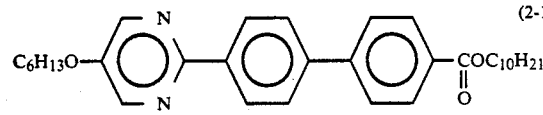 (2-103)

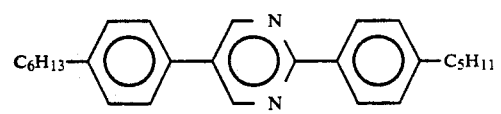 (2-104)

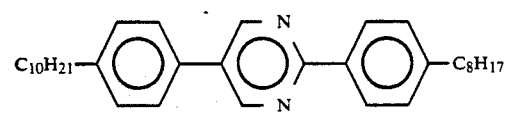 (2-105)

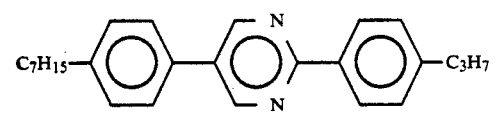 (2-106)

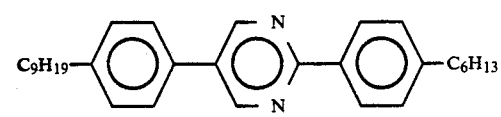 (2-107)

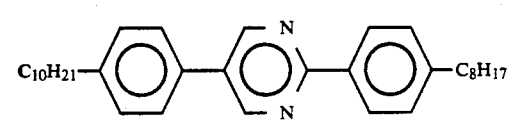 (2-108)

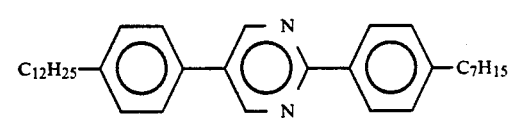 (2-109)

-continued

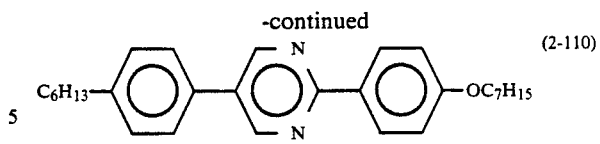 (2-110)

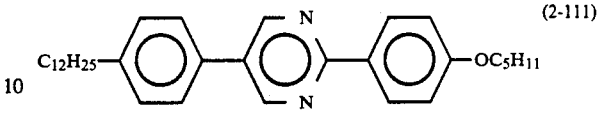 (2-111)

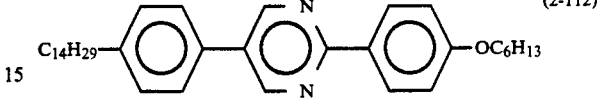 (2-112)

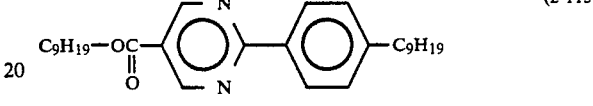 (2-113)

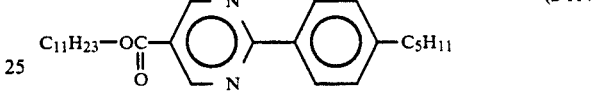 (2-114)

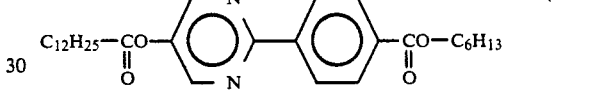 (2-115)

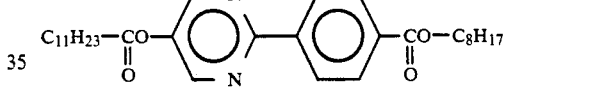 (2-116)

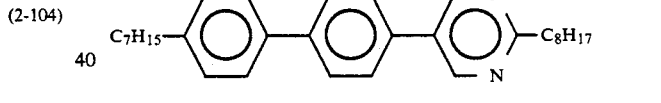 (2-117)

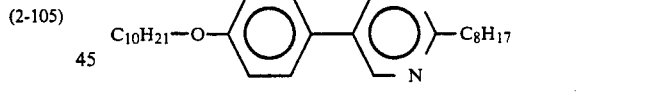 (2-118)

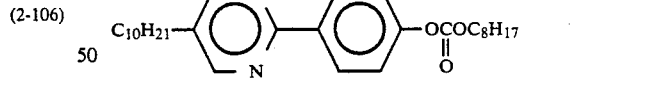 (2-119)

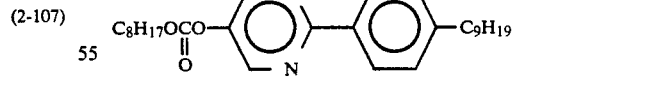 (2-120)

The compounds represented by the formula (III) may be synthesized through processes as disclosed by, e.g., Japanese Laid-Open Patent Applications (KOKAI) 22042/1988 and 122651/1988. Representative examples of synthesis of the compounds are shown hereinbelow.

SYNTHESIS EXAMPLE 2

Synthesis of Compound Example 3–28 shown below 1.00 g (4.16 mM) of p-2-fluorooctyloxyphenol was dissolved in a mixture of 10 ml of pyridine and 5 ml of toluene, and a solution of 1.30 g (6.00 mM) of trans-4-n- pentylcyclohexanecarbonyl chloride was added dropwise thereto in 20-40 min. at below 5° C. After the addition, the mixture was stirred overnight at room temperature to obtain a white precipitate.

After the reaction, the reaction product was extracted with benzene, and the resultant benzene layer was washed with distilled water, followed by drying with magnesium sulfate and distilling-off of the benzene, purification by silica gel column chromatography and recrystallization from ethanol/methanol to obtain 1.20 g (2.85 mM) of trans-4-n-pentylcyclohexane-carboxylic acid-p-2-fluorooctyloxyphenyl-ester. (Yield: 68.6%)

NMR data (ppm)
0.83-2.83 ppm (34H, m)
4.00-4.50 ppm (2H, q)
7.11 ppm 4H, s)

IR data (cm$^{-1}$): 3456, 2928, 2852, 1742, 1508, 1470, 1248, 1200, 1166, 1132, 854.

Phase transition temperature (°C.)

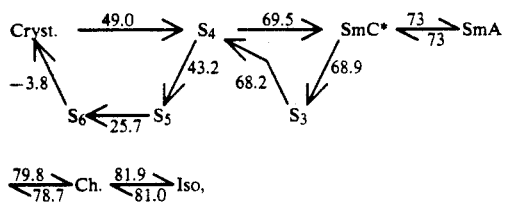

$S_3$-$S_6$:phases of higher order than SmC*,
SmC*:chiral smectic C phase, and
Ch.:cholesteric phase.

SYNTHESIS EXAMPLE 3

Synthesis of Compound Example 3-85

In a vessel sufficiently replaced with nitrogen, 0.40 g (3.0 mmol) of (−)-2-fluoroheptanol and 1.00 g (13 mmol) of dry pyridine were placed and dried for 30 min. under cooling on an ice bath. Into the solution, 0.69 g (3.6 mmol) of p-toluenesulfonyl chloride was added, and the mixture was stirred for 5 hours. After the reaction, 10 ml of 1N-HCl was added, and the resultant mixture was subjected to two times of extraction with 10 ml of methylene chloride. The extract liquid was washed once with 10 ml of distilled water and dried with an appropriate amount of anhydrous sodium sulfate, followed by distilling-off of the solvent to obtain 0.59 g (2.0 mmol) of (+)-2-fluoroheptyl p-toluenesulfonate.

The yield was 66%, and the product showed the following optical rotation and IR data.

Optical rotation:
[α]$_{26.4}^D$ +2.59 degrees (c=1, CHCl$_3$)
[α]$_{23.6_D}$ +9.58 degrees (c=1, CHCl$_3$)
IR (cm$^{-1}$):
2900, 2850, 1600, 1450, 1350, 1170, 1090 980, 810, 660, 550

0.43 g (1.5 mmol) of the thus obtained (+)-2-fluoroheptyl p-toluenesulfonate and 0.28 g (1.0 mmol) of 5-octyl-2-(4-hydroxyphenyl)pyrimidine were mixed with 0.2 ml of 1-butanol, followed by sufficient stirring. To the solution was quickly added a previously obtained alkaline solution of 0.048 g (1.2 mmol) of sodium hydroxide in 1.0 ml of 1-butanol, followed by 5.5 hours of heat-refluxing. After the reaction, 10 ml of distilled water was added, and the mixture was extracted respectively once with 10 ml of benzene and 5 ml of benzene, followed by drying with an appropriate amount of anhydrous sodium sulfate, distilling-off of the solvent and purification by silica gel column chromatography (chloroform) to obtain 0.17 g (0.43 mmol) of objective (+)-5-octyl-2-[4-(2-fluoroheptyloxy)phenyl]pyrimidine.

The yield was 43%, and the product showed the following optical rotation and IR data.

Optical rotation:
[α]$^{25.6}_D$+0.44 degree (c=1, CHCl$_3$)
[α]$^{22.4}_{435}$ +4.19 degrees (c=1, CHCl$_3$)
IR (cm$^{-1}$)
2900, 2850, 1600, 1580, 1420, 1250 1160, 800, 720, 650, 550.

Specific examples of the mesomorphic compounds represented by the above-mentioned general formula (III) may include those shown by the following structure formulas.

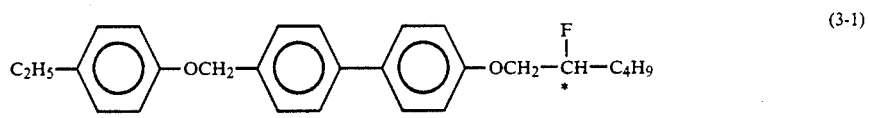

(3-1)

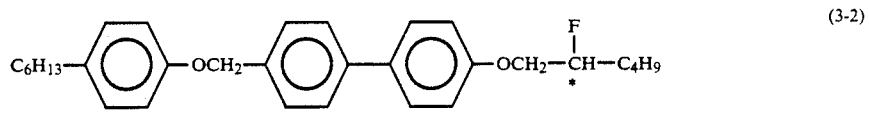

(3-2)

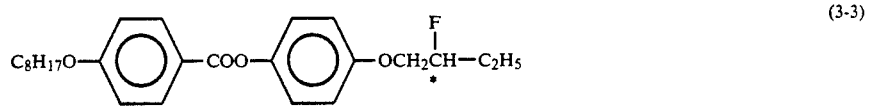

(3-3)

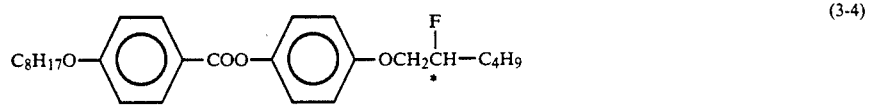

(3-4)

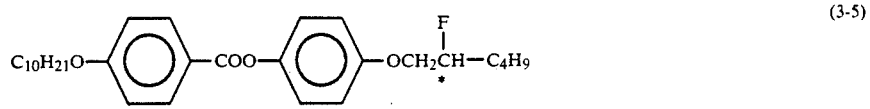

(3-5)

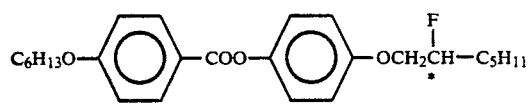
(3-6)
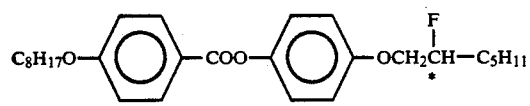
(3-7)
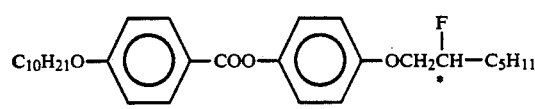
(3-8)
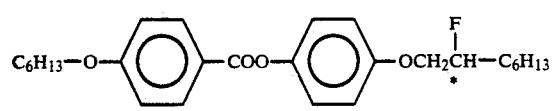
(3-9)
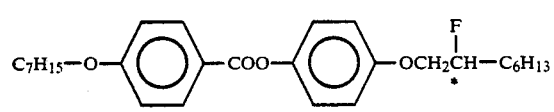
(3-10)
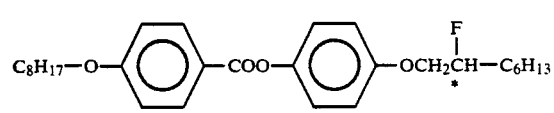
(3-11)
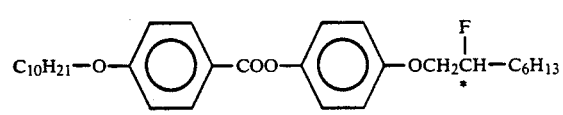
(3-12)
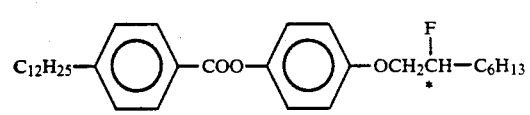
(3-13)
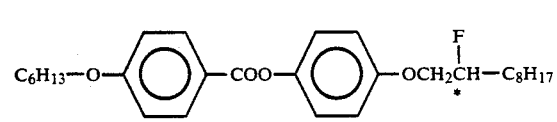
(3-14)
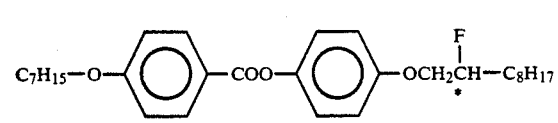
(3-15)
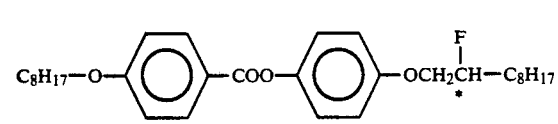
(3-16)
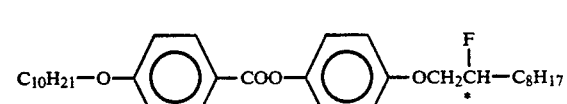
(3-17)
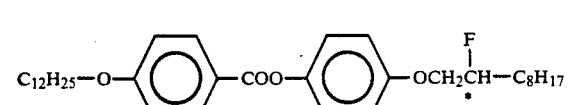
(3-18)

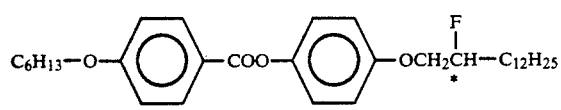
(3-19)
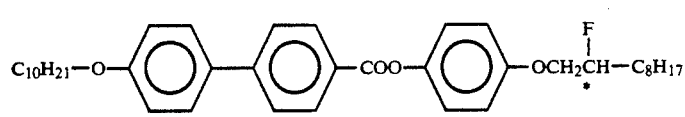
(3-20)
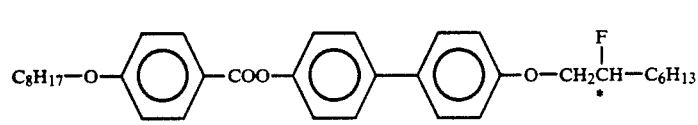
(3-21)
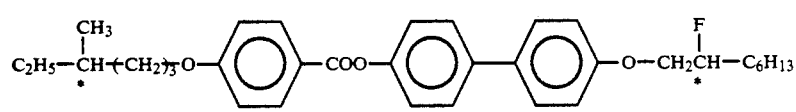
(3-22)
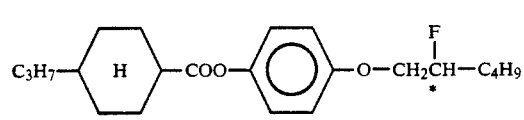
(3-23)
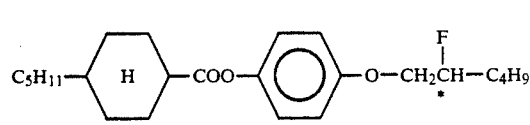
(3-24)
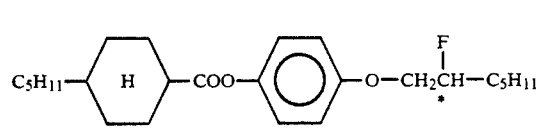
(3-25)
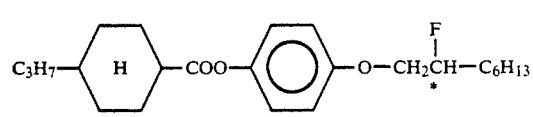
(3-26)
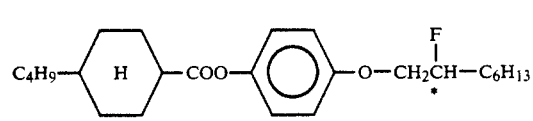
(3-27)
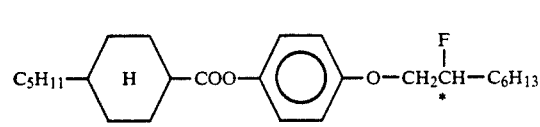
(3-28)
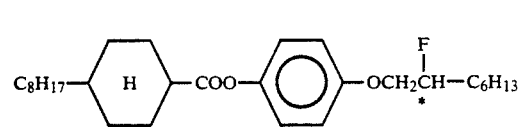
(3-29)
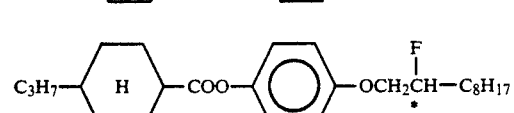
(3-30)
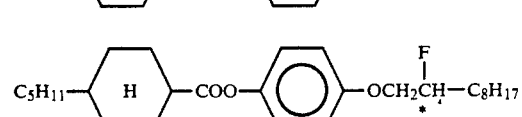
(3-31)
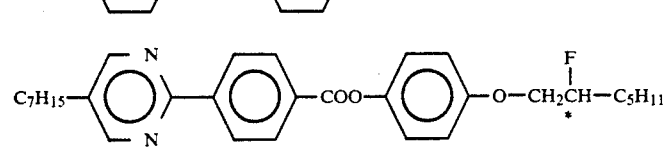
(3-32)

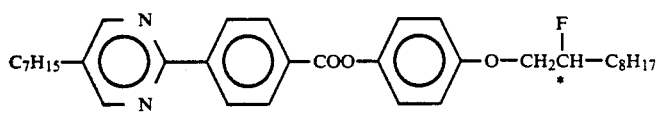 (3-32)
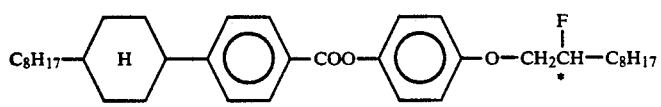 (3-33)
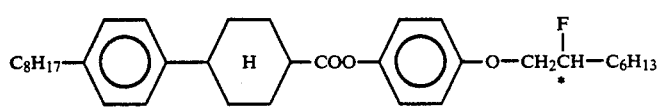 (3-34)
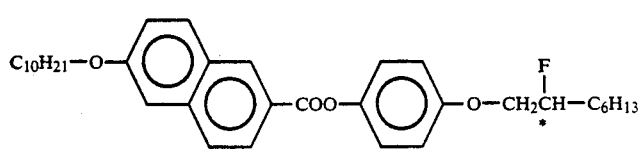 (3-35)
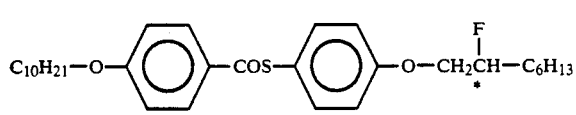 (3-36)
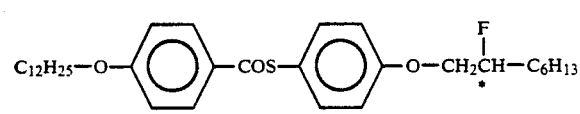 (3-37)
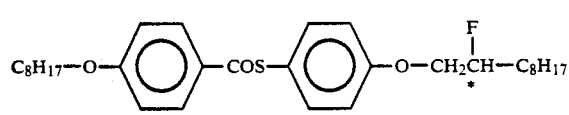 (3-38)
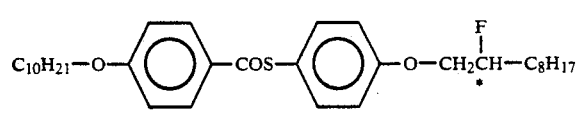 (3-39)
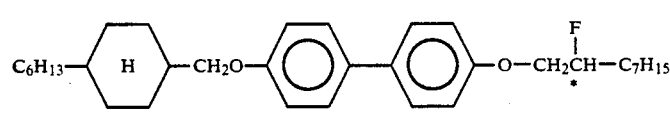 (3-40)
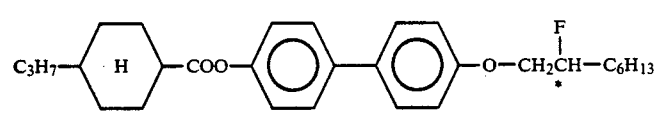 (3-41)
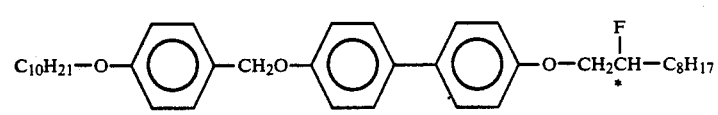 (3-42)
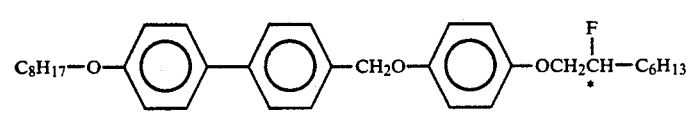 (3-43)
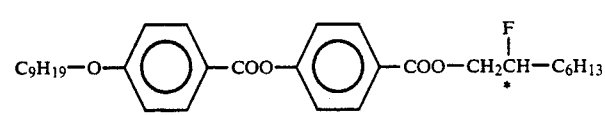 (3-44)

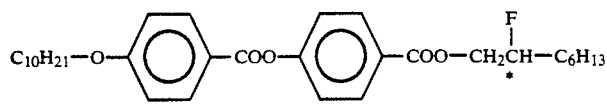
(3-45)
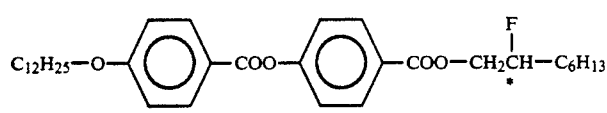
(3-46)
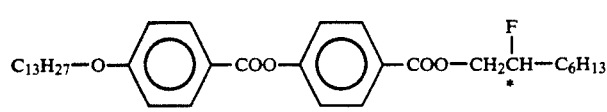
(3-47)
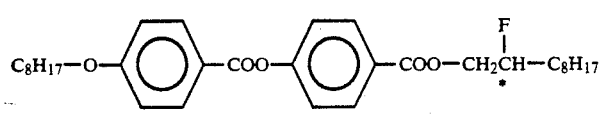
(3-48)
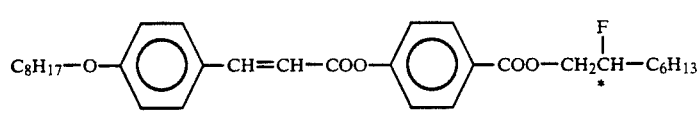
(3-49)
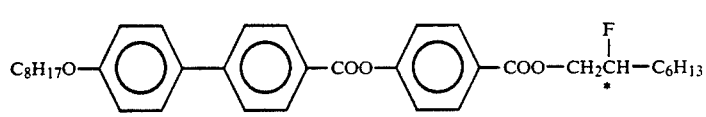
(3-50)
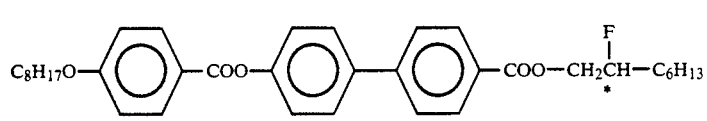
(3-52)
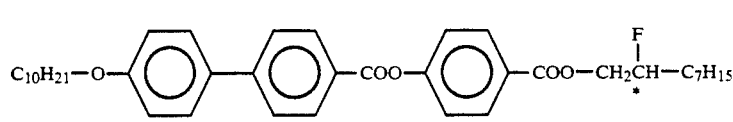
(3-53)
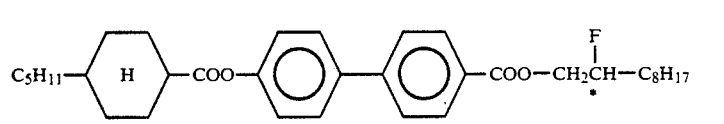
(3-54)
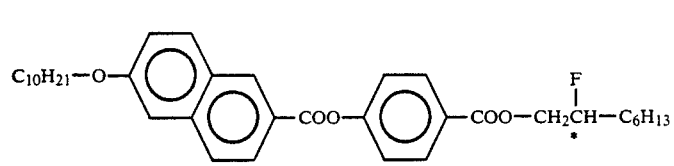
(3-55)
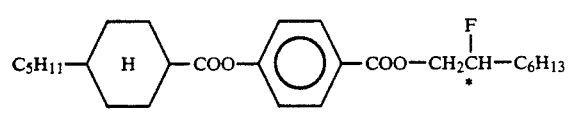
(3-56)
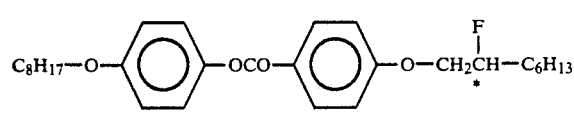
(3-57)
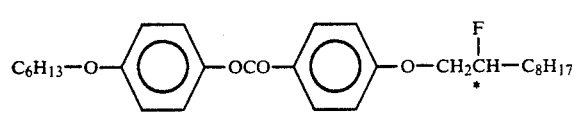
(3-58)

-continued
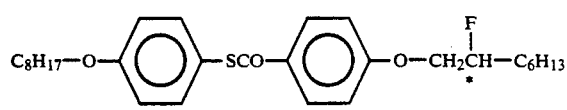
(3-59)
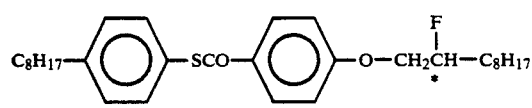
(3-60)
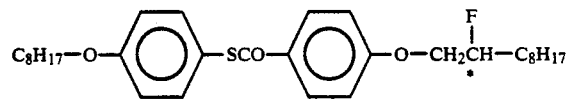
(3-61)
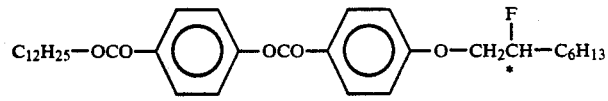
(3-62)
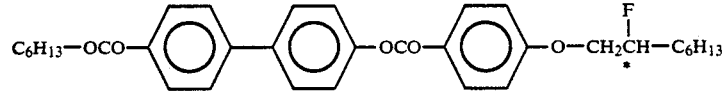
(3-63)
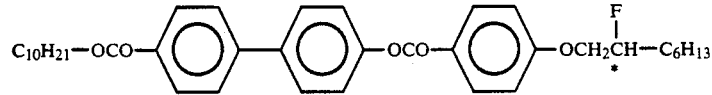
(3-64)
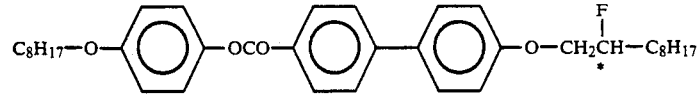
(3-65)
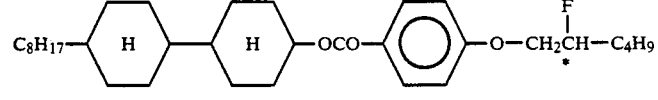
(3-66)
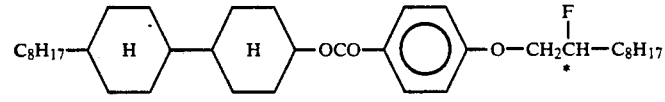
(3-67)
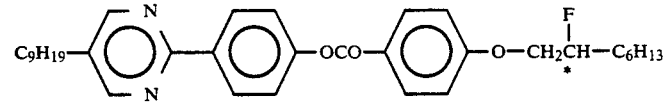
(3-68)
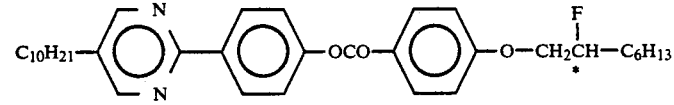
(3-69)
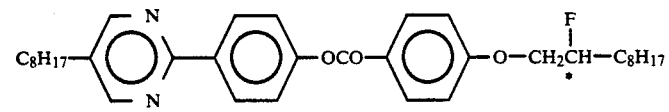
(3-70)
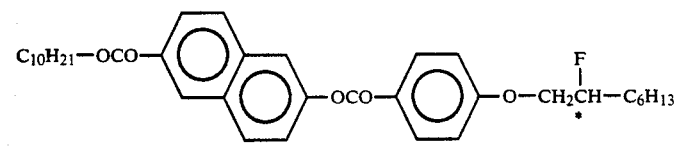
(3-71)

$C_8H_{17}O-\phenyl-\phenyl-COO-CH_2\overset{F}{\underset{*}{C}H}-C_6H_{13}$ (3-72)

$C_{10}H_{21}-O-\phenyl-\phenyl-COO-CH_2\overset{F}{\underset{*}{C}H}-C_6H_{13}$ (3-73)

$C_{12}H_{25}-\phenyl-\phenyl-COO-CH_2\overset{F}{\underset{*}{C}H}-C_6H_{13}$ (3-74)

$C_7H_{15}-\text{pyrimidine}-\phenyl-COO-CH_2\overset{F}{\underset{*}{C}H}-C_8H_{17}$ (3-75)

$C_7H_{15}-\text{cyclohexyl}-\text{pyrimidine}-\phenyl-COO-CH_2\overset{F}{\underset{*}{C}H}-C_8H_{17}$ (3-76)

$C_8H_{17}-COO-\phenyl-\phenyl-O-CH_2\overset{F}{\underset{*}{C}H}-C_6H_{13}$ (3-77)

$C_3H_7-\overset{CH_3}{\underset{}{C}H}-COO-\phenyl-\phenyl-O-CH_2\overset{F}{\underset{*}{C}H}-C_6H_{13}$ (3-78)

$C_3H_7-\overset{CH_3}{\underset{}{C}H}-COO-\phenyl-\phenyl-O-CH_2\overset{F}{\underset{*}{C}H}-C_8H_{17}$ (3-79)

$C_8H_{17}-\text{pyrimidine}-\phenyl-O-CH_2\overset{F}{\underset{*}{C}H}-C_2H_5$ (3-80)

$C_{10}H_{21}-\text{pyrimidine}-\phenyl-O-CH_2\overset{F}{\underset{*}{C}H}-C_2H_5$ (3-81)

$C_{12}H_{25}-\text{pyrimidine}-\phenyl-O-CH_2\overset{F}{\underset{*}{C}H}-C_2H_5$ (3-82)

$C_{10}H_{21}-\text{pyrimidine}-\phenyl-O-CH_2\overset{F}{\underset{*}{C}H}-C_4H_9$ (3-83)

$C_{12}H_{25}-\text{pyrimidine}-\phenyl-O-CH_2\overset{F}{\underset{*}{C}H}-C_4H_9$ (3-84)

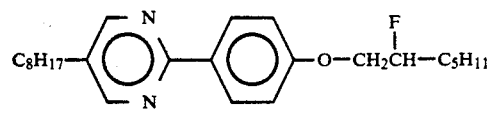 (3-85)
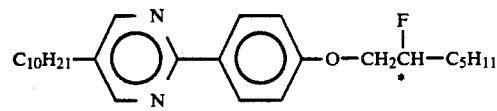 (3-86)
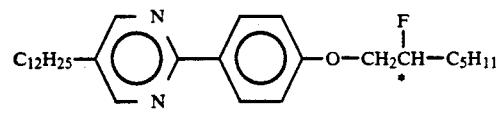 (3-87)
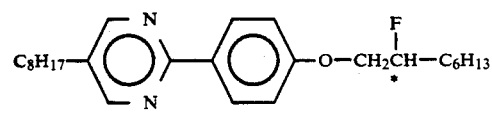 (3-88)
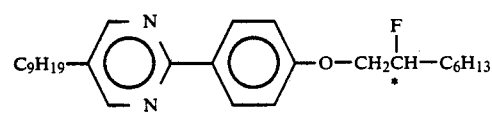 (3-89)
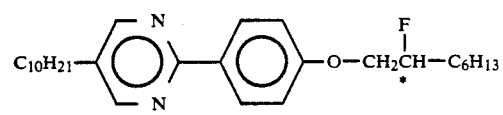 (3-90)
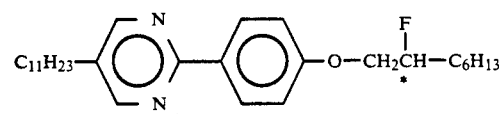 (3-91)
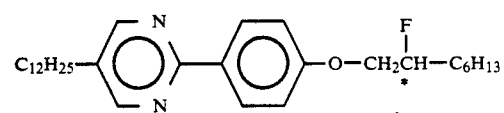 (3-92)
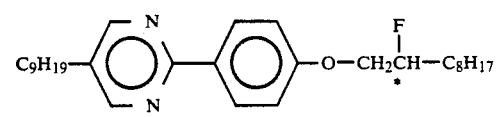 (3-93)
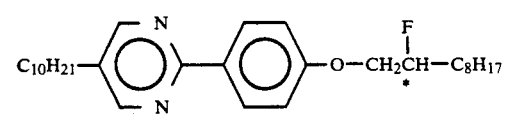 (3-94)
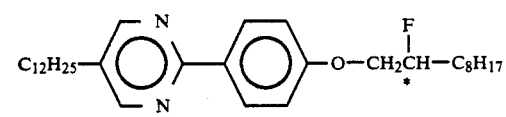 (3-95)
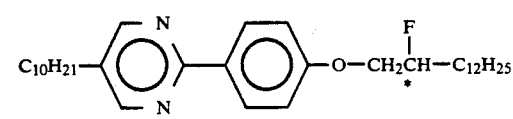 (3-96)
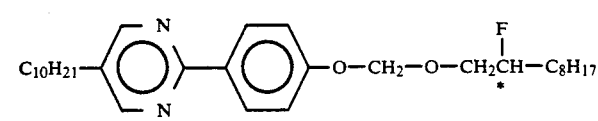 (3-97)

-continued
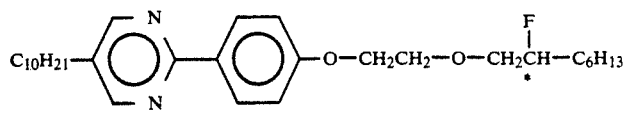
(3-98)
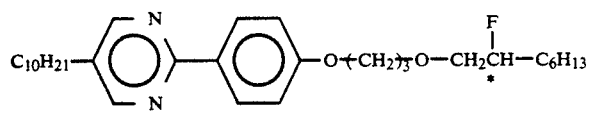
(3-99)
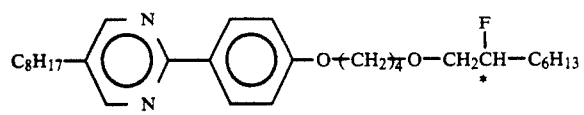
(3-100)
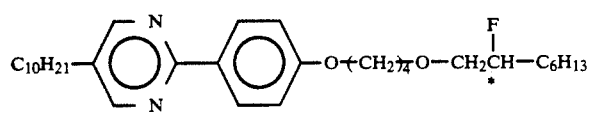
(3-101)
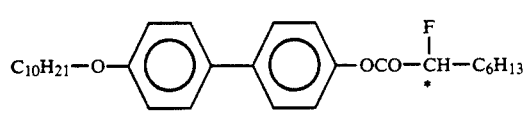
(3-102)
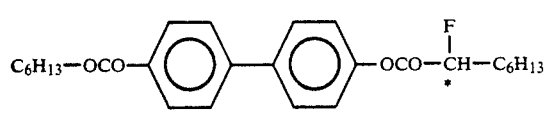
(3-103)
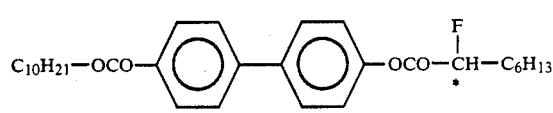
(3-104)
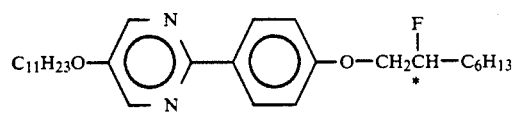
(3-105)
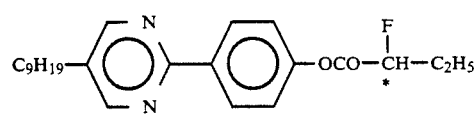
(3-106)
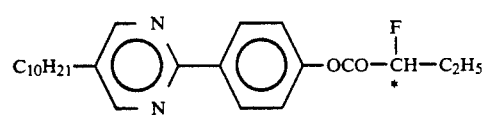
(3-107)
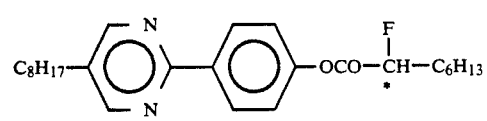
(3-108)
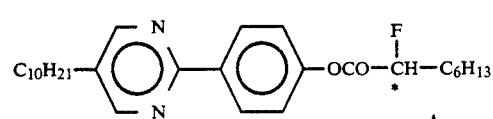
(3-109)
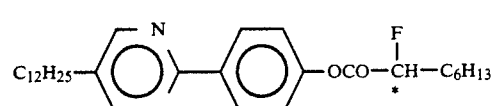
(3-110)

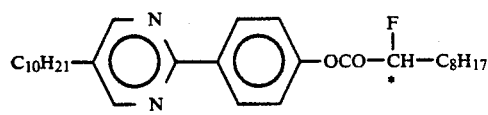 (3-111)

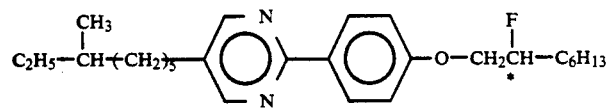 (3-112)

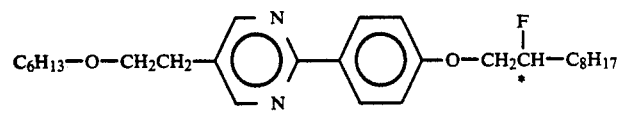 (3-113)

The liquid crystal composition according to the present invention may be obtained by mixing at least one species of the compound represented by the formula (I) and at least one species of another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above other than the compounds represented by the formulas (II) and (III) may include those denoted by the following structural formulas.

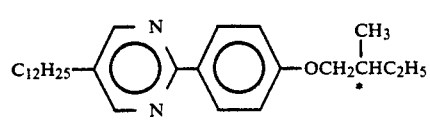 (1)

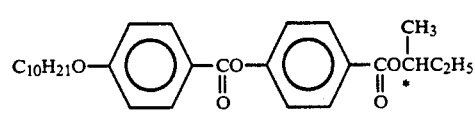 (2)

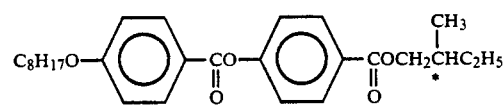 (3)

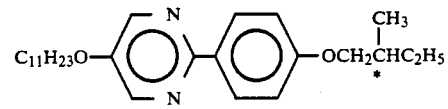 (4)

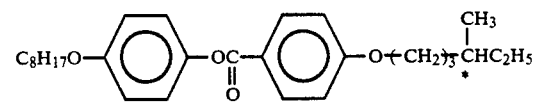 (5)

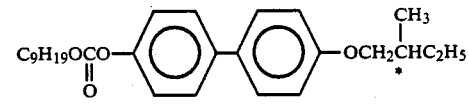 (6)

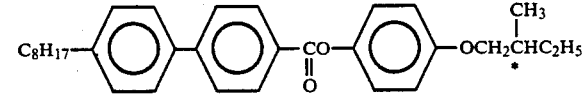 (7)

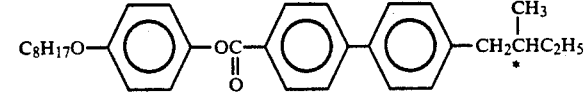 (8)

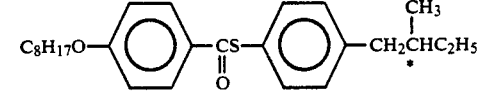 (9)

-continued
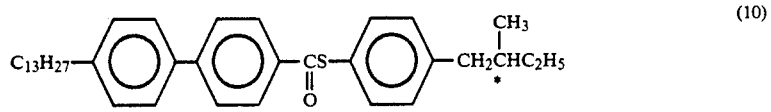
(10)
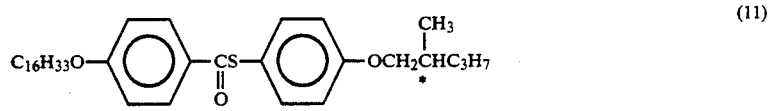
(11)
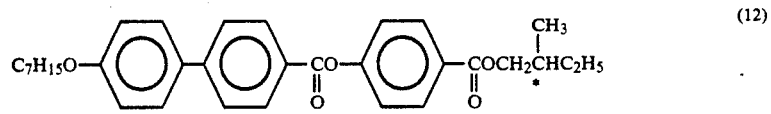
(12)
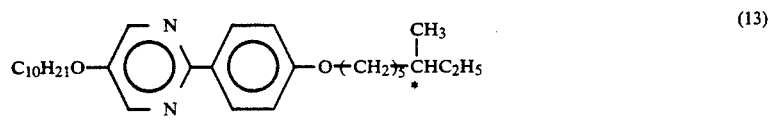
(13)
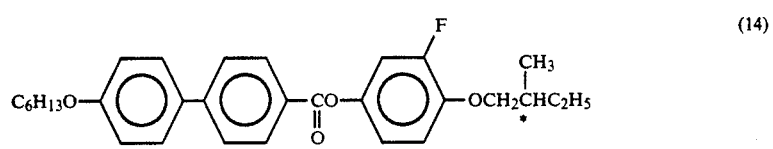
(14)
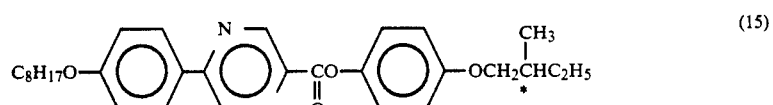
(15)
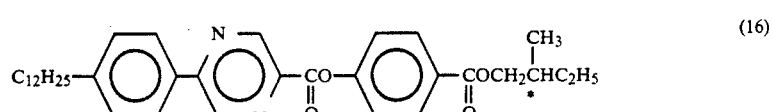
(16)
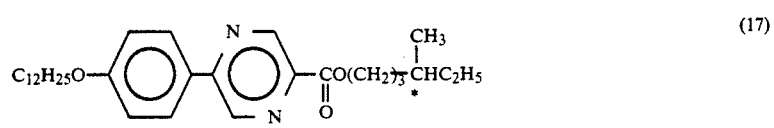
(17)
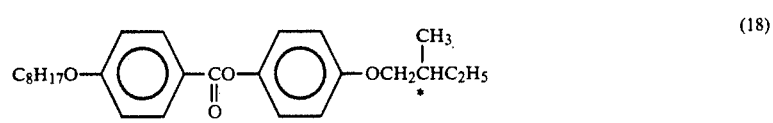
(18)
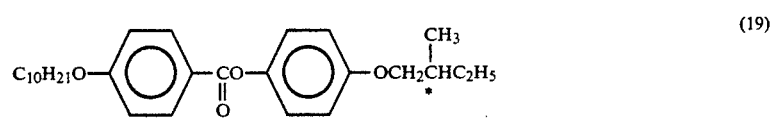
(19)
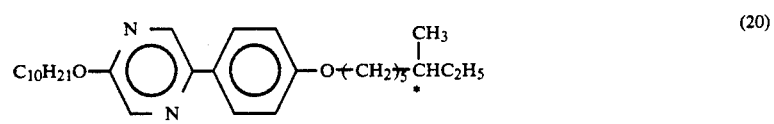
(20)
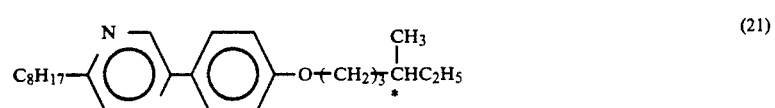
(21)
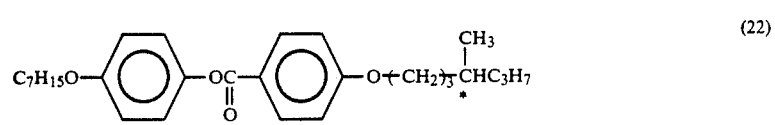
(22)

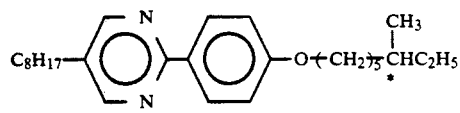 (23)
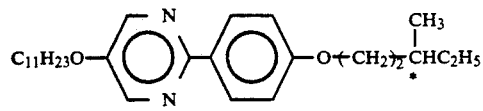 (24)
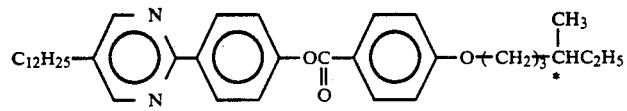 (25)
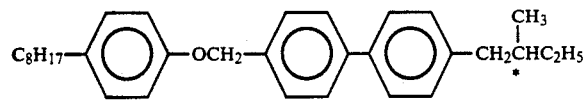 (26)
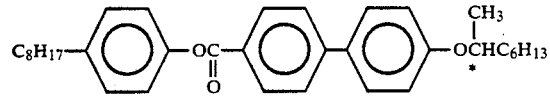 (27)
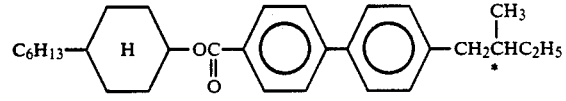 (28)
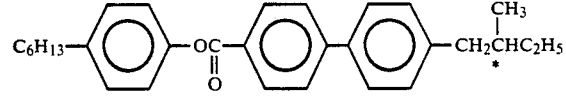 (29)
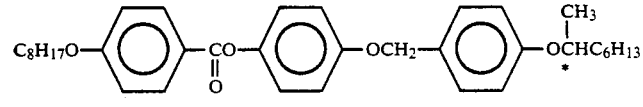 (30)
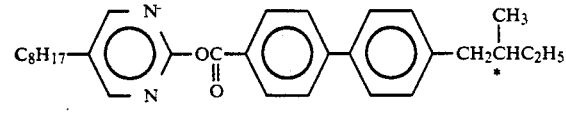 (31)
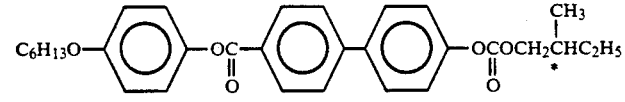 (32)
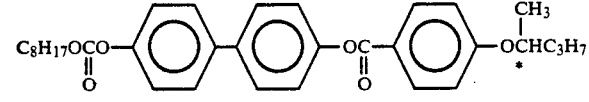 (33)
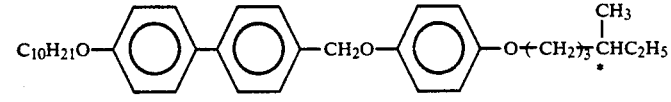 (34)
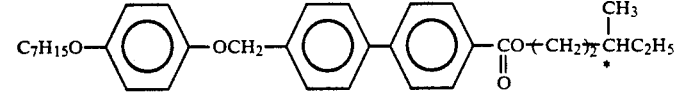 (35)

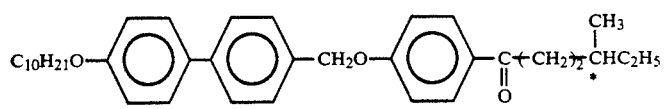 (36)
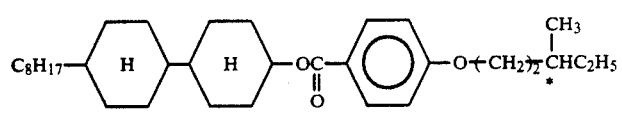 (37)
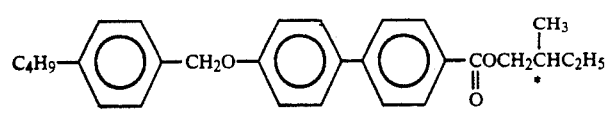 (38)
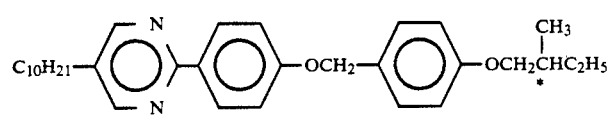 (39)
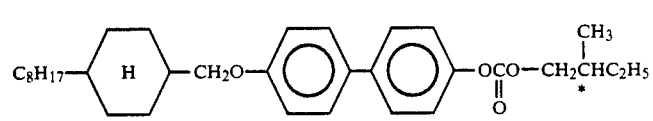 (40)
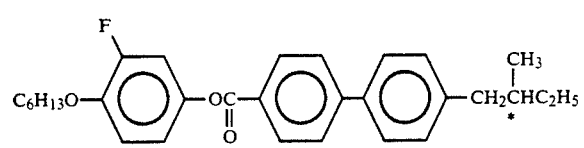 (41)
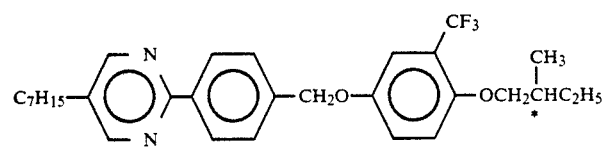 (42)
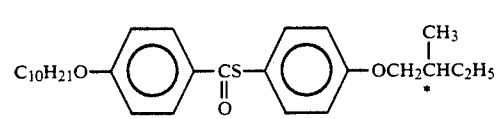 (43)
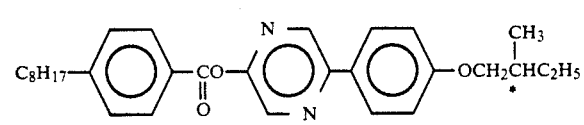 (44)
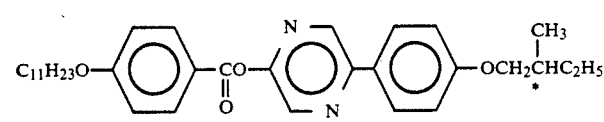 (45)
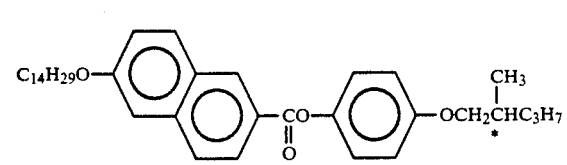 (46)
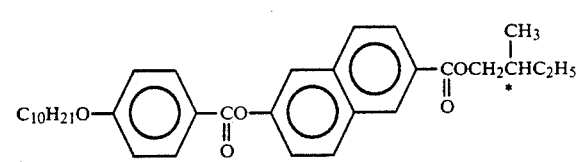 (47)

-continued
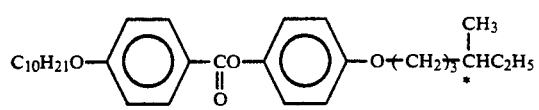
(48)
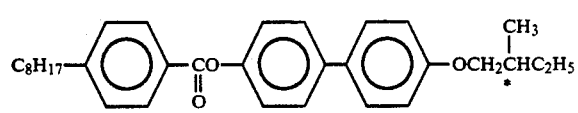
(49)
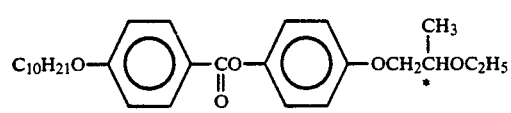
(50)
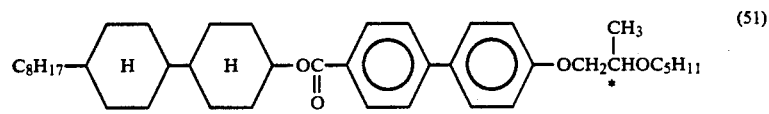
(51)
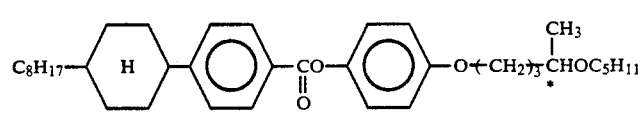
(52)
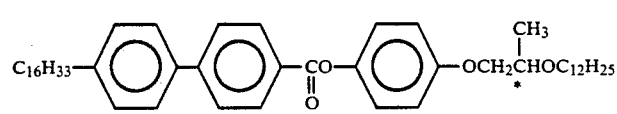
(53)
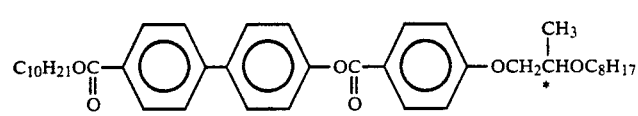
(54)
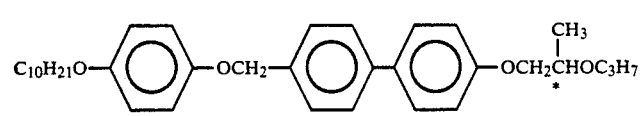
(55)
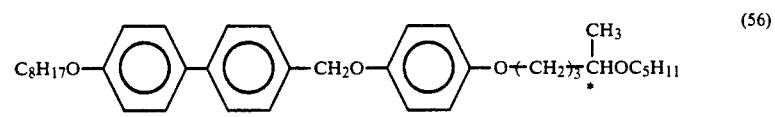
(56)
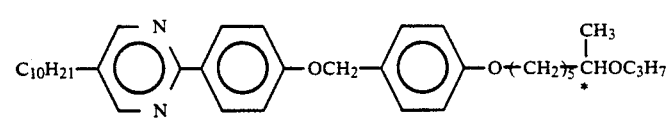
(57)
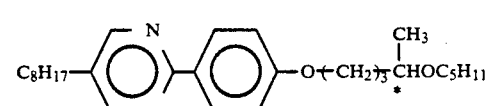
(58)
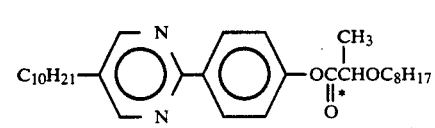
(59)
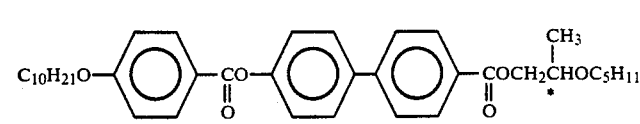
(60)

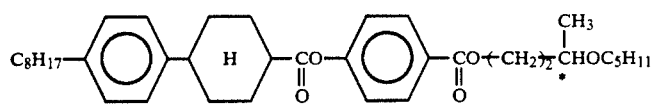 (61)
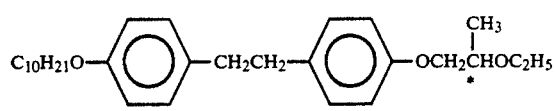 (62)
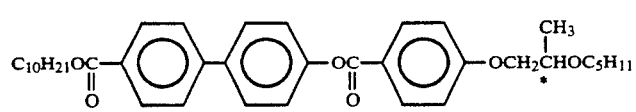 (63)
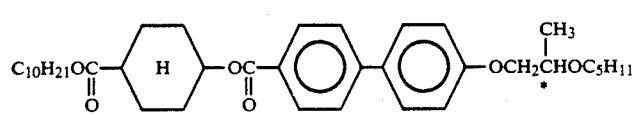 (64)
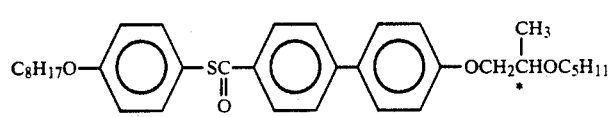 (65)
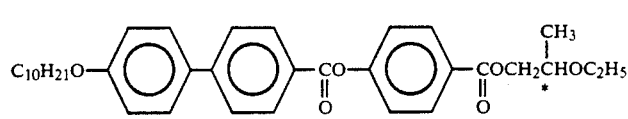 (66)
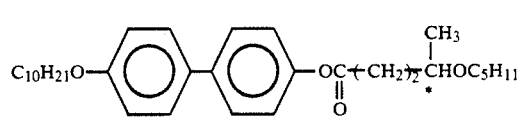 (67)
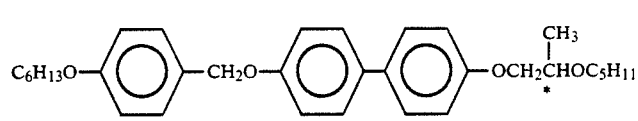 (68)
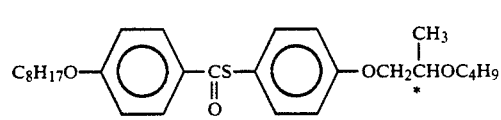 (69)
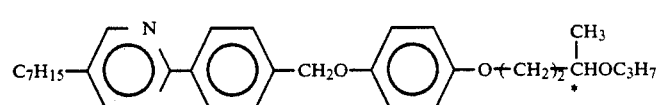 (70)
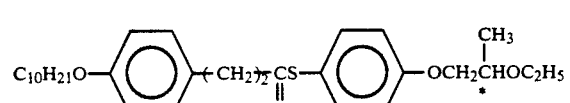 (71)
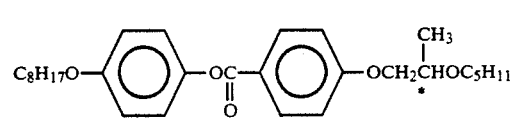 (72)
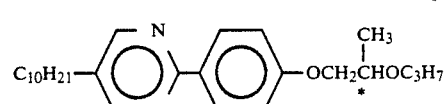 (73)

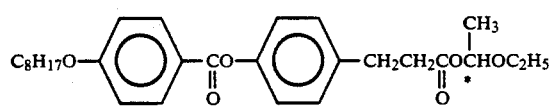 (74)
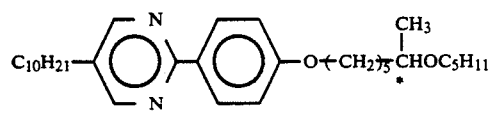 (75)
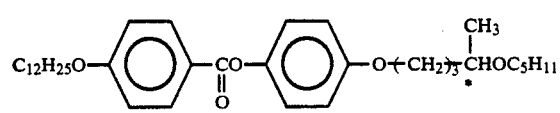 (76)
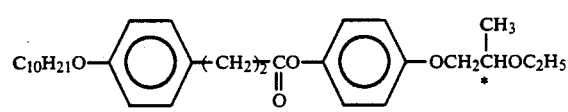 (77)
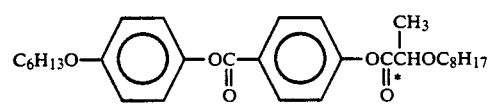 (78)
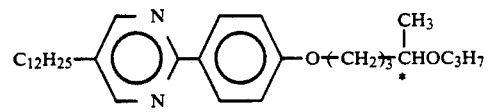 (79)
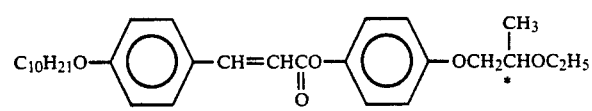 (80)
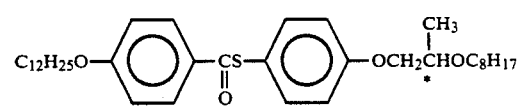 (81)
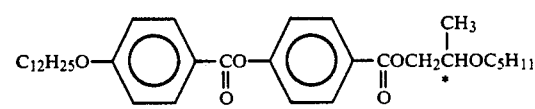 (82)
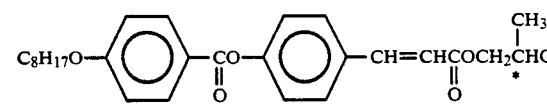 (83)
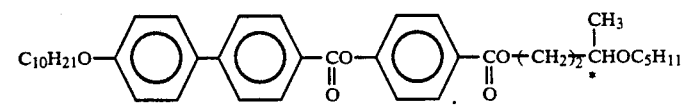 (84)
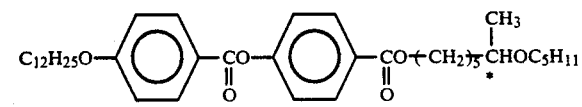 (85)
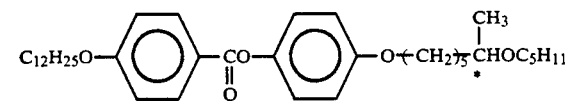 (86)

-continued
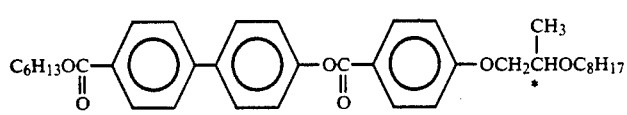 (87)
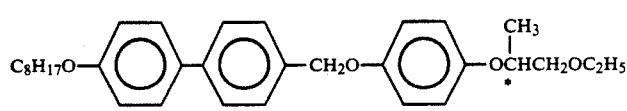 (88)
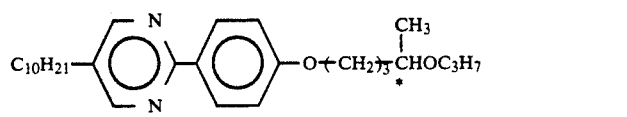 (89)
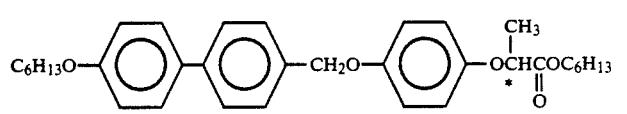 (90)
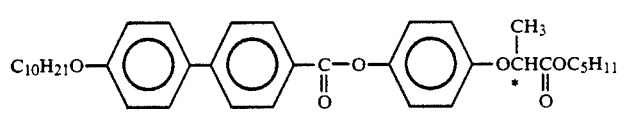 (91)
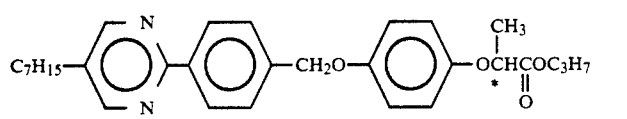 (92)
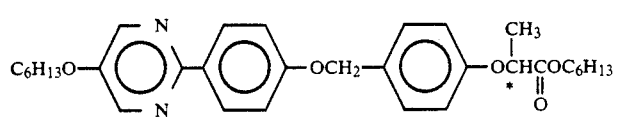 (93)
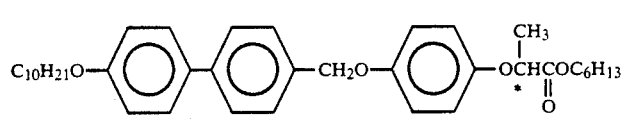 (94)
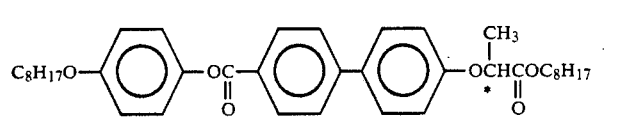 (95)
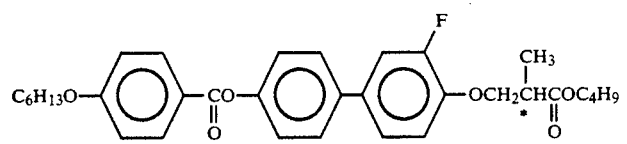 (96)
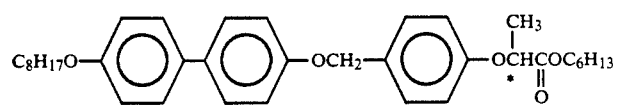 (97)
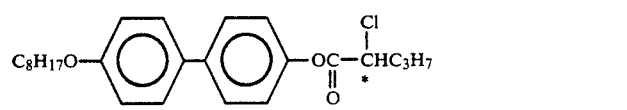 (98)
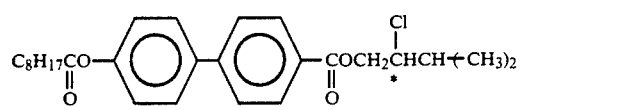 (99)

-continued
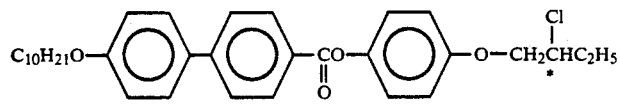 (100)
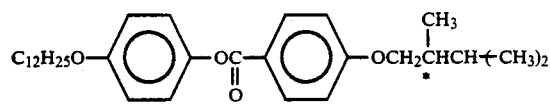 (101)
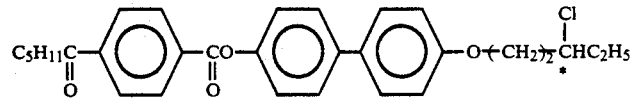 (102)
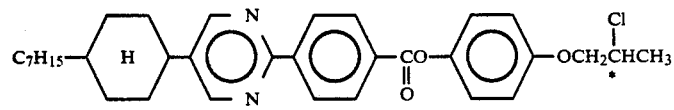 (103)
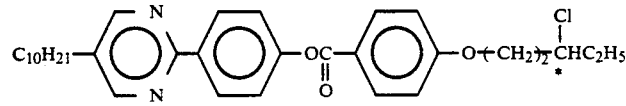 (104)
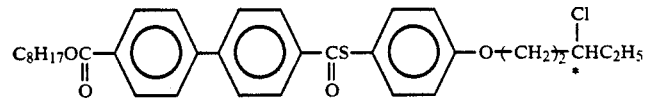 (105)
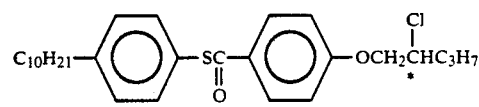 (106)
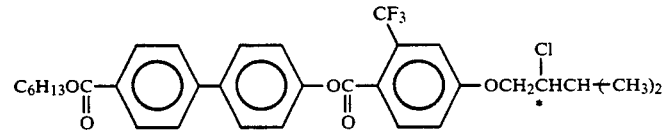 (107)
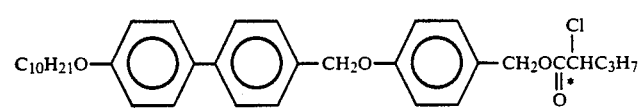 (108)
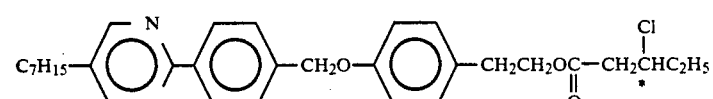 (109)
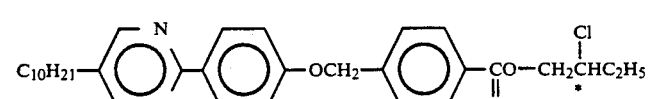 (110)
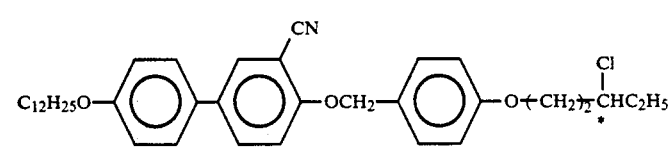 (111)
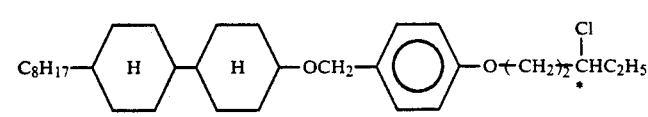 (112)

-continued
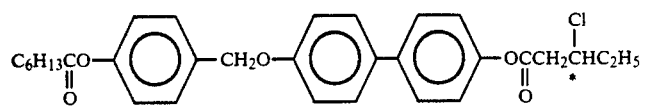 (113)
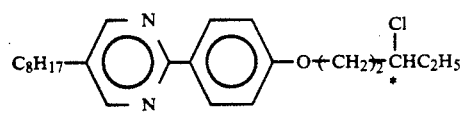 (114)
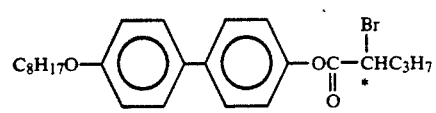 (115)
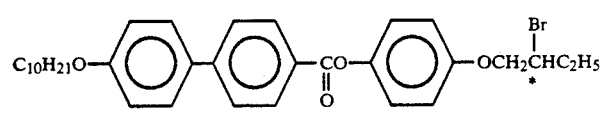 (116)
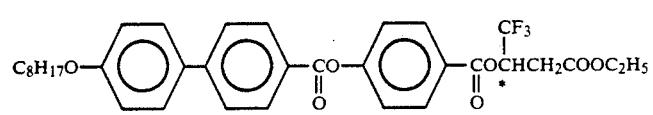 (117)
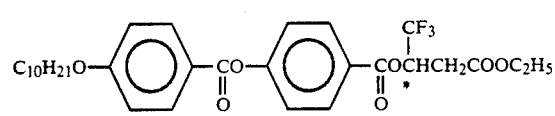 (118)
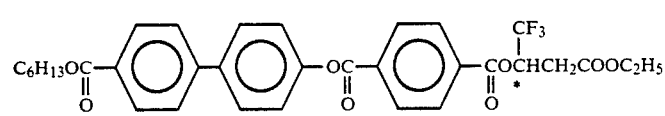 (119)
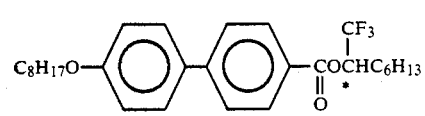 (120)
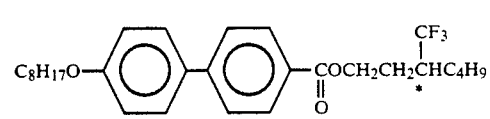 (121)
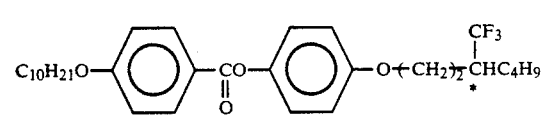 (122)
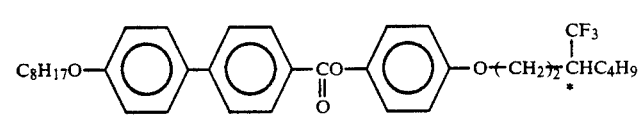 (123)
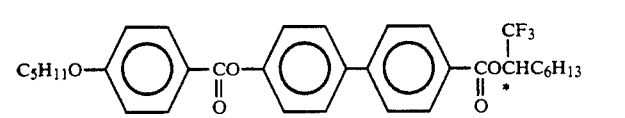 (124)
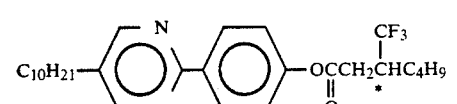 (125)

-continued
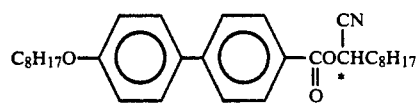 (126)
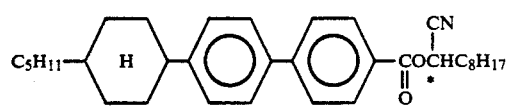 (127)
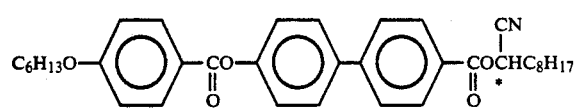 (128)
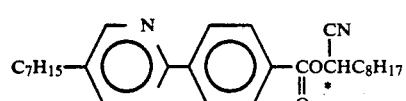 (129)
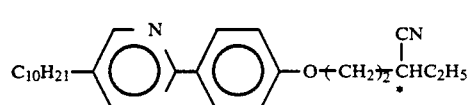 (130)
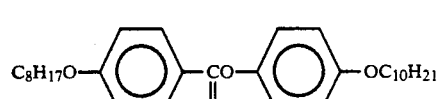 (131)
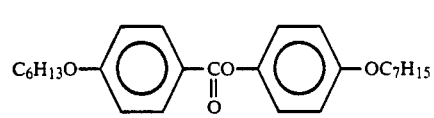 (132)
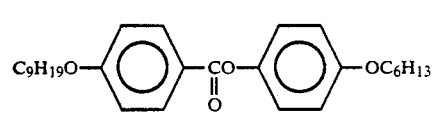 (133)
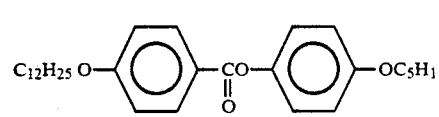 (134)
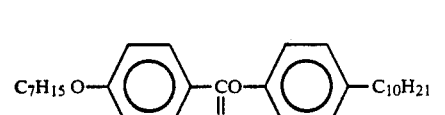 (135)
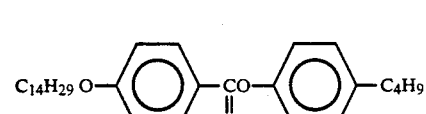 (136)
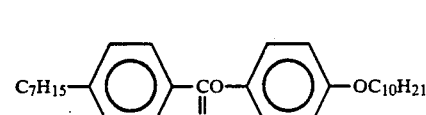 (137)
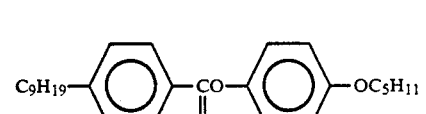 (138)

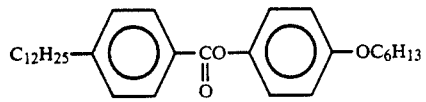 (139)
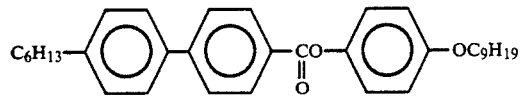 (140)
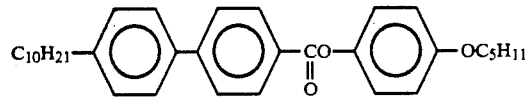 (141)
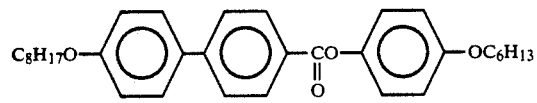 (142)
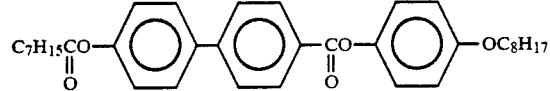 (143)
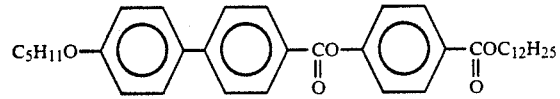 (144)
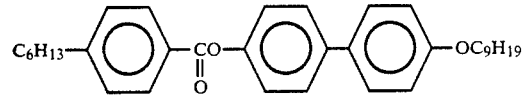 (145)
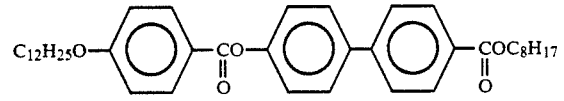 (146)
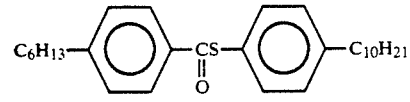 (147)
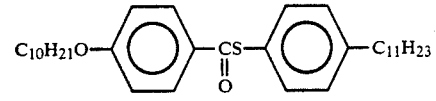 (148)
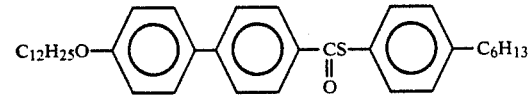 (149)
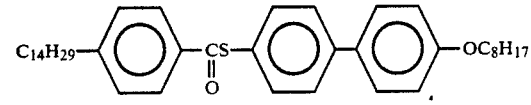 (150)
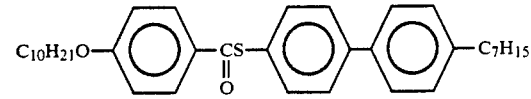 (151)

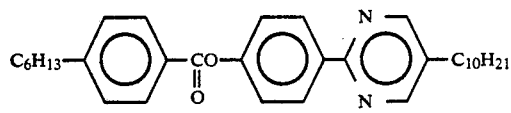 (152)
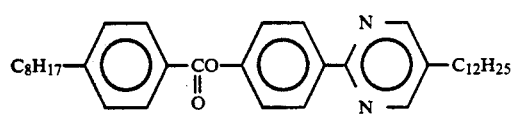 (153)
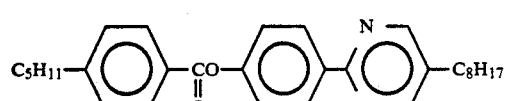 (154)
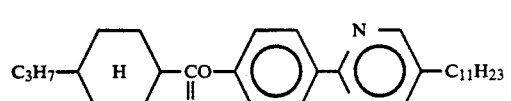 (155)
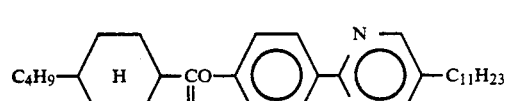 (156)
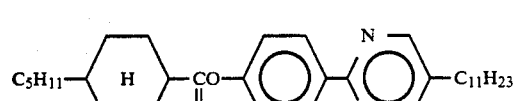 (157)
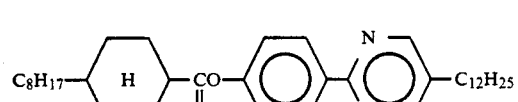 (158)
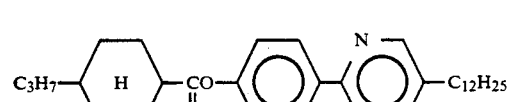 (159)
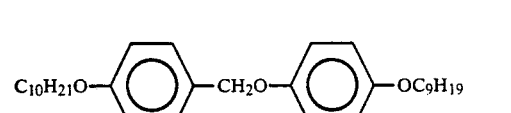 (160)
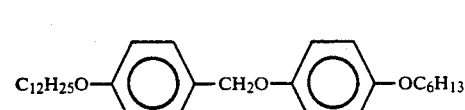 (161)
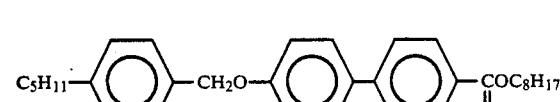 (162)
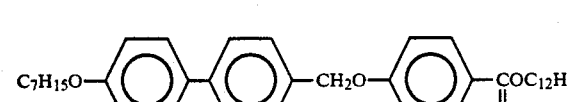 (163)
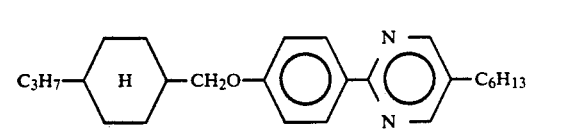 (164)

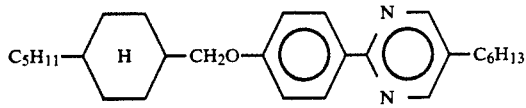

(165)

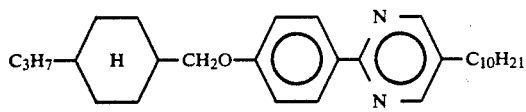

(166)

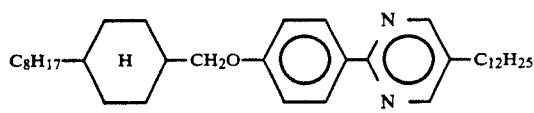

(167)

In formulating the liquid crystal composition according to the present invention comprising a mesomorphic compound represented by the formula (I) together with another mesomorphic compound, it is desirable to mix 1-300 wt. parts, preferably 2-200 wt. parts, of a mesomorphic compound of the formula (I) with 100 wt. parts of the remainder of the liquid crystal composition other than the compound of the formula (I).

Further, when two or more species of the compounds represented by the formula (I) are used, the two or more species of the compounds of the formula (I) may be used in a total amount of 1-500 wt. parts, preferably 2-200 wt. parts, per 100 wt. parts of the remainder of the liquid crystal composition other than the compound of the formula (I).

In formulating the liquid crystal composition according to the present invention comprising mesomorphic compounds represented by the formula (I) and either (II) or (III) together with another mesomorphic compound, it is desirable to mix 1-300 wt. parts each, preferably 2-200 wt. parts each, of mesomorphic compound of the formulas (I) and either (II) or (III) with 100 wt. parts of the remainder of the liquid crystal composition other than the compounds of the formulas (I), (II) and (III).

Further, when two or more species of either one or both of the compounds represented by the formulas (I) and either (II) or (III) are used, the two or more species of the compounds of the formulas (I) and either (II) or (III) may be used in a total amount of 1-500 wt. parts, preferably 2-200 wt. parts, per 100 wt. parts of the remainder of the liquid crystal composition other than the compounds of the formulas (I), (II) and (III).

In formulating the liquid crystal composition according to the present invention comprising mesomorphic compounds represented by the formulas (I), (II) and (III) together with another mesomorphic compound, it is desirable to mix 1-300 wt. parts each, preferably 2-200 wt. parts each, of mesomorphic compounds of the formulas (I), (II) and (III) with 100 wt. parts of the remainder of the liquid crystal composition other than the compounds of the formulas (I), (II) and (III).

Further, when two or more species of either one or two or all of the compounds represented by the formulas (I), (II) and (III) are used, the two or more species of the compounds of the formulas (I), (II) and (III) may be used in a total amount of 1-500 wt. parts, preferably 2-200 wt. parts, per 100 wt. parts of the remainder of the liquid crystal composition other than the compound of the formulas (I), (II) and (III).

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 50 Å-1 micron, preferably 100-3000 Å, further preferably 100-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
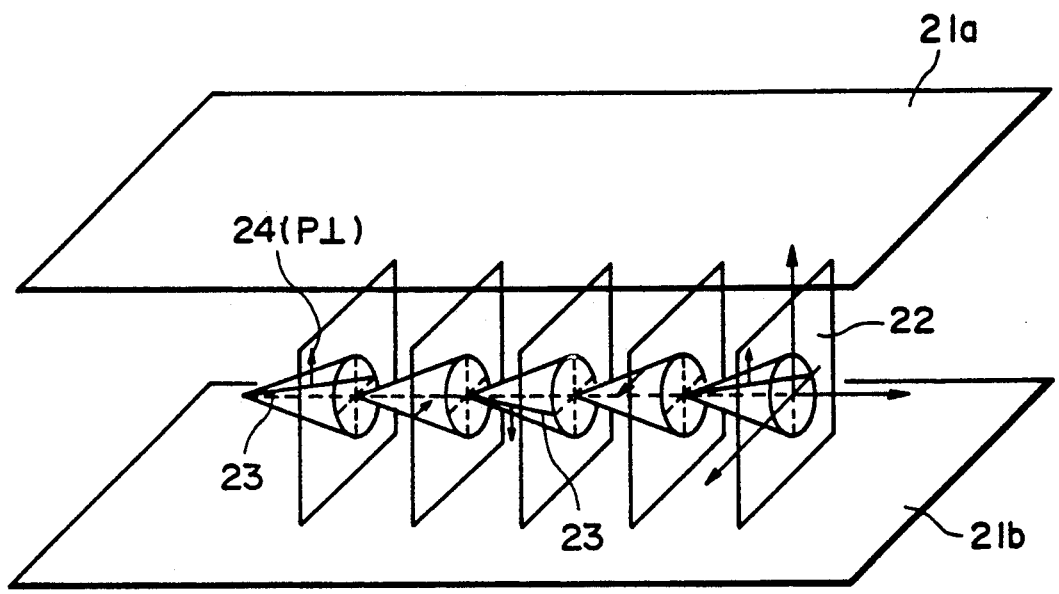
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal 23 so that the dipole moments (P⊥) 24 are all molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
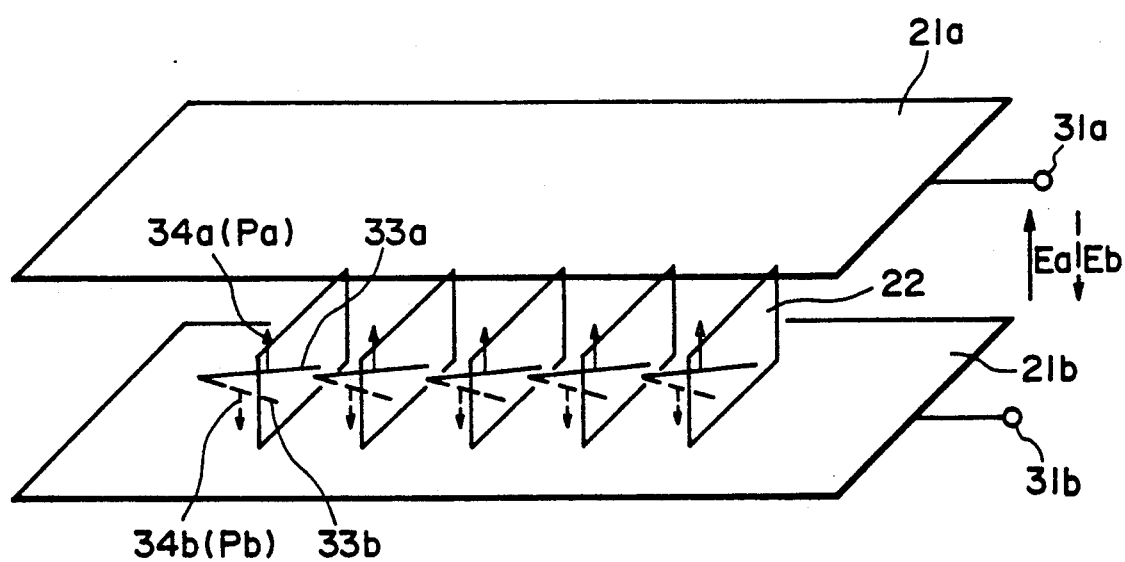

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

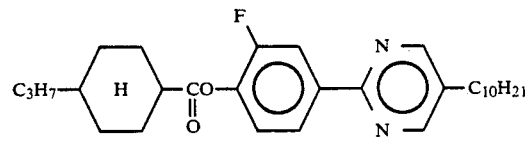

2-fluoro-4-(5-decyl-2-pyrimidinyl)phenyl trans-4-n-propylcyclohexylcarboxylate (Example Compound No. 1-2) represented by the above formula was synthesized in the following manner.

0.50 g (1.52 mM) of 2-fluoro-4-(5-decyl-2-pyrimidinyl)phenol was dissolved in 10 ml of pyridine and stirred on an iced water bath. To the solution, 0.34 g (1.82 mM) of trans-4-n-propylcyclohexanecarbonyl chloride was added dropwise, followed by stirring for 5 hours on the iced water bath. After the reaction, the reaction mixture was poured into water, acidified with conc. hydrochloric acid and extracted with methylene chloride. The organic layer was washed with water, followed by drying with sodium sulfate, distilling-off of the solvent, purification by silica gel column chromatography and recrystallization from ethanol/ethyl acetate mixture solvent to obtain 0.44 g (0.92 mM) of the objective compound (Yield: 60.3%).

Phase transition temperature (° C.)

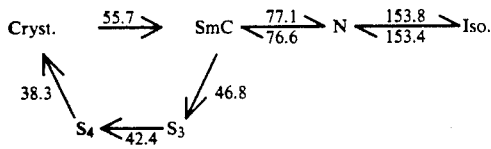

N: nematic phase.

EXAMPLE 2

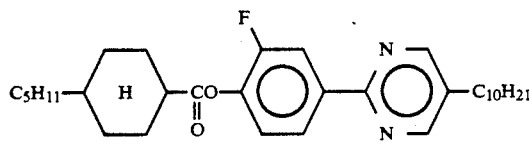

2-fluoro-4-(5-decyl-2-pyrimidinyl)phenyl trans-4-n-pentylcyclohexylcarboxylate (Example Compound No. 1-8) represented by the above formula was synthesized in the following manner.

0.39 g (1.80 mM) of trans-4-n-pentylcyclo-hexylcarbonyl chloride was added dropwise to 0.50 g (1.52 mM) of 2-fluoro-4-(5-decyl-2-pyrimidinyl)phenyl dissolved in 4 ml of pyridine on an iced bath. After the addition, the iced water bath was removed and the resultant mixture was stirred for 30 min. at room temperature, followed by further stirring for 2 hours at 40°–50 °C. on a water bath. After the reaction, the reaction mixture was poured into 100 ml of iced water to precipitate a crystal. The crystal was recovered by filtration and dissolved in ethyl acetate, followed by washing with 2N-hydrochloric acid and water, drying with sodium sulfate and distilling-off of the solvent. The resultant crystal was purified by silica gel column chromatography (eluent: toluene) and recrystallized from ethanol in a freezer to obtain 0.45 g (0.88 mM) of the objective compound (Yield: 58.2%).

Phase transition temperature (° C.)

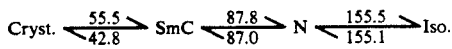

EXAMPLE 3

A liquid crystal compound A was prepared by mixing the following compounds in respectively indicated proportions.

| Ex. Comp. No. | Structural formula | wt. parts |
| --- | --- | --- |
| 20 | $C_{10}H_{21}O$—[pyrimidinyl]—[phenyl]—O(CH$_2$)$_{\overline{3}}$*CH(CH$_3$)C$_2$H$_5$ | 15 |
| 21 | $C_8H_{17}$—[pyrimidinyl]—[phenyl]—O(CH$_2$)$_{\overline{3}}$*CH(CH$_3$)C$_2$H$_5$ | 15 |
| 58 | $C_8H_{17}$—[pyrimidinyl]—[phenyl]—O(CH$_2$)$_{\overline{3}}$*CH(CH$_3$)OC$_5$H$_{11}$ | 10 |
| 89 | $C_{10}H_{21}$—[pyrimidinyl]—[phenyl]—O(CH$_2$)$_{\overline{3}}$*CH(CH$_3$)OC$_3$H$_7$ | 20 |
| 159 | $C_3H_7$—[cyclohexyl-H]—CO·O—[phenyl]—[pyrimidinyl]—C$_{12}$H$_{25}$ | 15 |
| 165 | $C_5H_{11}$—[cyclohexyl-H]—CH$_2$O—[phenyl]—[pyrimidinyl]—C$_6$H$_{13}$ | 5 |
| 3-69 | $C_{10}H_{21}$—[pyrimidinyl]—[phenyl]—OC(=O)—[phenyl-F]—OCH$_2$*CHC$_6$H$_{13}$ | 13 |

| Ex. Comp. No. | Structural formula | wt. parts |
|---|---|---|
| 3-94 |  | 7 |

The liquid crystal composition A was further mixed with Example Compound No. 1-2 in the proportions indicated below to provide a liquid crystal composition B.

| Ex. Comp. No. | Structural formula | wt. parts |
|---|---|---|
| 1-2 | 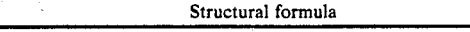 | 5 |
| | Composition A | 90 |

Two 0.7 mm-thick glass plates were provided and respectively coated with an ITO (film to form an electrode for voltage application, which was further coated with an insulating layer of vapor-deposited $SiO_2$. On the insulating layer, a 0.2% solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum under the application of a peak-to-peak voltage Vpp of 20 V in combination with right-angle cross-nicol polarizers).

The results are shown below.

| | 15° C. | 25° C. | 35° C. |
|---|---|---|---|
| Response time (μsec) | 134 | 89 | 74 |

Further, when the device was driven and a clear switching action was observed, and good bistability was shown after the termination of the voltage application.

COMPARATIVE EXAMPLE 1

A ferroelectric liquid crystal device was prepared in the same manner as in Example 3 except that the liquid crystal composition A prepared in Example 3 was injected into a cell. The measured values of the response time of the device were as follows.

| | 15° C. | 25° C. | 35° C. |
|---|---|---|---|
| Response time (μsec) | 155 | 100 | 80 |

As is understood from the comparison between Example 3 and Comparative Example 1, a ferroelectric liquid crystal device using the liquid crystal composition B containing the mesomorphic compound according to the present invention showed an improved low-temperature operation characteristic, a high response speed and a decreased temperature-dependence of the response speed.

EXAMPLE 4

A liquid crystal composition C was prepared in the same manner as in Example 3 except that the following Example Compounds were used instead of Example Compound No. 1-2 in respectively indicated proportions.

| Ex. Comp. No. | Structural formula | wt. parts |
|---|---|---|
| 1-8 | ![structure: C5H11-H-CO-O-(F-phenyl)-(pyrimidine N)-C10H21] | 5 |

| Ex. Comp. No. | Structural formula | wt. parts |
|---|---|---|
| 1-37 | 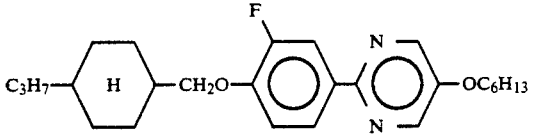 | 5 |
| | Composition A | 90 |

A ferroelectric liquid crystal device was prepared in the same manner as in Example 3 except for using the composition C. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 132 | 88 | 72 |

Further, when the device was driven, a clear switching action was observed, and good bistability was shown after the termination of the voltage application.

As is understood from the comparison between Example 4 and Comparative Example 1, a ferroelectric liquid crystal device using the liquid crystal composition C containing the mesomorphic compound according to the present invention showed an improved low-temperature operation characteristic, a high response speed and a decreased temperature-dependence of the response speed.

EXAMPLE 5

A liquid crystal composition D was prepared in the same manner as in Example 3 except that the following Example Compounds were used instead of Example Compound No. 1-2 in respectively indicated proportions.

A ferroelectric liquid crystal device was prepared in the same manner as in Example 3 except for using the composition D. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 128 | 86 | 71 |

Further, when the device was driven, a clear switching action was observed, and good bistability was shown after the termination of the voltage application.

As is understood from the comparison between Example 5 and Comparative Example 1, a ferroelectric liquid crystal device using the liquid crystal composition D containing the mesomorphic compound according to the present invention showed an improved low-temperature operation characteristic, a high response speed and a decreased temperature-dependence of the response speed.

EXAMPLE 6

A liquid crystal composition E was prepared in the same manner as in Example 3 except that the following Example Compounds were used instead of Compound No. 1-2 in respectively indicated proportions.

| Ex. Comp. No. | Structural formula | wt. parts |
|---|---|---|
| 1-17 | 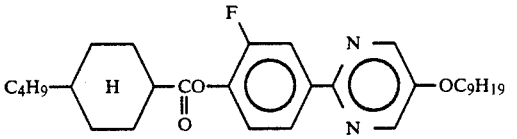 | 3 |
| 1-61 | 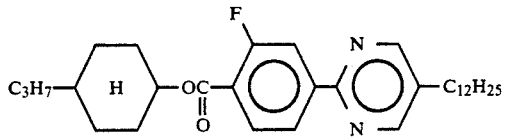 | 3 |
| 1-45 | 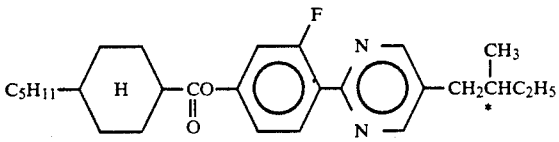 | 4 |
| | Composition A | 90 |

| Ex. Comp. No. | Structural formula | wt. parts |
|---|---|---|
| 1-11 | $C_6H_{13}$—[H]—CO—O—[phenyl(CN)]—[pyrimidine]—$C_{10}H_{21}$ | 4 |
| 1-49 | $C_6H_{13}$—[H]—CO—O—[phenyl(F)]—[pyrimidine]—$OCH_2\overset{*}{C}H(F)C_6H_{13}$ | 3 |
| 1-55 | $C_5H_{11}$—[H]—$CH_2O$—[phenyl(F)]—[pyrimidine]—$OCH_2\overset{*}{C}H(CH_3)C_2H_5$ | 3 |
| Composition A | | 90 |

A ferroelectric liquid crystal device was prepared in the same manner as in Example 3 except for using the composition E. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 119 | 79 | 65 |

Further, when the device was driven, a clear switching action was observed, and good bistability was shown after the termination of the voltage application.

As is understood from the comparison between Example 6 and Comparative Example 1, a ferroelectric liquid crystal device using the liquid crystal composition E containing the mesomorphic compound according to the present invention showed an improved low-temperature operation characteristic, a high response speed and a decreased temperature-dependence of the response speed.

EXAMPLE 7

A liquid crystal composition F was prepared in the same manner as in Example 3 except that the following Example Compounds were used instead of Example Compound No. 1-2 in respectively indicated proportions.

| Ex. Comp. No. | Structural formula | wt. parts |
|---|---|---|
| 1-20 | $C_5H_{11}$—[H]—CO—O—[phenyl(F)]—[pyrimidine]—$OC_{12}H_{25}$ | 4 |
| 1-72 | $C_4H_9$—[H]—O—CO—[phenyl(F)]—[pyrimidine]—$OC_{12}H_{25}$ | 4 |
| 1-80 | $C_3H_7$—[H]—$OCH_2$—[phenyl(CN)]—[pyrimidine]—$C_{10}H_{21}$ | 2 |
| Composition A | | 90 |

A ferroelectric liquid crystal device was prepared in the same manner as in Example 3 except for using the composition F. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 131 | 90 | 71 |

Further, when the device was driven, a clear switching action was observed, and good bistability was shown after the termination of the voltage application.

As is understood from the comparison between Example 7 and Comparative Example 1, a ferroelectric liquid crystal device using the liquid crystal composition F containing the mesomorphic compound according to the present invention showed an improved low-temperature operation characteristic, a high response speed and a decreased temperature-dependence of the response speed.

EXAMPLE 8

A liquid crystal composition G was prepared in the same manner as in Example 3 except that the following Example Compounds were used instead of Example Compound No. 1-2 in respectively indicated proportions.

| Ex. Comp. No. | Structural formula | wt. parts |
| --- | --- | --- |
| 1-26 | $C_4H_9$—H—CO—(F)—(N,N)—$COC_{12}H_{25}$ | 3 |
| 1-32 | $C_4H_9$—H—$CH_2O$—($CH_3$)—(N,N)—$C_{12}H_{25}$ | 3 |
| 1-84 | $C_4H_9$—H—$OCH_2$—(F)—(N,N)—$OC_8H_{17}$ | 3 |
| | Composition A | 91 |

A ferroelectric liquid crystal device was prepared in the same manner as in Example 3 except for using the composition G. The ferroelectric liquid crystal device was subjected to measurement of response time and observation of a switching state, etc. in the same manner as in Example 3, whereby the following results were obtained.

| | 15° C. | 25° C. | 35° C. |
| --- | --- | --- | --- |
| Response time (μsec) | 131 | 89 | 70 |

Further, when the device was driven, a clear switching action was observed, and good bistability was shown after the termination of the voltage application.

As is understood from the comparison between Example 8 and Comparative Example 1, a ferroelectric liquid crystal device using the liquid crystal composition G containing the mesomorphic compound according to the present invention showed an improved low-temperature operation characteristic, a high response speed and a decreased temperature-dependence of the response speed.

EXAMPLE 9

A liquid crystal composition H was prepared by mixing the following compounds in respectively indicated proportions.

| Ex. Comp. No. | Structural formula | wt. parts |
| --- | --- | --- |
| 8 | $C_8H_{17}O$—(◯)—OC(=O)—(◯)—(◯)—$CH_2CHC_2H_5$ ($CH_3$) * | 16 |
| 9 | $C_8H_{17}O$—(◯)—CS(=O)—(◯)—$CH_2CHC_2H_5$ ($CH_3$) * | 22.5 |
| 18 | $C_8H_{17}O$—(◯)—CO—(◯)—$OCH_2CHC_2H_5$ ($CH_3$) * | 64 |
| 23 | $C_8H_{17}O$—(N,N)—(◯)—$O(CH_2)_3CHC_2H_5$ ($CH_3$) * | 10 |

-continued

| Ex. Comp. No. | Structural formula | wt. parts |
|---|---|---|
| 24 | $C_{11}H_{23}$—[pyrazine]—[phenyl]—O(CH$_2$)$_2$CH(CH$_3$)C$_2$H$_5$ * | 10 |
| 43 | $C_{10}H_{21}$O—[phenyl]—C(=S)(O)—[phenyl]—OCH$_2$CH(CH$_3$)C$_2$H$_5$ * | 22.5 |
| 63 | $C_{10}H_{21}$OC(O)—[phenyl]—[phenyl]—OC(O)—[phenyl]—OCH$_2$CH(CH$_3$)OC$_5$H$_{11}$ * | 15 |
| 87 | $C_6H_{13}$OC(O)—[phenyl]—[phenyl]—OC(O)—[phenyl]—OCH$_2$CH(CH$_3$)OC$_8$H$_{17}$ * | 15 |
| 159 | $C_3H_7$—[cyclohexyl-H]—C(O)O—[phenyl]—[pyrazine]—C$_{12}$H$_{25}$ | 20 |
| 3-13 | $C_{12}H_{25}$O—[phenyl]—C(O)O—[phenyl]—OCH$_2$CH(F)C$_6$H$_{13}$ * | 6.75 |
| 3-7 | $C_8H_{17}$O—[phenyl]—C(O)O—[phenyl]—OCH$_2$CH(F)C$_5$H$_{11}$ * | 18.75 |

The liquid crystal composition H was further mixed with Example Compounds Nos. 1-2, 1-16 and 1-34 in the proportions indicated below to provide a liquid crystal composition I.

was subjected to measurement of response time and observation of a switching state, etc. in the same manner as in Example 3, whereby the following results were obtained.

| Ex. Comp. No. | Structural formula | wt. parts |
|---|---|---|
| 1-2 | $C_3H_7$—[cyclohexyl-H]—C(O)O—[phenyl-F]—[pyrazine]—C$_{10}$H$_{21}$ | 4 |
| 1-16 | $C_3H_7$—[cyclohexyl-H]—C(O)O—[phenyl-F]—[pyrazine]—OC$_{12}$H$_{25}$ | 3 |
| 1-34 | $C_5H_{11}$—[cyclohexyl-H]—CH$_2$O—[phenyl-F]—[pyrazine]—C$_7$H$_{15}$ | 3 |
| Composition H | | 90 |

A ferroelectric liquid crystal device was prepared in the same manner as in Example 3 except for using the composition I. The ferroelectric liquid crystal device

| | 15° C. | 25° C. | 35° C. |
|---|---|---|---|
| Response time (μsec) | 390 | 251 | 192 |

COMPARATIVE EXAMPLE 2

A ferroelectric liquid crystal device was prepared in the same manner as in Example 3 except that the liquid crystal composition H prepared in Example 9 was injected into a cell. The measured values of the response time of the device were as follows.

| | 15° C. | 25° C. | 35° C. |
|---|---|---|---|
| Response time (μsec) | 450 | 270 | 195 |

As is understood from the comparison between Example 9 and Comparative Example 2, a ferroelectric liquid crystal device using the liquid crystal composition I containing the mesomorphic compound according to the present invention showed an improved low-temperature operation characteristic, a high response speed and a decreased temperature-dependence of the response speed.

EXAMPLE 10

A liquid crystal composition J was prepared in the same manner as in Example 9 except that the following Example Compounds were used instead of Example Compounds Nos. 1-2, 1-16 and 1-34 prepared in Example 9 in respectively indicated proportions.

A ferroelectric liquid crystal device was prepared in the same manner as in Example 3 except for using the composition J. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 395 | 242 | 183 |

Further, when the device was driven, a clear switching action was observed, and good bistability was shown after the termination of the voltage application.

As is understood from the comparison between Example 10 and Comparative Example 2, a ferroelectric liquid crystal device using the liquid crystal composition J containing the mesomorphic compound according to the present invention showed an improved low-temperature operation characteristic, a high response speed and a decreased temperature-dependence of the response speed.

EXAMPLE 11

A liquid crystal composition K was prepared in the same manner as in Example 9 except that the following Example Compounds were used instead of Example Compounds Nos. 1-2, 1-16 and 1-34 prepared in Example 9 in respectively indicated proportions.

| Ex. Comp. No. | Structural formula | wt. parts |
|---|---|---|
| 1-6 | $C_4H_9$—⟨H⟩—CO-O—⟨Cl-phenyl⟩—⟨pyrimidine⟩—$C_{10}H_{21}$ | 3 |
| 1-33 | $C_5H_{11}$—⟨H⟩—$CH_2$O—⟨Cl-phenyl⟩—⟨pyrimidine⟩—$C_6H_{13}$ | 4 |
| 1-64 | $C_4H_9$—⟨H⟩—O-CO—⟨Br-phenyl⟩—⟨pyrimidine⟩—$C_9H_{19}$ | 3 |
| Composition H | | 90 |

| Ex. Comp. No. | Structural formula | wt. parts |
|---|---|---|
| 1-48 | $C_5H_{11}$—⟨H⟩—CO-O—⟨F-phenyl⟩—⟨pyrimidine⟩—O-(-$CH_2$-)$_{\overline{2}}$CH(CH$_3$)OCH$_3$ | 3 |

-continued

| Ex. Compd. No. | Structural formula | wt. parts |
|---|---|---|
| 1-53 | C₅H₁₁—⟨H⟩—CH₂O—⟨F⟩—⟨N,N⟩—(CH₂)₄*CH(CH₃)C₂H₅ | 3 |
| 1-71 | C₃H₇—⟨H*⟩—OC(O)—⟨F⟩—⟨N,N⟩—OCH₂*CHFC₆H₁₃ | 4 |
| | Composition H | 90 |

A ferroelectric liquid crystal device was prepared in the same manner as in Example 3 except for using the composition K. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 388 | 241 | 185 |

Further, when the device was driven, a clear switching action was observed, and good bistability was shown after the termination of the voltage application.

As is understood from the comparison between Example 11 and Composition Example 2, a ferroelectric liquid crystal device using the liquid crystal composition K containing the mesomorphic compound according to the present invention showed an improved low-temperature operation characteristic, a high response speed and a decreased temperature-dependence of the response speed.

EXAMPLE 12

A liquid crystal composition L was prepared is the same manner as in Example 9 except that the following Example Compounds were used instead of Example Compounds Nos. 1-2, 1-16, and 1-34 prepared in Example 9 in respectively indicated proportions.

| Ex. Comp. No. | Structural formula | wt. parts |
|---|---|---|
| 1-4 | C₃H₇—⟨H⟩—CO(O)—⟨F⟩—⟨N,N⟩—C₆H₁₃ | 2 |
| 1-8 | C₅H₁₁—⟨H⟩—CO(O)—⟨F⟩—⟨N,N⟩—C₁₀H₂₁ | 2 |
| 1-49 | C₆H₁₃—⟨H⟩—CO(O)—⟨F⟩—⟨N,N⟩—OCH₂*CHFC₆H₁₃ | 3 |
| 1-63 | C₄H₉—⟨H⟩—OC(O)—⟨F⟩—⟨N,N⟩—C₈H₁₇ | 2 |
| 1-86 | C₅H₁₁—⟨H⟩—OCH₂—⟨CH₃⟩—⟨N,N⟩—OC₆H₁₃ | 2 |

| Ex. Comp. No. | Structural formula | wt. parts |
|---|---|---|
| | Composition H | 89 |

A ferroelectric liquid crystal device was prepared in the same manner as in Example 3 except for using the composition L. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 366 | 244 | 187 |

Further, when the device was driven, a switching action was observed, and good bistability was shown after the termination of the voltage application.

As is understood from the comparison between Example 12 and Comparative Example 2, a ferroelectric liquid crystal device using the liquid crystal composition L containing the mesomorphic compound according to the present invention showed an improved low-temperature operation characteristic, a high response speed and a decreased temperature-dependence of the response speed.

EXAMPLE 13

A liquid crystal composition M was prepared in the same manner as in Example 9 except that the following Example Compounds were used instead of Example Compounds Nos. 1-2, 1-16 and 1-34 prepared in Example 9 in respectively indicated proportions.

A ferroelectric liquid crystal device was prepared in the same manner as in Example 3 except for using the composition M. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 374 | 274 | 190 |

Further, when the device was driven, a clear switching action was observed, and good bistability was shown after the termination of the voltage application.

As is understood from the comparison between Example 13 and Comparative Example 2, a ferroelectric liquid crystal device using the liquid crystal composition M containing the mesomorphic compound according to the present invention showed an improved low-temperature operation characteristic, a high response speed and a decreased temperature-dependence of the response speed.

EXAMPLE 14

A liquid crystal composition N was prepared in the same manner as in Example 9 except that the following Example Compounds were used instead of Example Compounds Nos. 1-2, 1-16 and 1-34 prepared in Example 9 in respectively indicated proportions.

| Ex. Comp. No. | Structural formula | wt. parts |
|---|---|---|
| 1-1 | CH$_3$—⟨H⟩—CO—O—⟨F⟩—⟨N⟩—C$_8$H$_{17}$ | 4 |
| 1-41 | C$_4$H$_9$—⟨H⟩—CH$_2$O—⟨F⟩—⟨N⟩—COC$_6$H$_{13}$ | 2 |
| 1-57 | C$_4$H$_9$—⟨H⟩—CH$_2$O—⟨F⟩—⟨N⟩—OCH$_2$CHC$_8$H$_{17}$ (with F, *) | 3 |
| 1-66 | C$_5$H$_{11}$—⟨H⟩—OCO—⟨F⟩—⟨N⟩—(CH$_2$)$_3$CHC$_2$H$_5$ (with CH$_3$, *) | 2 |
| | Composition H | 89 |

| Ex. Comp. No. | Structural formula | wt. parts |
|---|---|---|
| 1-2 | $C_3H_7$—[H]—CO-O—[F-phenyl]—[pyridine(N,N)]—$C_{10}H_{21}$ | 4 |
| 1-7 | $C_5H_{11}$—[H]—CO-O—[F-phenyl]—[pyridine(N,N)]—$C_8H_{17}$ | 2 |
| 1-38 | $C_3H_7$—[H]—$CH_2O$—[Br-phenyl]—[pyridine(N,N)]—$OC_{10}H_{21}$ | 2 |
| 1-54 | $C_6H_{13}$—[H]—$CH_2O$—[F-phenyl]—[pyridine(N,N)]—$(CH_2)_{\overline{4}}CH(CH_3)CH_3$ | 2 |
| 1-87 | $C_8H_{17}$—[H]—$OCH_2$—[F-phenyl]—[pyridine(N,N)]—$OCH_2C^*H(F)C_4H_9$ | 3 |
| | Composition H | 87 |

A ferroelectric liquid crystal device was prepared in the same manner as in Example 3 except for using the composition N. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 364 | 244 | 186 |

Further, when the device was driven, a clear switching action was observed, and good bistability was shown after the termination of the voltage application.

As is understood from the comparison between Example 14 and Comparative Example 2, a ferroelectric liquid crystal device using the liquid crystal composition N containing the mesomorphic compound according to the present invention showed an improved low-temperature operation characteristic, a high response speed and a decreased temperature-dependence of the response speed.

EXAMPLE 15

A liquid crystal composition O was prepared in the same manner as in Example 9 except that the following Example Compounds were used instead of Example Compounds Nos. 1-2, 1-16 and 1-34 prepared in Example 9 in respectively indicated proportions.

| Ex. Comp. No. | Structural formula | wt. parts |
|---|---|---|
| 1-49 | $C_6H_{13}$—[H]—CO-O—[F-phenyl]—[pyridine(N,N)]—$OCH_2C^*H(F)C_6H_{13}$ | 4 |
| 1-71 | $C_3H_7$—[H]—CO-O—[F-phenyl]—[pyridine(N,N)]—$OCH_2C^*H(F)C_6H_{13}$ | 4 |

| Ex. Comp. No. | Structural formula | wt. parts |
|---|---|---|
| | Composition H | 92 |

A ferroelectric liquid crystal device was prepared in the same manner as in Example 3 except for using the composition O. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 315 | 203 | 152 |

Further, when the device was driven, a clear switching action was observed, and good bistability was shown after the termination of the voltage application.

As is understood from the comparison between Example 15 and Comparative Example 2, a ferroelectric liquid crystal device using the liquid crystal composition O containing the mesomorphic compound according to the present invention showed an improved low-temperature operation characteristic, a high response speed and a decreased temperature-dependence of the response speed.

EXAMPLE 16

A liquid crystal composition P was prepared in the same manner as in Example 9 except that the following Example Compounds were used instead of Example Compounds Nos. 1-2, 1-16 and 1-34 prepared in Example 9 in respectively indicated proportions.

A ferroelectric liquid crystal device was prepared in the same manner as in Example 3 except for using the composition P. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 374 | 246 | 189 |

Further, when the device was driven, a clear switching action was observed, and good bistability was shown after the termination of the voltage application.

As is understood from the comparison between Example 16 and Comparative Example 2, a ferroelectric liquid crystal device using the liquid crystal composition P containing the mesomorphic compound according to the present invention showed an improved low-temperature operation characteristic, a high response speed and a decreased temperature-dependence of the response speed.

EXAMPLE 17

A liquid crystal composition Q was prepared in the same manner as in Example 9 except that the following Example Compounds were used instead of Example Compounds Nos. 1-2, 1-16 and 1-34 prepared in Example 9 in respectively indicated proportions.

| Ex. Comp. No. | Structural formula | wt. parts |
|---|---|---|
| 1-2 | 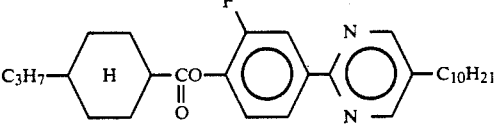 | 3 |
| 1-21 | 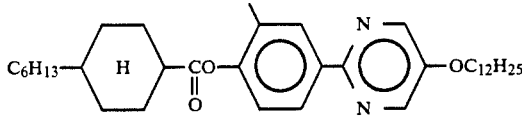 | 3 |
| 1-90 | 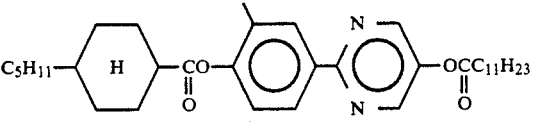 | 2 |
| 1-94 | 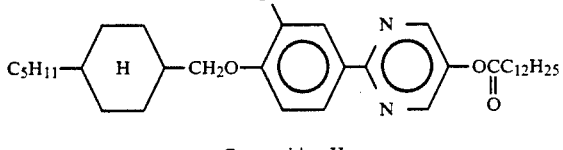 | 2 |
| | Composition H | 90 |

| Ex. Comp. No. | Structural formula | wt. parts |
|---|---|---|
| 1-8 | $C_5H_{11}$—[H]—CO-O—[F-phenyl]—[pyrimidine]—$C_{10}H_{21}$ | 3 |
| 1-82 | $C_4H_9$—[H]—$OCH_2$—[F-phenyl]—[pyrimidine]—$C_8H_{17}$ | 4 |
| 1-96 | $C_3H_7$—[H]—O-CO—[CN-phenyl]—[pyrimidine]—$OCOC_9H_{19}$ | 2 |
| 1-101 | $C_3H_7$—[H]—$CH_2O$—[F-phenyl]—[pyrimidine]—$OCOC_{10}H_{21}$ | 1 |
| Composition H | | 90 |

A ferroelectric liquid crystal device was prepared in the same manner as in Example 3 except for using the composition Q. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 366 | 243 | 184 |

Further, when the device was driven, a clear switching action was observed, and good bistability was shown after the termination of the voltage application.

As is understood from the comparison between Example 17 and Comparative Example 2, a ferroelectric liquid crystal device using the liquid crystal composition Q containing the mesomorphic compound according to the present invention showed an improved low-temperature operation characteristic, a high response speed and a decreased temperature-dependence of the response speed.

EXAMPLE 18

A blank cell was prepared in the same manner as in Example 3 by using a 2 % aqueous solution of polyvinyl alcohol resin (PVA-117, available from Kuraray K.K.) instead of the 1.5 %-solution of polyimide resin precursor in dimethylacetoamide on each electrode plate. A ferroelectric liquid crystal device was prepared by filling the blank cell with the liquid crystal composition B prepared in Example 3. The liquid crystal device was subjected to measurement of optical response time in the same manner as in Example 3. The results are shown below.

|  | 15° C. | 25° C. | 35° C. |
|---|---|---|---|
| Response time (μsec) | 128 | 85 | 70 |

EXAMPLE 19

A blank cell was prepared in the same manner as in Example 3 except for omitting the $SiO_2$ layer to form an alignment control layer composed of the polyimide resin layer alone on each electrode plate. A ferroelectric liquid crystal device was prepared by filling the blank cell with the liquid crystal composition B prepared in Example 3. The liquid crystal device was subjected to measurement of optical response time in the same manner as in Example 3. The results are shown below.

|  | 15° C. | 25° C. | 35° C. |
|---|---|---|---|
| Response time (μsec) | 125 | 83 | 68 |

As is apparent from the above Examples 18 and 19, also in the cases of different device structures, the devices containing the ferroelectric liquid crystal composition B according to the present invention respectively provided a remarkably improved operation characteristic at a lower temperature and also a decreased temperature-dependence of the response speed.

EXAMPLES 20-22

2-fluoro-4-(5-octyl-2-pyrimidinyl)phenyl trans-4-n-propylcyclohexylcarboxylate (Example 20, Example Compound No. 1-104), 2-fluoro-4-(5-undecyl-2-pyrimidinyl)phenyl trans-4-n-propylcyclohexyl-carboxylate (Example 21, Example Compound No. 1-3) and 2-fluoro-4-(5-undecyl-2-pyrimidinyl)phenyl trans-4-n-pentylcyclohexylcarboxylate (Example 22, Example Compound No. 1-107) were synthesized similarly as in Example 1 or Example 2. Each Example Compound showed the following phase transition series, respectively.

EXAMPLE 20

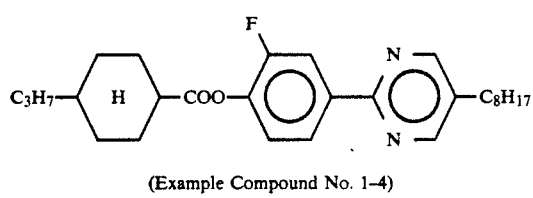

(Example Compound No. 1-4)

Phase transition temperature (°C.)

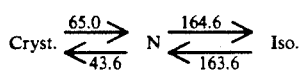

EXAMPLE 21

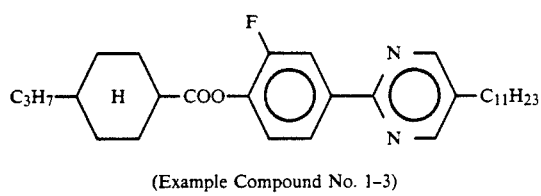

(Example Compound No. 1-3)

Phase transition temperature (°C.)

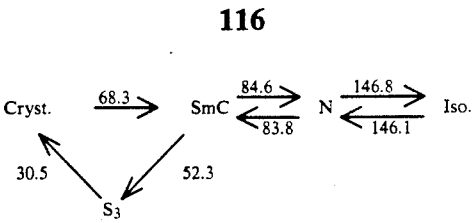

EXAMPLE 22

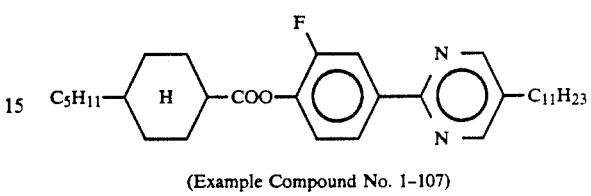

(Example Compound No. 1-107)

Phase transition temperature (°C.)

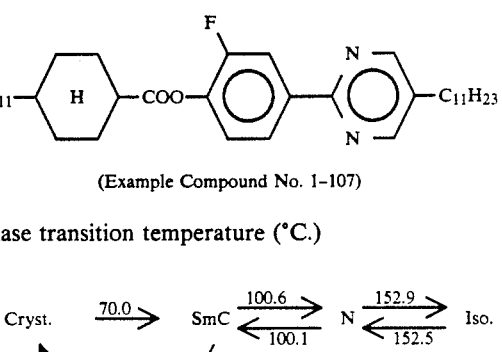

EXAMPLE 23

A liquid crystal composition R was prepared by mixing the following compounds in respectively indicated proportions.

| Ex. Comp. No. | Structural formula | wt. parts |
|---|---|---|
| 20 | $C_{10}H_{21}O$—[pyrazine]—[phenyl]—O$(CH_2)_3$CH(CH$_3$)$^*$CH$_2$C$_2$H$_5$ | 15 |
| 21 | $C_8H_{17}$—[pyrazine]—[phenyl]—O$(CH_2)_3$CH(CH$_3$)$^*$CH$_2$C$_2$H$_5$ | 15 |
| 58 | $C_8H_{17}$—[pyrazine]—[phenyl]—O$(CH_2)_3$CH(CH$_3$)$^*$OC$_5$H$_{11}$ | 10 |
| 89 | $C_{10}H_{21}$—[pyrazine]—[phenyl]—O$(CH_2)_3$CH(CH$_3$)$^*$OC$_3$H$_7$ | 20 |
| 159 | $C_3H_7$—[H]—CO-O—[phenyl]—[pyrazine]—$C_{12}H_{25}$ | 15 |
| 165 | $C_5H_{11}$—[H]—$CH_2O$—[phenyl]—[pyrazine]—$C_6H_{13}$ | 5 |

The liquid crystal composition R was further mixed with the following Example Compounds in the proportions indicated below to provide a liquid crystal composition 23-R.

COMPARATIVE EXAMPLE 3

A liquid crystal composition 23-Rb was prepared by omitting only Example Compounds Nos. 1-2 and 1-109 from the liquid crystal composition 23-R prepared in Example 23, otherwise in the same manner as in Example 23.

| Ex. Comp. No. | Structural formula | wt. parts |
|---|---|---|
| 1-2 | $C_3H_7-\text{[H]}-CO\text{-}O-\text{[Ph-F]}-\text{[Pyr(N,N)]}-C_{10}H_{21}$ | 3.5 |
| 1-109 | $C_3H_7-\text{[H]}-CO\text{-}O-\text{[Ph-F]}-\text{[Pyr(N,N)]}-C_{12}H_{25}$ | 1.5 |
| 3-69 | $C_{10}H_{21}-\text{[Pyr(N,N)]}-\text{[Ph]}-O\text{-}CO-\text{[Ph]}-OCH_2\overset{*}{C}HC_6H_{13}$ (with F) | 12.0 |
| 3-94 | $C_{10}H_{21}-\text{[Pyr(N,N)]}-\text{[Ph]}-OCH_2\overset{*}{C}HC_8H_{17}$ (with F) | 7.0 |
| 2-16 | $C_8H_{17}-\text{[Pyr(N,N)]}-\text{[Ph]}-OC_6H_{13}$ | 6.5 |
| 2-24 | $C_9H_{19}-\text{[Pyr(N,N)]}-\text{[Ph]}-OC_8H_{17}$ | 6.5 |
| 2-54 | $C_{10}H_{21}-\text{[Pyr(N,N)]}-\text{[Ph]}-O\text{-}(CH_2)_4\text{-}CHOCH_3$ (with $CH_3$) | 3.5 |
| 2-67 | $C_9H_{19}-\text{[Pyr(N,N)]}-\text{[Ph]}-O\text{-}CO\text{-}C_7H_{15}$ | 3.5 |
| Composition R | | 56.0 |

A ferroelectric liquid crystal device was prepared in the same manner as in Example 3 except for using the composition 23-R. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 115 | 80 | 68 |

A ferroelectric liquid crystal device was prepared in the same manner as in Example 3 except that the liquid crystal composition 23-Rb was injected into a cell. The measured values of the response time of the device were as follows.

|  | 15° C. | 25° C. | 35° C. |
|---|---|---|---|
| Response time (μsec) | 132 | 87 | 71 |

As is understood from the comparison between Example 23 and Comparative Example 3, a ferroelectric liquid crystal device using the liquid crystal composition 23-R containing the mesomorphic compound according to the present invention showed an improved low-temperature operation characteristic, a high response speed and a decreased temperature-dependence of the response speed.

EXAMPLE 24

A liquid crystal composition 24-R was prepared by mixing Example Compounds Nos. 1-2, 1-109, 2-16, 2-24, 2-54 and 2-67 and the liquid crystal composition R used in Example 23 in respectively indicated proportions.

| Ex. Comp. No. | wt. parts |
| --- | --- |
| 1-2 | 3.5 |
| 1-109 | 1.5 |
| 2-16 | 6.5 |
| 2-24 | 6.5 |
| 2-54 | 3.5 |
| 2-67 | 3.5 |
| Composition R | 75.0 |

A ferroelectric liquid crystal device was prepared in the same manner as in Example 3 except for using the composition 24-R. The ferroelectric liquid crystal device was subjected to measurement of response time and observation of a switching state, etc. in the same manner as in Example 3, whereby the following results were obtained.

|  | 15° C. | 25° C. | 35° C. |
| --- | --- | --- | --- |
| Response time (μsec) | 205 | 141 | 114 |

COMPARATIVE EXAMPLE 4

A liquid crystal composition 24-Rb was 5 prepared by omitting only Example Compounds Nos. 1-2 and 1-109 from the liquid crystal composition 24-R prepared in Example 24, otherwise in the same manner as in Example 24.

A ferroelectric liquid crystal device was prepared in the same manner as in Example 3 except that the liquid crystal composition 24-Rb was injected into a cell. The measured values of the response time of the device were as follows.

|  | 15° C. | 25° C. | 35° C. |
| --- | --- | --- | --- |
| Response time (μsec) | 235 | 158 | 119 |

As is understood from the comparison between Example 24 and Comparative Example 4, a ferroelectric liquid crystal device using the liquid crystal composition 24-R containing the mesomorphic compound according to the present invention showed an improved low-temperature operation characteristic, a high response speed and a decreased temperature-dependence of the response speed.

EXAMPLE 25

A liquid crystal composition 25-R was prepared by mixing Example Compounds Nos. 1-2 and 1-109 and the liquid crystal composition R used in Example 24 in respectively indicated proportions.

| Ex. Comp. No. | wt. parts |
| --- | --- |
| 1-2 | 3.5 |
| 1-109 | 1.5 |
| Composition R | 95.0 |

A ferroelectric liquid crystal device was prepared in the same manner as in Example 3 except for using the composition 25-R. The ferroelectric liquid crystal device was subjected to measurement of response time and observation of a switching state, etc. in the same manner as in Example 3, whereby the following results were obtained.

|  | 15° C. | 25° C. | 35° C. |
| --- | --- | --- | --- |
| Response time (μsec) | 275 | 180 | 155 |

COMPARATIVE EXAMPLE 5

A ferroelectric liquid crystal device was prepared in the same manner as in Example 3 except that the liquid crystal composition R used in Example 25 was injected into a cell. The measured values of the response time of the device were as follows.

|  | 15° C. | 25° C. | 35° C. |
| --- | --- | --- | --- |
| Response time (μsec) | 315 | 213 | 159 |

As is understood from the comparison between Example 25 and Comparative Example 5, a ferroelectric liquid crystal device using the liquid crystal composition 25-R containing the mesomorphic compound according to the present invention showed an improved low-temperature operation characteristic, a high response speed and a decreased temperature-dependence of the response speed.

EXAMPLE 26

A liquid crystal composition 26-R was prepared in the same manner as in Example 23 except that the following Example Compounds were used instead of Example Compounds Nos. 1-2, 1-109, 2-16, 2-24, 2-65, 2-67, 3-69 and 2-94 prepared in Example 23 in respectively indicated proportions.

| Ex. Comp. No. | Structural formula | wt. parts |
| --- | --- | --- |
| 1-8 | $C_5H_{11}$—⟨H⟩—CO—O—⟨F⟩—⟨⟩—⟨N,N⟩—$C_{10}H_{21}$ | 5.0 |

| Ex. Comp. No. | Structural formula | wt. parts |
|---|---|---|
| 1-37 | 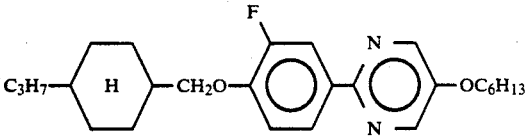 | 5.0 |
| | Composition R | 90.0 |

A ferroelectric liquid crystal device was prepared in the same manner as in Example 3 except for using the composition 26-R. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 265 | 179 | 148 |

As is understood from the comparison between Example 26 and Comparative Example 5, a ferroelectric liquid crystal device using the liquid crystal composition 26-R containing the mesomorphic compound according to the present invention showed an improved low-temperature operation characteristic, a high response speed and a decreased temperature-dependence of the response speed.

EXAMPLE 27

A liquid crystal composition 27-R was prepared in the same manner as in Example 23 except that the following Example Compounds were used instead of Example Compounds Nos. 1-2, 1-109, 2-16, 2-24, 2-54, 2-67 3-69 and 3-94 prepared in Example 23 in respectively indicated proportions.

| Ex. Comp. No. | Structural formula | wt. parts |
|---|---|---|
| 1-17 | 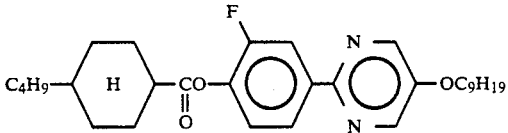 | 3 |
| 1-61 | 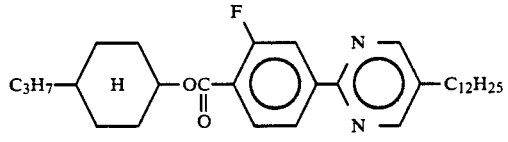 | 3 |
| 1-45 | 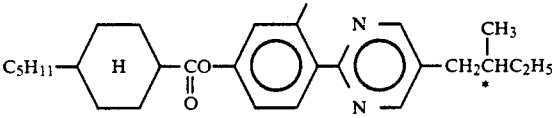 | 4 |
| 2-24 | 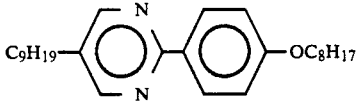 | 6.5 |
| 2-11 | 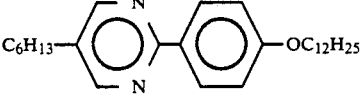 | 2 |
| 2-76 | 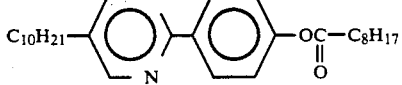 | 5 |
| 2-44 | 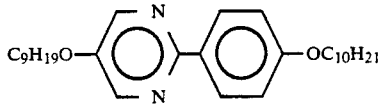 | 5.0 |

| Ex. Comp. No. | Structural formula | wt. parts |
|---|---|---|
| 2-97 | 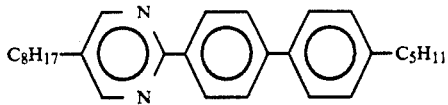 | 6.5 |
| | Composition R | 65 |

A ferroelectric liquid crystal devices was prepared in the same manner as in Example 3 except for using the composition 27-R. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 200 | 134 | 112 |

COMPARATIVE EXAMPLE 6

A liquid crystal composition 27-Rb was prepared by omitting only Example Compounds Nos. 1-17, 1-61 and 1-45 from the liquid crystal composition 27-R prepared in Example 27, otherwise in the same manner as in Example 27.

A ferroelectric liquid crystal device was prepared in the same manner as in Example 3 except that the liquid crystal composition 27-Rb was injected into a cell. The measured values of the response time of the device were as follows:

| | 15° C. | 25° C. | 35° C. |
|---|---|---|---|
| Response time (μsec) | 228 | 154 | 115 |

As is understood from the comparison between Example 27 and Comparative Example 6, a ferroelectric liquid crystal device using the liquid crystal composition 27-R containing the mesomorphic compound according to the present invention showed an improved low-temperature operation characteristic, a high response speed and a decreased temperature-dependence of the response speed.

EXAMPLE 28

A liquid crystal composition 28-R was prepared in the same manner as in Example 23 except that the following Example Compounds were used instead of Example Compounds Nos. 1-2, 1-109, 2-16, 2-24, 2-54, 2-67, 3-69 and 3-94 prepared in Example 23 in respectively indicated proportions.

| Ex. Comp. No. | Structural formula | wt. parts |
|---|---|---|
| 1-11 | 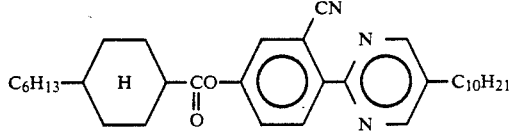 | 4 |
| 1-49 | 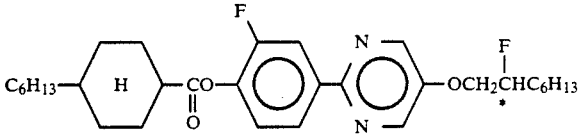 | 3 |
| 1-55 | 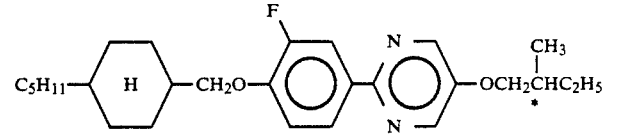 | 3 |
| 2-9 | 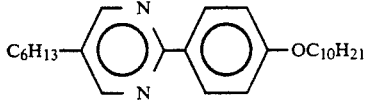 | 3 |
| 2-17 | 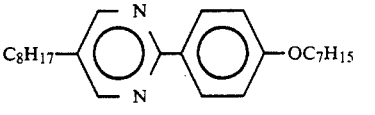 | 12 |

-continued

| Ex. Comp. No. | Structural formula | wt. parts |
|---|---|---|
| 2-48 |  | 3 |
| 2-55 | 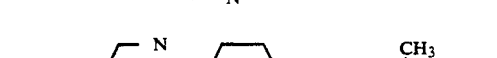 | 7 |
| 2-86 |  | 3 |
| 3-75 | 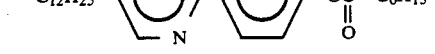 | 8.5 |
| 3-28 |  | 10.5 |
| | Composition R | 43 |

A ferroelectric liquid crystal device was prepared in the same manner as in Example 3 except for using the composition 28-R. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 100 | 72 | 58 |

COMPARATIVE EXAMPLE 7

A liquid crystal composition 28-Rb was prepared by omitting only Example Compounds Nos. 1-11, 1-49 and 1-55 from the liquid crystal composition 28-R prepared in Example 28, otherwise in the same manner as in Example 28.

A ferroelectric liquid crystal device was prepared in the same manner as in Example 3 except that the liquid crystal composition 28-Rb was injected into a cell. The measured values of the response time of the device were as follows.

| | 15° C. | 25° C. | 35° C. |
|---|---|---|---|
| Response time (μsec) | 115 | 76 | 60 |

As is understood from the comparison between Example 28 and Comparative Example 7, a ferroelectric liquid crystal device using the liquid crystal composition 28-R containing the mesomorphic compound according to the present invention showed an improved low-temperature operation characteristic, a high response speed and a decreased temperature-dependence of the response speed.

EXAMPLE 29

A liquid crystal composition 29-R was prepared in the same manner as in Example 23 except that the following Example Compounds were used instead of Example Compounds Nos. 1-2, 1-109, 2-16, 2-24, 2-54, 2-67, 3-69 and 3-94 prepared in Example 23 in respectively indicated proportions.

| Ex. Comp. No. | Structural formula | wt. parts |
|---|---|---|
| 1-20 | 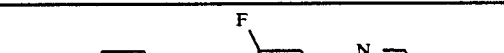 | 4 |
| 1-72 |  | 4 |

-continued

| Ex. Comp. No. | Structural formula | wt. parts |
|---|---|---|
| 1-80 | C₃H₇—(H)—OCH₂—⟨C₆H₃(CN)⟩—⟨pyrazine⟩—C₁₀H₂₁ | 2 |
| 2-18 | C₈H₁₇—⟨pyrazine⟩—⟨C₆H₄⟩—OC₈H₁₇ | 10 |
| 2-22 | C₉H₁₉—⟨pyrazine⟩—⟨C₆H₄⟩—OC₆H₁₃ | 3 |
| 2-31 | C₁₀H₂₁—⟨pyrazine⟩—⟨C₆H₄⟩—OC₈H₁₇ | 6 |
| 2-56 | C₆H₁₃—⟨pyrazine⟩—⟨C₆H₄⟩—OC(=O)—C₈H₁₇ | 3 |
| 2-90 | C₉H₁₉O—⟨pyrazine⟩—⟨C₆H₄⟩—OC(=O)—C₇H₁₅ | 3 |
| 3-48 | C₈H₁₇O—⟨C₆H₄⟩—C(=O)O—⟨C₆H₄⟩—C(=O)OCH₂CHFC₈H₁₇* | 8 |
| 3-109 | C₁₀H₂₁—⟨pyrazine⟩—⟨C₆H₄⟩—OC(=O)—CHF*—C₆H₁₃ | 11 |
| Composition R | | 46 |

A ferroelectric liquid crystal device was prepared in the same manner as in Example 3 except for using the composition 29-R. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 112 | 76 | 65 |

COMPARATIVE EXAMPLE 8

A liquid crystal composition 29-Rb was prepared by omitting only Example Compounds Nos. 1-20, 1-72 and 1-80 from the liquid crystal composition 29-R prepared in Example 29, otherwise in the same manner as in Example 29.

A ferroelectric liquid crystal device was prepared in the same manner as in Example 3 except that the liquid crystal composition 29-Rb was injected into a cell. The measured values of the response time of the device were as follows.

|  | 15° C. | 25° C. | 35° C. |
|---|---|---|---|
| Response time (μsec) | 130 | 89 | 68 |

As is understood from the comparison between Example 29 and Comparative Example 8, a ferroelectric liquid crystal device using the liquid crystal composition 29-R containing the mesomorphic compound according to the present invention showed an improved low-temperature operation characteristic, a high response speed and a decreased temperature-dependence of the response speed.

EXAMPLE 30

A liquid crystal composition S was prepared by mixing the following compounds in respectively indicated proportions.

| Ex. Comp. No. | Structural formula | wt. parts |
|---|---|---|
| 8 | $C_8H_{17}O$—⟨Ph⟩—OC(=O)—⟨Ph⟩—⟨Ph⟩—$CH_2\overset{*}{C}H(CH_3)C_2H_5$ | 16 |
| 9 | $C_8H_{17}O$—⟨Ph⟩—C(=O)(S)—⟨Ph⟩—$CH_2\overset{*}{C}H(CH_3)C_2H_5$ | 22.5 |
| 18 | $C_8H_{17}O$—⟨Ph⟩—C(=O)O—⟨Ph⟩—$OCH_2\overset{*}{C}H(CH_3)C_2H_5$ | 64 |
| 23 | $C_8H_{17}$—⟨Pyrimidine(N,N)⟩—⟨Ph⟩—$O(CH_2)_5\overset{*}{C}H(CH_3)C_2H_5$ | 10 |
| 24 | $C_{11}H_{23}O$—⟨Pyrimidine(N,N)⟩—⟨Ph⟩—$O(CH_2)_2\overset{*}{C}H(CH_3)C_2H_5$ | 10 |
| 43 | $C_{10}H_{21}O$—⟨Ph⟩—C(=O)(S)—⟨Ph⟩—$OCH_2\overset{*}{C}H(CH_3)C_2H_5$ | 22.5 |
| 63 | $C_{10}H_{21}OC(=O)$—⟨Ph⟩—⟨Ph⟩—OC(=O)—⟨Ph⟩—$OCH_2\overset{*}{C}H(CH_3)OC_5H_{11}$ | 15 |
| 87 | $C_6H_{13}OC(=O)$—⟨Ph⟩—⟨Ph⟩—OC(=O)—⟨Ph⟩—$OCH_2\overset{*}{C}H(CH_3)OC_8H_{17}$ | 15 |
| 159 | $C_3H_7$—⟨Cyclohexyl(H)⟩—C(=O)O—⟨Ph⟩—⟨Pyrimidine(N,N)⟩—$C_{12}H_{25}$ | 20 |

The liquid crystal composition S was further mixed with the following Example Compounds in the proportions indicated below to provide a liquid crystal composition 30-S.

| Ex. Comp. No. | Structural formula | wt. parts |
|---|---|---|
| I-2 | $C_3H_7$—⟨Cyclohexyl(H)⟩—C(=O)O—⟨Ph(F)⟩—⟨Pyrimidine(N,N)⟩—$C_{10}H_{21}$ | 2 |
| I-9 | $C_5H_{11}$—⟨Cyclohexyl(H)⟩—C(=O)O—⟨Ph(F)⟩—⟨Pyrimidine(N,N)⟩—$C_{12}H_{25}$ | 2 |

-continued

| Ex. Comp. No. | Structural formula | wt. parts |
|---|---|---|
| 1-16 | $C_3H_7$—[H]—CO—O—[F-phenyl]—[pyridine(N,N)]—$OC_{12}H_{25}$ | 3 |
| 1-34 | $C_5H_{11}$—[H]—$CH_2O$—[F-phenyl]—[pyridine(N,N)]—$C_7H_{15}$ | 3 |
| 2-15 | $C_7H_{15}$—[pyrimidine(N,N)]—[phenyl]—$OC_{14}H_{29}$ | 5 |
| 2-19 | $C_8H_{17}$—[pyrimidine(N,N)]—[phenyl]—$OC_9H_{19}$ | 10 |
| 2-25 | $C_9H_{19}$—[pyrimidine(N,N)]—[phenyl]—$OC_9H_{19}$ | 5 |
| 2-29 | $C_{10}H_{21}$—[pyrimidine(N,N)]—[phenyl]—$OC_6H_{13}$ | 5 |
| 3-13 | $C_{12}H_{25}O$—[phenyl]—CO—O—[phenyl]—$OCH_2\overset{F}{\underset{*}{C}}HC_6H_{13}$ | 7 |
| 3-7 | $C_8H_{17}O$—[phenyl]—CO—O—[phenyl]—$OCH_2\overset{F}{\underset{*}{C}}HC_5H_{11}$ | 6 |
| 3-92 | $C_{12}H_{25}$—[pyridine(N,N)]—[phenyl]—$OCH_2\overset{F}{\underset{*}{C}}HC_6H_{13}$ | 10 |
| | Composition S | 42 |

A ferroelectric liquid crystal device was prepared in the same manner as in Example 3 except for using the composition 30-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 335 | 215 | 178 |

COMPARATIVE EXAMPLE 9

A liquid crystal composition 30-Sb was prepared by omitting only Example Compounds Nos. 1-2, 1-9, 1-16 and 1-34 from the liquid crystal composition 30-S prepared in Example 30, otherwise in the same manner as in Example 30.

A ferroelectric liquid crystal device was prepared in the same manner as in Example 3 except that the liquid crystal composition 30-Sb was injected into a cell. The measured values of the response time of the device were as follows.

|  | 15° C. | 25° C. | 35° C. |
|---|---|---|---|
| Response time (μsec) | 385 | 231 | 180 |

As is understood from the comparison between Example 30 and Comparative Example 9, a ferroelectric liquid crystal device using the liquid crystal composition 30-S containing the mesomorphic compound according to the present invention showed an improved low-temperature operation characteristic, a high response speed and a decreased temperature-dependence of the response speed.

EXAMPLE 31

A liquid crystal composition 31-S was prepared by mixing Example Compounds Nos. 1-2, 1-9, 1-16, 1-34, 2-15, 2-19, 2-25 and 2-29 and the liquid crystal composition S used in Example 30 in respectively indicated proportions.

| Ex. Comp. No. | wt. parts |
|---|---|
| 1-2 | 2 |
| 1-9 | 2 |
| 1-16 | 3 |
| 1-34 | 3 |
| 2-15 | 5 |
| 2-19 | 10 |
| 2-25 | 5 |
| 2-29 | 5 |
| Composition S | 65 |

A ferroelectric liquid crystal device was prepared in the same manner as in Example 3 except for using the composition 31-S. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 595 | 405 | 285 |

COMPARATIVE EXAMPLE 10

A liquid crystal composition 31-Sb was prepared by omitting only Example Compounds Nos. 1-2, 1-9, 1-16 and 1-34 from the liquid crystal composition 31-S prepared in Example 31, otherwise in the same manner as in Example 31.

A ferroelectric liquid crystal device was prepared in the same manner as in Example 3 except that the liquid crystal composition 31-Sb was injected into a cell. The measured values of the response time of the device were as follows.

|  | 15° C. | 25° C. | 35° C. |
|---|---|---|---|
| Response time (μsec) | 685 | 466 | 291 |

As is understood from the comparison between Example 31 and comparative Example 10, a ferroelectric liquid crystal device using the liquid crystal composition 31-S containing the mesomorphic compound according to the present invention showed an improved low-temperature operation characteristic, a high response speed and a decreased temperature-dependence of the response speed.

EXAMPLE 32

A liquid crystal composition 32-S was prepared by mixing Example Compounds Nos. 1-2, 1-9, 1-16 and 1-34 and the liquid crystal composition S used in Example 30 in respectively indicated proportions.

| Ex. Comp. No. | wt. parts |
|---|---|
| 1-2 | 2 |
| 1-9 | 2 |
| 1-16 | 3 |
| 1-34 | 3 |
| Composition S | 90 |

A ferroelectric liquid crystal device was prepared in the same manner as in Example 3 except for using the composition 32-S. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 735 | 500 | 360 |

COMPARATIVE EXAMPLE 11

A ferroelectric liquid crystal device was prepared in the same manner as in Example 3 except that the liquid crystal composition S used in Example 32 was injected into a cell. The measured values of the response time of the device were as follows.

|  | 15° C. | 25° C. | 35° C. |
|---|---|---|---|
| Response time (μsec) | 905 | 611 | 381 |

As is understood from the comparison between Example 32 and Comparative Example 11, a ferroelectric liquid crystal device using the liquid crystal composition 32-S containing the mesomorphic compound according to the present invention showed an improved low-temperature operation characteristic, a high response speed and a decreased temperature-dependence of the response speed.

EXAMPLE 33

A liquid crystal composition 33-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-6 | $C_4H_9$—[H]—CO-O—(Cl-phenyl)—(pyridine-N,N)—$C_{10}H_{21}$ | 3 |
| 1-33 | $C_5H_{11}$—[H]—$CH_2O$—(Cl-phenyl)—(pyridine-N,N)—$C_6H_{13}$ | 4 |
| 1-64 | $C_4H_9$—[H]—O-CO—(Br-phenyl)—(pyridine-N,N)—$C_9H_{19}$ | 4 |
| Composition S | | 90 |

A ferroelectric liquid crystal device was prepared in the same manner as in Example 3 except for using the composition 33-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 740 | 495 | 345 |

As is understood from the comparison between Example 33 and Comparative Example 11, a ferroelectric liquid crystal device using the liquid crystal composition 33-S containing the mesomorphic compound according to the present invention showed an improved low-temperature operation characteristic, a high response speed and a decreased temperature-dependence of the response speed.

EXAMPLE 34

A liquid crystal composition 34-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-48 | $C_5H_{11}$—[H]—CO-O—(F-phenyl)—(pyridine-N,N)—O-$(CH_2)_4$CH($CH_3$)O$CH_3$ | 3 |
| 1-53 | $C_5H_{11}$—[H]—$CH_2O$—(F-phenyl)—(pyridine-N,N)—$(CH_2)_4$CH($CH_3$)$C_3H_5$* | 3 |
| 1-71 | $C_3H_7$—[H]—O-CO—(F-phenyl)—(pyridine-N,N)—O$CH_2$CH(F)$C_6H_{13}$* | 4 |
| 2-7 | $C_6H_{13}$—(pyridine-N,N)—(phenyl)—O$C_8H_{17}$ | 2 |

-continued

| Ex. Comp. No. | Structural formula | wt. parts |
| --- | --- | --- |
| 2-12 | $C_7H_{15}$—pyrazine—phenyl—$OC_6H_{13}$ | 2 |
| 2-20 | $C_8H_{17}$—pyrazine—phenyl—$OC_{10}H_{21}$ | 6 |
| 2-35 | $C_{11}H_{23}$—pyrazine—phenyl—$OC_8H_{17}$ | 6 |
| 2-39 | $C_{12}H_{25}$—pyrazine—phenyl—$OC_8H_{17}$ | 8 |
| 2-45 | $C_{11}H_{23}O$—pyrazine—phenyl—$OC_6H_{13}$ | 4 |
| 2-112 | $C_{14}H_{29}$—phenyl—pyrazine—phenyl—$OC_6H_{13}$ | 5 |
| 2-113 | $C_9H_{19}OC(=O)$—pyrazine—phenyl—$C_9H_{19}$ | 5 |
| Composition S | | 52 |

A ferroelectric liquid crystal device was prepared in the same manner as in Example 3 except for using the composition 34-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
| --- | --- | --- | --- |
| Response time (μsec) | 593 | 403 | 283 |

COMPARATIVE EXAMPLE 12

A liquid crystal composition 34-Sb was prepared by omitting only Example Compounds Nos. 1-48, 1-53 and 1-71 from the liquid crystal composition 34-R prepared in Example 34, otherwise in the same manner as in Example 34.

A ferroelectric liquid crystal device was prepared in the same manner as in Example 3 except that the liquid crystal composition 34-Sb was injected into a cell. The measured values of the response time of the device were as follows.

| | 15° C. | 25° C. | 35° C. |
| --- | --- | --- | --- |
| Response time (μsec) | 695 | 475 | 287 |

As is understood from the comparison between Example 34 and Comparative Example 12, a ferroelectric liquid crystal device using the liquid crystal composition 34-S containing the mesomorphic compound according to the present invention showed an improved low-temperature operation characteristic, a high response speed and a decreased temperature-dependence of the response speed.

EXAMPLE 35

A liquid crystal composition 35-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-4 | C$_3$H$_7$–[Cy]–CO–O–[Ph(F)]–[Pyr]–C$_6$H$_{13}$ | 2 |
| 1-8 | C$_5$H$_{11}$–[Cy]–CO–O–[Ph(F)]–[Pyr]–C$_{10}$H$_{21}$ | 2 |
| 1-49 | C$_6$H$_{13}$–[Cy]–CO–O–[Ph(F)]–[Pyr]–OCH$_2$C*HFC$_6$H$_{13}$ | 3 |
| 1-63 | C$_4$H$_9$–[Cy]–O–CO–[Ph(F)]–[Pyr]–C$_8$H$_{17}$ | 2 |
| 1-86 | C$_5$H$_{11}$–[Cy]–OCH$_2$–[Ph(CH$_3$)]–[Pyr]–C$_6$H$_{13}$ | 2 |
| 2-1 | C$_5$H$_{11}$–[Pyr]–[Ph]–OC$_8$H$_{17}$ | 3 |
| 2-16 | C$_8$H$_{17}$–[Pyr]–[Ph]–OC$_6$H$_{13}$ | 4 |
| 2-20 | C$_8$H$_{17}$–[Pyr]–[Ph]–OC$_{10}$H$_{21}$ | 4 |
| 2-41 | C$_{12}$H$_{25}$–[Pyr]–[Ph]–OC$_{12}$H$_{25}$ | 6 |
| 2-61 | C$_8$H$_{17}$–[Pyr]–[Ph]–O–CO–C$_6$H$_{13}$ | 2 |
| 2-70 | C$_9$H$_{19}$–[Pyr]–[Ph]–O–CO–C$_{12}$H$_{25}$ | 2 |
| 2-92 | C$_{12}$H$_{25}$–[Pyr]–[Ph]–O–CO–CH(CH$_3$)–OC$_5$H$_{11}$ | 2 |

-continued

| Ex. Comp. No. | Structural formula | wt. parts |
|---|---|---|
| 3-18 | $C_{12}H_{25}O-\bigcirc-\underset{\underset{O}{\|\|}}{CO}-\bigcirc-OCH_2\overset{F}{\underset{\|}{C}}HC_8H_{17}$ | 8 |
| 3-60 | $C_8H_{17}-\bigcirc-\underset{\underset{O}{\|\|}}{SC}-\bigcirc-OCH_2\overset{F}{\underset{\|}{\underset{*}{C}}}HC_8H_{17}$ | 6 |
| 3-83 | $C_{10}H_{21}-\underset{N}{\overset{N}{\bigcirc}}-\bigcirc-OCH_2\overset{F}{\underset{\|}{\underset{*}{C}}}HC_4H_9$ | 9 |
| Composition S | | 43 |

A ferroelectric liquid crystal device was prepared in the same manner as in Example 3 except for using the composition 35-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 313 | 205 | 172 |

COMPARATIVE EXAMPLE 13

A liquid crystal composition 35-Sb was prepared by omitting only Example Compounds Nos. 1-4, 1-8, 1-49, 1-63 and 1-86 from the liquid crystal composition 35-S prepared in Example 35, otherwise in the same manner as in Example 35.

A ferroelectric liquid crystal device was prepared in the same manner as in Example 3 except that the liquid crystal composition 35-Sb was injected into a cell. The measured values of the response time of the device were as follows.

|  | 15° C. | 25° C. | 35° C. |
|---|---|---|---|
| Response time (μsec) | 362 | 233 | 178 |

As is understood from the comparison between Example 35 and Comparative Example 13, a ferroelectric liquid crystal device using the liquid crystal composition 35-S containing the mesomorphic compound according to the present invention showed an improved low-temperature operation characteristic, a high response speed and a decreased temperature-dependence of the response speed.

EXAMPLE 36

A liquid crystal composition 36-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-1 | $CH_3-\bigcirc H-\underset{\underset{O}{\|\|}}{CO}-\overset{F}{\bigcirc}-\underset{N}{\overset{N}{\bigcirc}}-C_8H_{17}$ | 4 |
| 1-41 | $C_4H_9-\bigcirc H-CH_2O-\overset{F}{\bigcirc}-\underset{N}{\overset{N}{\bigcirc}}-\underset{\underset{O}{\|\|}}{CO}C_6H_{13}$ | 2 |
| 1-57 | $C_4H_9-\bigcirc H-CH_2O-\overset{F}{\bigcirc}-\underset{N}{\overset{N}{\bigcirc}}-OCH_2\overset{F}{\underset{\|}{\underset{*}{C}}}HC_8H_{17}$ | 3 |

| Ex. Comp. No. | Structural formula | wt. parts |
|---|---|---|
| 1-66 | 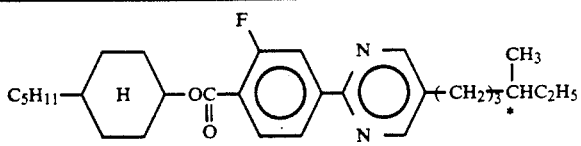 | 2 |
| | Composition S | 89 |

A ferroelectric liquid crystal device was prepared in the same manner as in Example 3 except for using the composition 36-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 718 | 487 | 365 |

As is understood from the comparison between Example 36 and Comparative Example 5, a ferroelectric liquid crystal device using the liquid crystal composition 36-S containing the mesomorphic compound according to the present invention showed an improved low-temperature operation characteristic, a high response speed and a decreased temperature-dependence of the response speed.

EXAMPLE 37

A liquid crystal composition 37-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-2 | 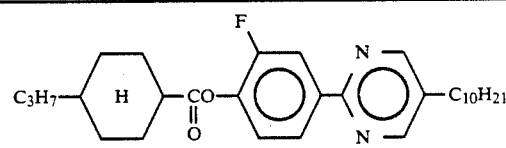 | 4 |
| 1-7 | 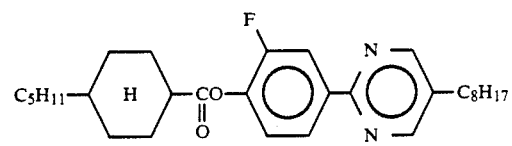 | 2 |
| 1-38 | 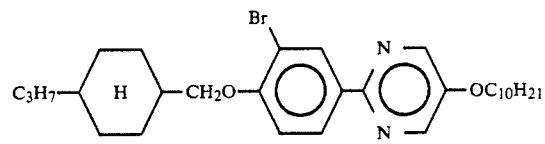 | 2 |
| 1-54 | 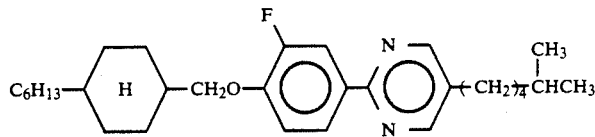 | 2 |
| 1-87 | 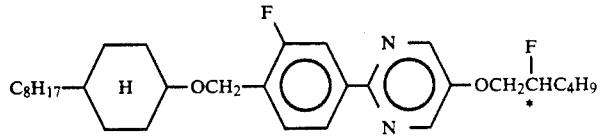 | 3 |
| 2-2 | 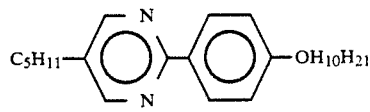 | 3 |

-continued

| Ex. Comp. No. | Structural formula | wt. parts |
|---|---|---|
| 2-7 | 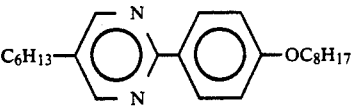 | 3 |
| 2-21 | 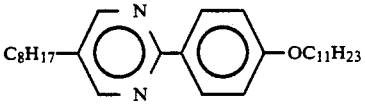 | 5 |
| 2-34 | 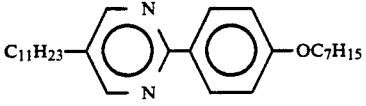 | 6 |
| 3-36 | 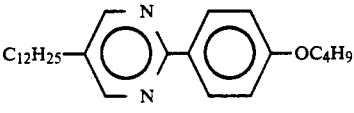 | 7 |
| 2-51 | 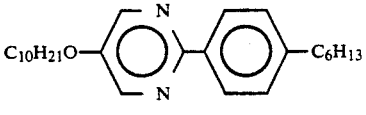 | 2.5 |
| 2-118 | 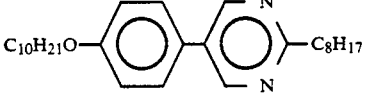 | 2.5 |
| 2-52 | 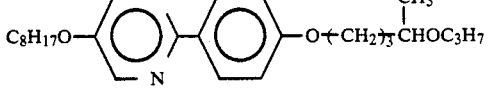 | 8 |
| 2-57 | 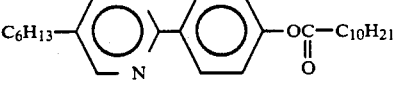 | 3.5 |
| 2-100 | 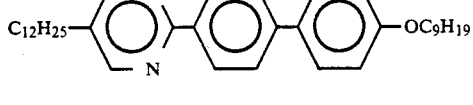 | 7 |
| 2-104 | 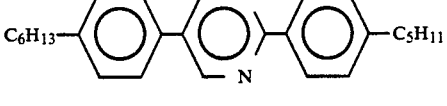 | 3 |
| 2-88 |  | 3.5 |
| | Composition S | 34 |

A ferroelectric liquid crystal device was prepared in the same manner as in Example 3 except for using the composition 37-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 555 | 381 | 283 |

COMPARATIVE EXAMPLE 14

A liquid crystal composition 37-Sb was prepared by omitting only Example Compounds Nos. 1-2, 1-7, 1-38, 1-54 and 1-87 from the liquid crystal composition 37-S prepared in Example 37, otherwise in the same manner as in Example 37.

A ferroelectric liquid crystal device was prepared in the same manner as in Example 3 except that the liquid crystal composition 37-Sb was injected into a cell. The measured values of the response time of the device were as follows.

|  | 15° C. | 25° C. | 35° C. |
|---|---|---|---|
| Response time (μsec) | 645 | 429 | 286 |

As is understood from the comparison between Example 37 and Comparative Example 14, a ferroelectric liquid crystal device using the liquid crystal composition 37-S containing the mesomorphic compound according to the present invention showed an improved low-temperature operation characteristic, a high response speed and a decreased temperature-dependence of the response speed.

EXAMPLE 38

A liquid crystal composition 38-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-49 | $C_6H_{13}$—H—CO—O—(F)—Ar—N=N—OCH$_2$CHC$_6$H$_{13}$ (F) | 4 |
| 1-71 | $C_3H_7$—H—OC(O)—(F)—Ar—N=N—OCH$_2$CHC$_6$H$_{13}$ (F) | 4 |
| 2-6 | $C_6H_{13}$—(N=N)—Ar—OC$_6$H$_{13}$ | 4 |
| 2-17 | $C_8H_{17}$—(N=N)—Ar—OC$_7$H$_{15}$ | 10 |
| 2-33 | $C_{11}H_{23}$—(N=N)—Ar—OC$_6$H$_{13}$ | 8 |
| 2-62 | $C_8H_{17}$—(N=N)—Ar—OCC$_7$H$_{15}$(=O) | 2 |
| 2-72 | $C_{10}H_{21}$—(N=N)—Ar—OCC$_4$H$_9$(=O) | 2 |
| 2-79 | $C_{10}H_{21}$—(N=N)—Ar—OCC$_{11}$H$_{23}$(=O) | 2 |
| 2-91 | $C_{10}H_{21}$O—(N=N)—Ar—OCC$_6$H$_{13}$(=O) | 2 |

| Ex. Comp. No. | Structural formula | wt. parts |
|---|---|---|
| 2-96 | 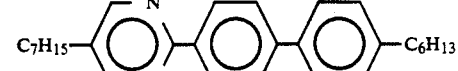 | 8 |
| 3-30 |  | 8 |
| 3-35 | 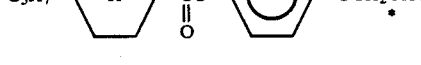 | 5 |
| 3-88 | 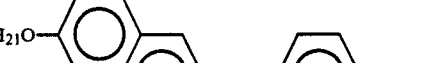 | 10 |
| Composition S | | 31 |

A ferroelectric liquid crystal device was prepared in the same manner as in Example 3 except for using the composition 38-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 250 | 176 | 130 |

COMPARATIVE EXAMPLE 15

A liquid crystal composition 38-Sb was prepared by omitting only Example Compounds Nos. 1-49 and 1-71 from the liquid crystal composition 38-S prepared in Example 38, otherwise in the same manner as in Example 38.

A ferroelectric liquid crystal device was prepared in the same manner as in Example 3 except that the liquid crystal composition 38-Sb was injected into a cell. The measured values of the response time of the device were as follows.

| | 15° C. | 25° C. | 35° C. |
|---|---|---|---|
| Response time (μsec) | 360 | 245 | 165 |

As is understood from the comparison between Example 38 and Comparative Example 15, a ferroelectric liquid crystal device using the liquid crystal composition 38-S containing the mesomorphic compound according to the present invention showed an improved low-temperature operation characteristic, a high response speed and a decreased temperature-dependence of the response speed.

EXAMPLE 39

A liquid crystal composition 39-S was prepared in the same manner as in Example 30 except that the following Example Compounds were used instead of Example Compounds Nos. 1-2, 1-9, 1-16, 1-34, 2-15, 2-19, 2-25, 2-29, 3-7, 3-13 and 3-92 prepared in Example 30 in respectively indicated proportions.

| Ex. Comp. No. | Structural formula | wt. parts |
|---|---|---|
| 1-2 | 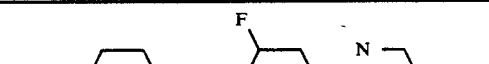 | 3 |
| 1-21 | 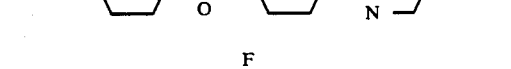 | 3 |

-continued

| Ex. Comp. No. | Structural formula | wt. parts |
|---|---|---|
| 1-90 | $C_5H_{11}$—[Cy-H]—CO-O—[Ph(F)]—[Pyr]—O-CO-$C_{11}H_{23}$ | 2 |
| 1-94 | $C_5H_{11}$—[Cy-H]—$CH_2O$—[Ph(F)]—[Pyr]—O-CO-$C_{12}H_{25}$ | 2 |
| 2-8 | $C_6H_{13}$—[Pyrazine]—[Ph]—$OC_9H_{19}$ | 5 |
| 2-13 | $C_7H_{15}$—[Pyrazine]—[Ph]—$OC_8H_{17}$ | 8 |
| 2-32 | $C_{10}H_{21}$—[Pyrazine]—[Ph]—$OC_9H_{19}$ | 7 |
| 2-55 | $C_{12}H_{25}$—[Pyrazine]—[Ph]—O–(CH$_2$)$_4$–CH(CH$_3$)–OCH$_3$ | 5 |
| 2-74 | $C_{10}H_{21}$—[Pyrazine]—[Ph]—O-CO-$C_6H_{13}$ | 2 |
| 2-75 | $C_{10}H_{21}$—[Pyrazine]—[Ph]—O-CO-$C_7H_{15}$ | 2 |
| 2-82 | $C_{11}H_{23}$—[Pyrazine]—[Ph]—O-CO-$C_7H_{15}$ | 2 |
| 2-102 | $C_9H_{19}O$—[Pyrazine]—[Ph]—[Ph]—$OC_8H_{17}$ | 5 |
| 3-19 | $C_6H_{13}O$—[Ph]—CO-O—[Ph]—O-$CH_2$-CHF*-$C_{12}H_{25}$ | 9 |
| 3-49 | $C_8H_{17}O$—[Ph]—CH=CH-CO-O—[Ph]—CO-O-$CH_2$-CHF*-$C_6H_{13}$ | 6 |

| Ex. Comp. No. | Structural formula | wt. parts |
|---|---|---|
| 3-101 | 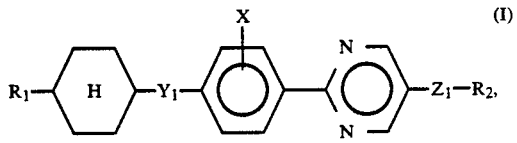 | 8 |
| | Composition S | 31 |

A ferroelectric liquid crystal device was prepared in the same manner as in Example 3 except for using the composition 39-S. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 321 | 207 | 175 |

COMPARATIVE EXAMPLE 16

A liquid crystal composition 39-Sb was prepared by omitting only Example Compounds Nos. 1-2, 1-21, 1-90 and 1-94 from the liquid crystal composition 39-S prepared in Example 39, otherwise in the same manner as in Example 39.

A ferroelectric liquid crystal device was prepared in the same manner as in Example 3 except that the liquid crystal composition 39-Sb was injected into a cell. The measured values of the response time of the device were as follows.

| | 15° C. | 25° C. | 35° C. |
|---|---|---|---|
| Response time (μsec) | 369 | 230 | 178 |

As is understood from the comparison between Example 39 and Comparative Example 16, a ferroelectric liquid crystal device using the liquid crystal composition 39-S containing the mesomorphic compound according to the present invention showed an improved low-temperature operation characteristic, a high response speed and a decreased temperature-dependence of the response speed.

As described above, according to the present invention, there are provided a ferroelectric liquid crystal composition and a ferroelectric liquid crystal device containing the composition, which shows a good switching characteristic, an improved low-temperature operation characteristic and a decreased temperature-dependence of response speed.

What is claimed is:

1. A liquid crystal composition comprising:
at least one mesomorphic compound having the following formula (I):

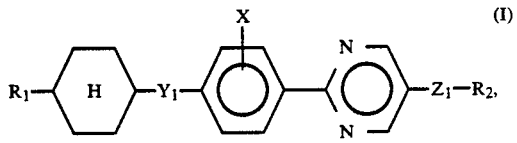

wherein $R_1$ and $R_2$ each is a linear or branched alkyl group having 1-16 carbon atoms capable of having a substituent; $Y_1$ is —COO—, —OCO—, —CH$_2$O— or —OCH$_2$; $Z_1$ is a single bond, —O—, —COO, or —OCOO—; and X is a halogen, cyano group or methyl group; and
at least one mesomorphic compound having the following formula (II):

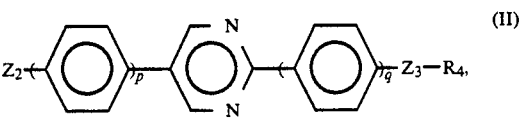

wherein $R_3$ and $R_4$ each is a linear or branched optically inactive alkyl group having 1-18 carbon atoms capable of having $C_1$-$C_{12}$ alkoxy group; $Z_2$ and $Z_3$ each is a single bond, —O—, —OCO—, —COO— or —OCOO—; and p and q are respectively 0, 1 or 2.

2. A liquid crystal composition comprising:
at least one mesomorphic compound having the following formula (I):

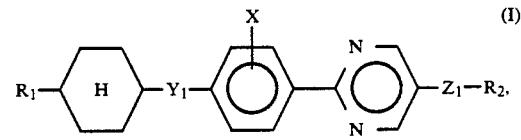

wherein $R_1$ and $R_2$ each is a linear or branched alkyl group having 1-16 carbon atoms capable of having a substituent; $Y_1$ is —COO—, —OCO—, —CH$_2$O—or —OCH$_2$; $Z_1$ is a single bond, —O—, —COO—, —OCO—, or —OCOO—; and X is a halogen, cyano group or methyl group; and
at least one mesomorphic compound having the following formula (III):

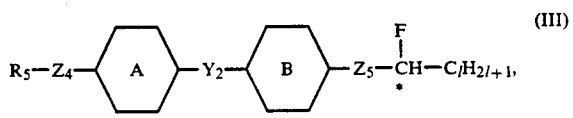

wherein $R_5$ is a linear or branched alkyl group having 1-18, carbon atoms capable of having a substituent; $Y_2$ is a single bond, —COO—, —OCO—, —COS—, —SCO—, —CH$_2$O—, —OCH₂— or —CH=CH—COO—; Z₄ is a single bond, —O—, —COO— or —OCO—; Z₅ is —OCH₂—, —COOCH₂—, —OCO— or —O(CH₂)ₖO—CH₂;

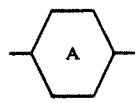

is

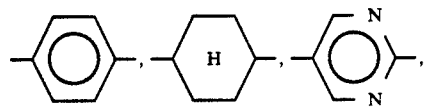

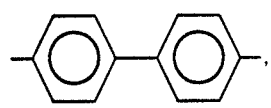

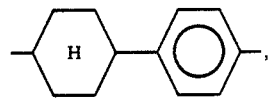

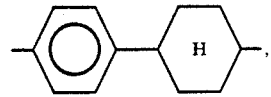

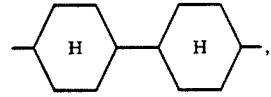

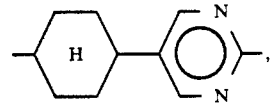

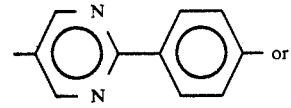

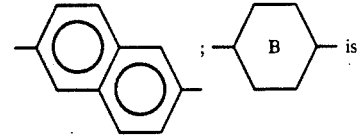

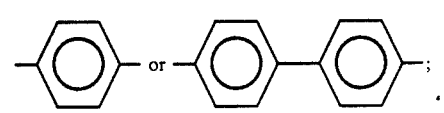

l is 1-12 and k is 1-4.

3. A liquid crystal composition according to claim 1, which further comprises at least one mesomorphic compounds represented by the following formula (III):

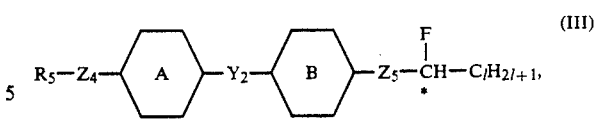

wherein R₅ denotes a linear or branched alkyl group having 1-18 carbon atoms capable of having a substituent; Y₂ denotes a single bond, —COO—, —OCO—, —COS—, —SCO—, —CH₂O—, —OCH₂— or —CH=CH—COO—; Z₄ denotes a single bond —O—, —COO— or —OCO—; Z₅ denotes —OCH₂—, —COOCH₂—, —OCO— or —O(CH₂)ₖO—CH₂—;

denotes

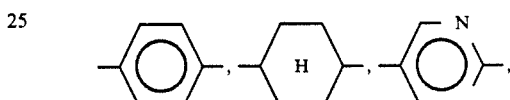

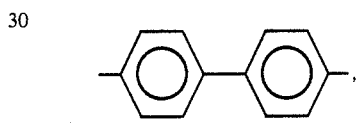

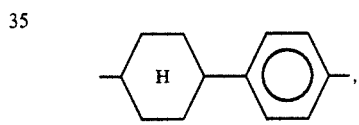

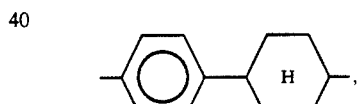

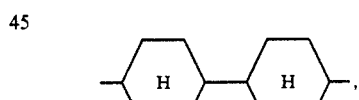

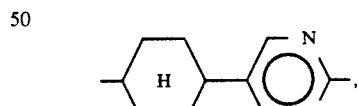

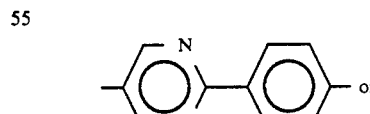

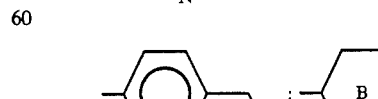

denotes

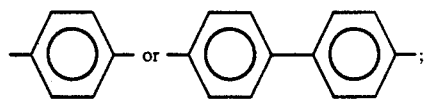

l is 1-12 and k is 1-4.

4. A liquid crystal device, comprising a pair of electrode plates and a liquid crystal composition according to claim 1 disposed between the electrode plates.

5. A liquid crystal device, comprising a pair of electrode plates and a liquid crystal composition according to claim 2 disposed between the electrode plates.

6. A liquid crystal device, comprising a pair of electrode plates and a liquid crystal composition according to claim 3 disposed between the electrode plates.

7. A liquid crystal composition according to claim 1, wherein a mesomorphic compound of the formula (I) is selected from a group consisting of the following compounds:

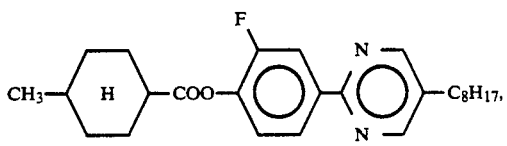

1-1

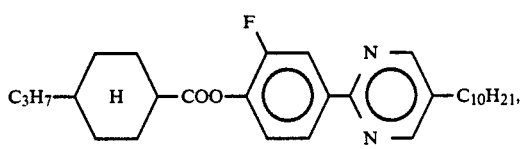

1-2

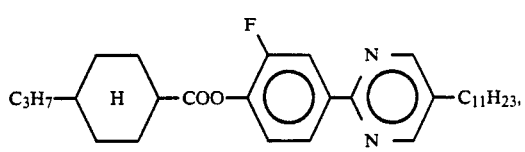

1-3

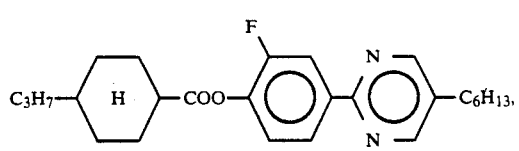

1-4

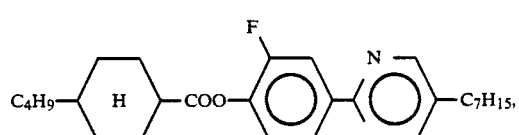

1-5

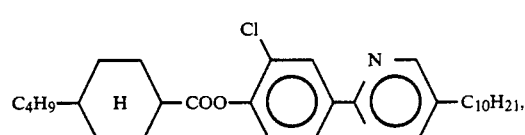

1-6

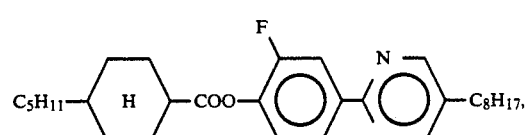

1-7

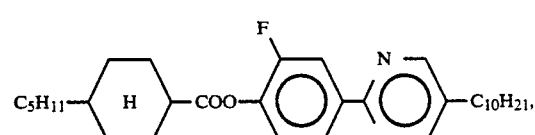

1-8

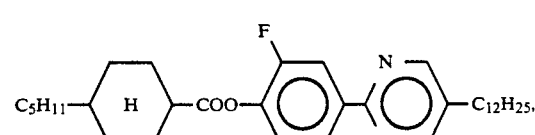

1-9

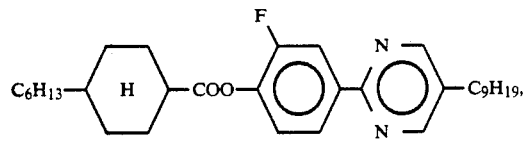  1-10
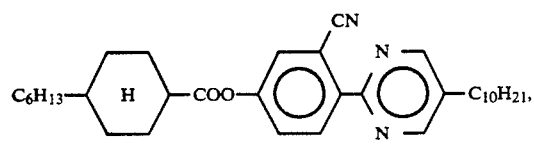  1-11
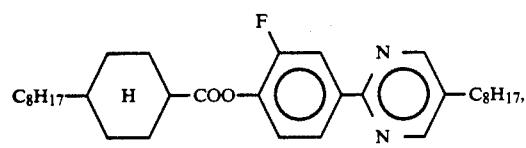  1-12
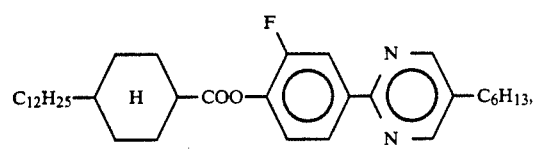  1-13
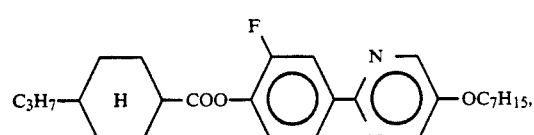  1-14
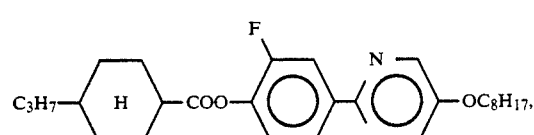  1-15
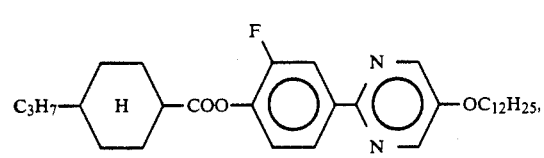  1-16
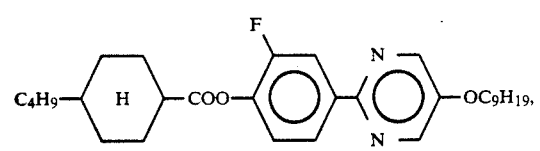  1-17
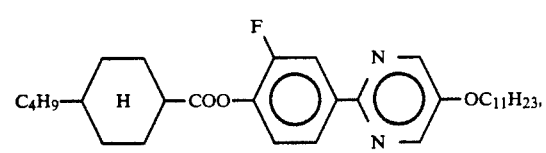  1-18
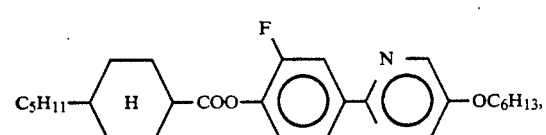  1-19
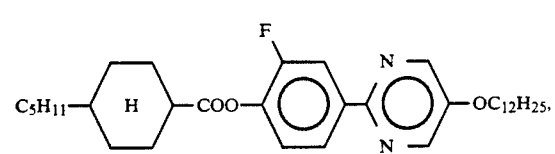  1-20

1-21
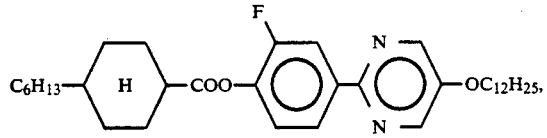
1-22
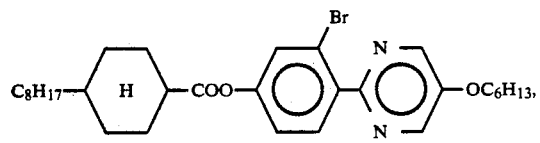
1-23
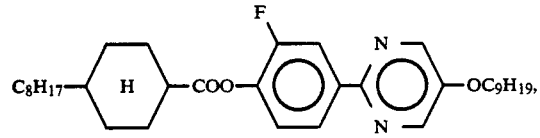
1-24
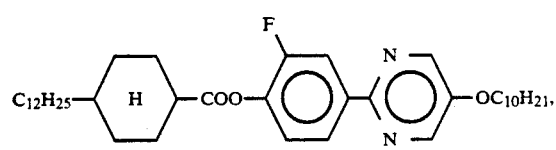
1-25
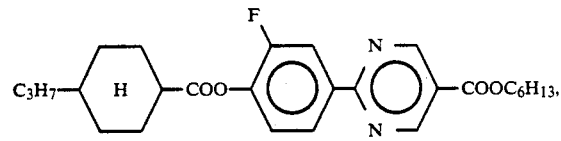
1-26
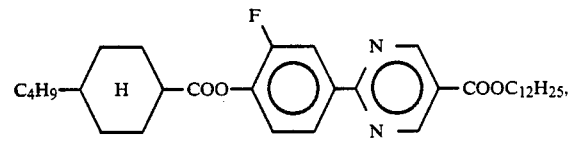
1-27
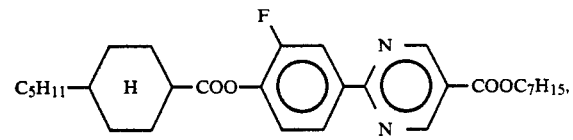
1-28
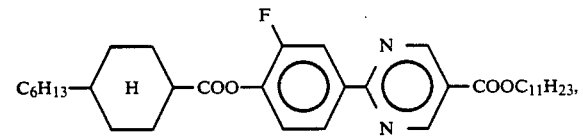
1-29
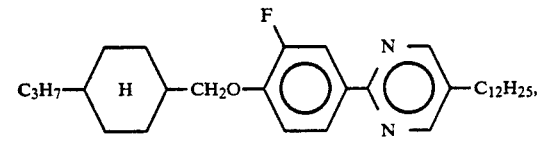
1-30
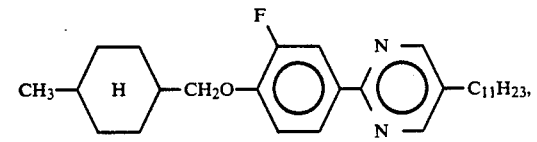
1-31
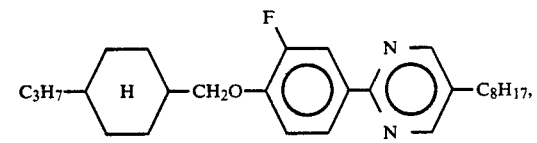

-continued
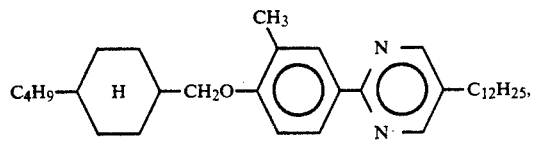 1-32
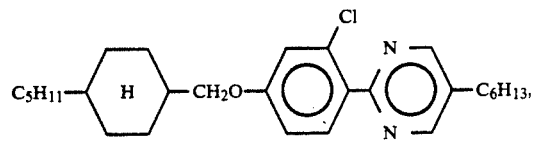 1-33
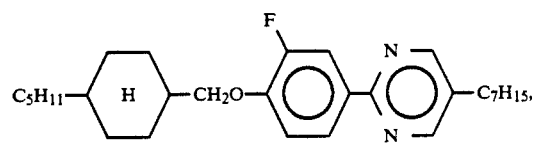 1-34
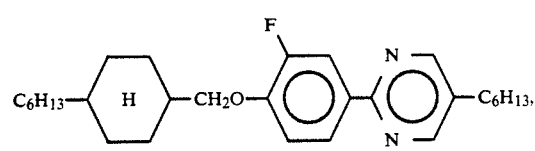 1-35
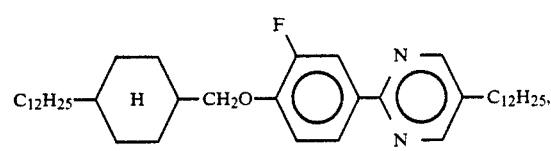 1-36
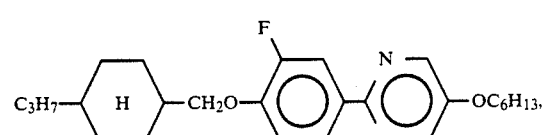 1-37
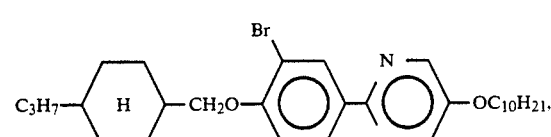 1-38
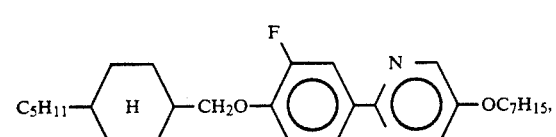 1-39
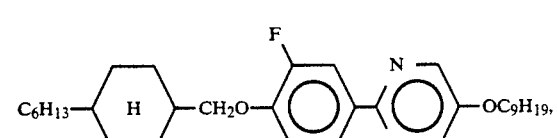 1-40
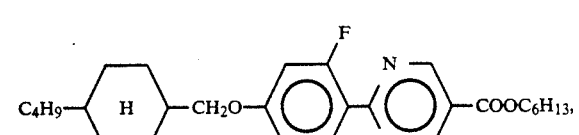 1-41
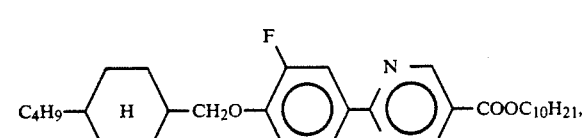 1-42

-continued
1-43
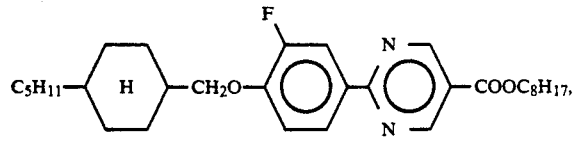
1-44
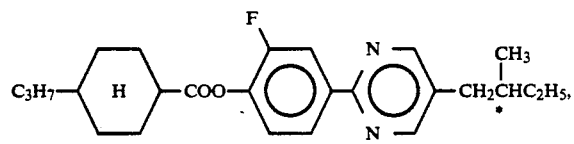
1-45
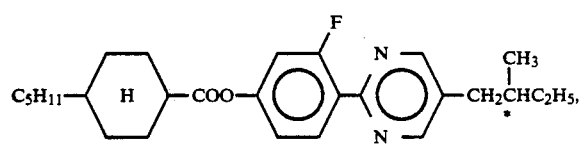
1-46
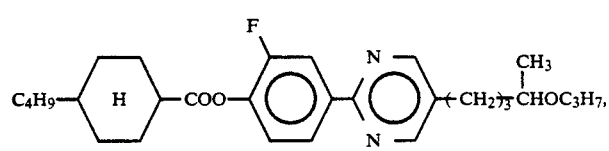
1-47
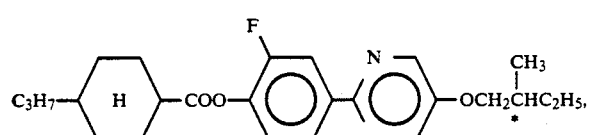
1-48
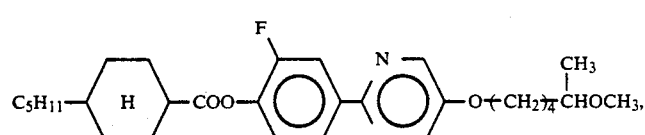
1-49
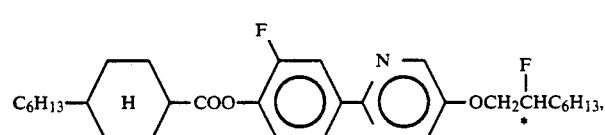
1-50
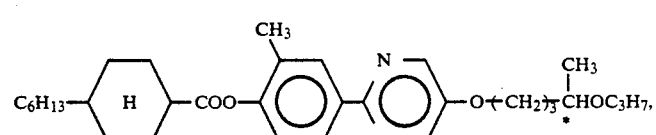
1-51
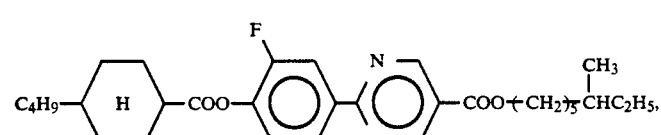
1-52
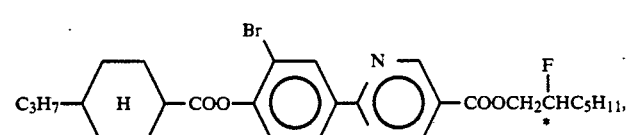
1-53
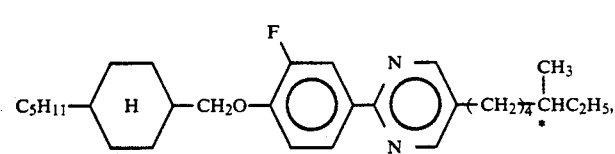

-continued
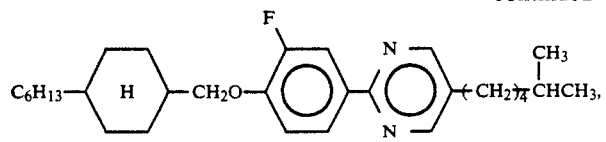
1-54
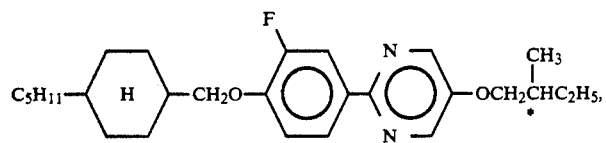
1-55
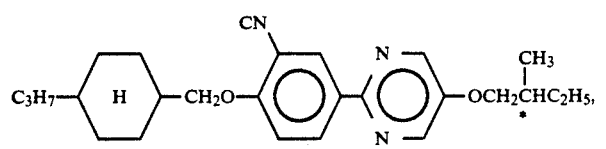
1-56
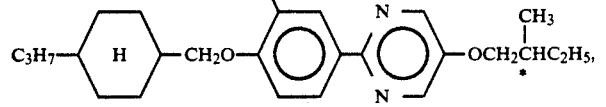
1-57
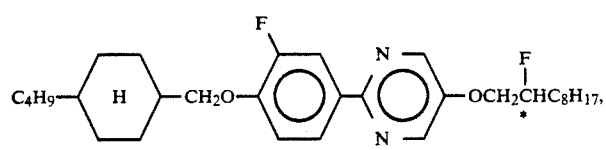
1-58
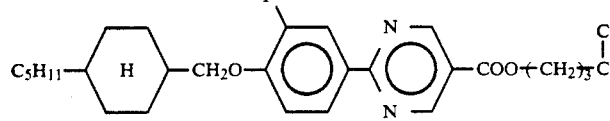
1-59
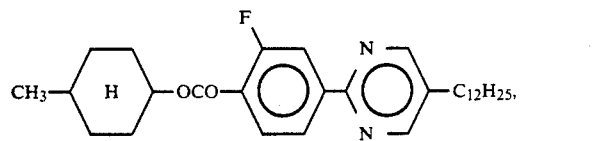
1-60
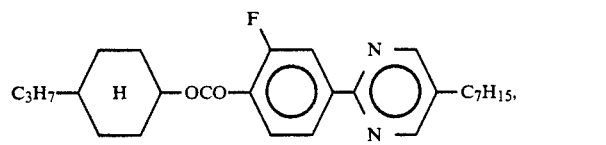
1-61
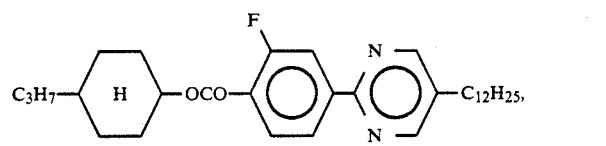
1-62
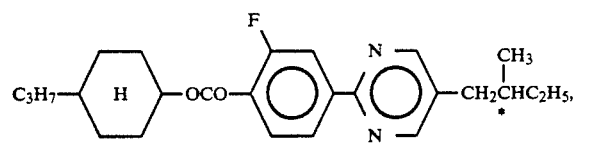
1-63
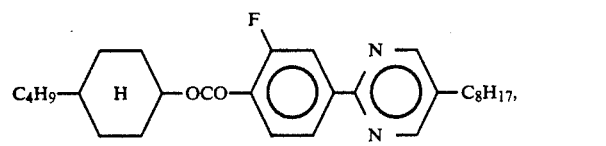
1-64
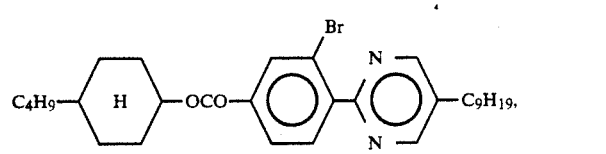

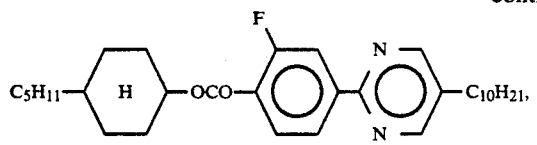
1-65
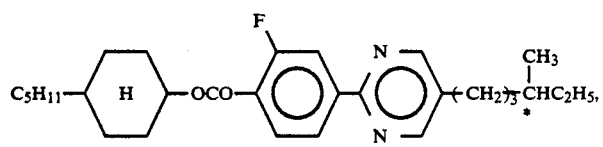
1-66
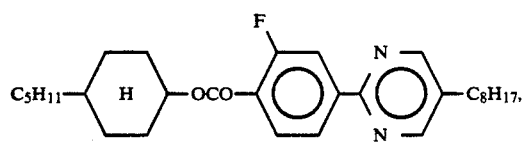
1-67
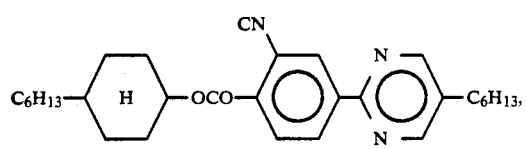
1-68
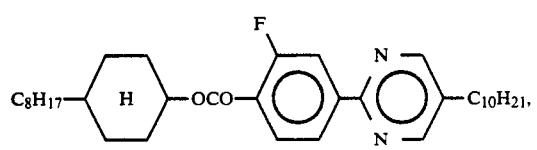
1-69
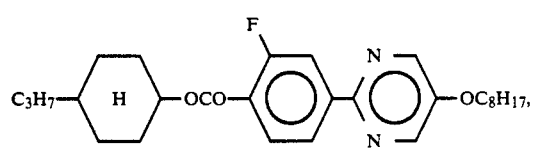
1-70
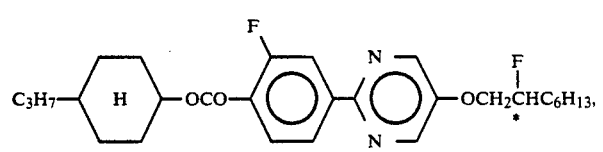
1-71
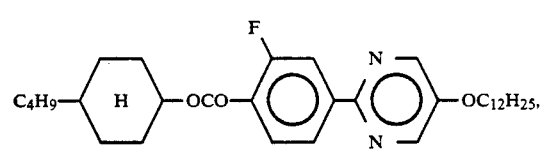
1-72
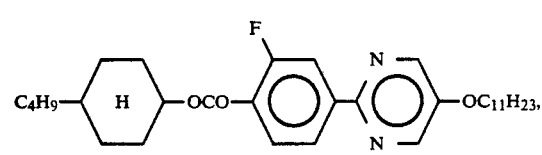
1-73
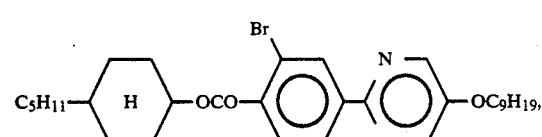
1-74
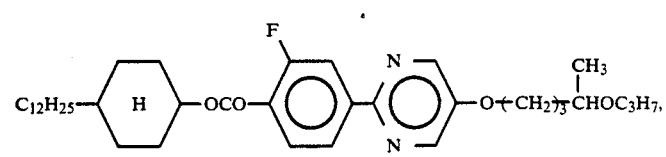
1-75

-continued
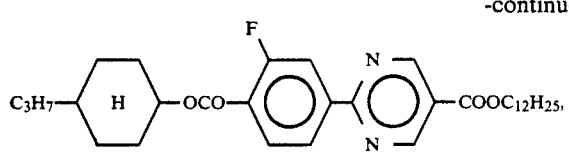
1-76
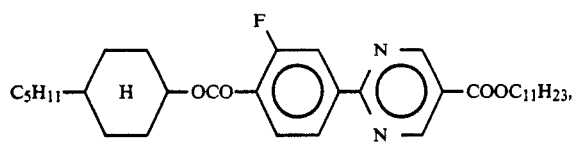
1-77
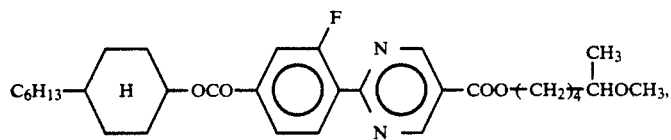
1-78
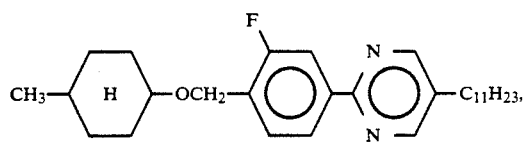
1-79
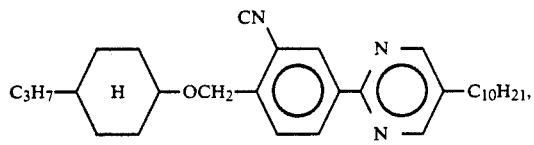
1-80
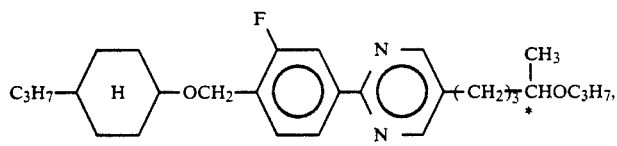
1-81
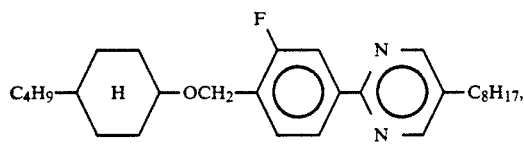
1-82
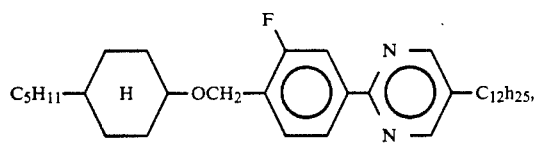
1-83
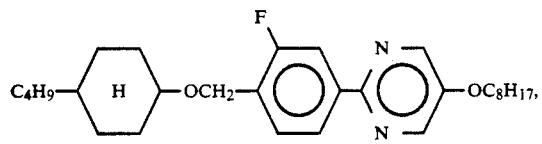
1-84
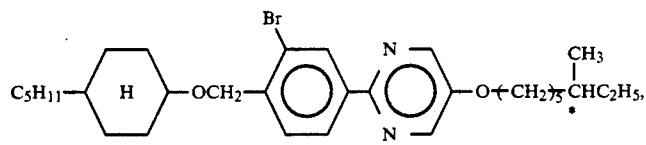
1-85
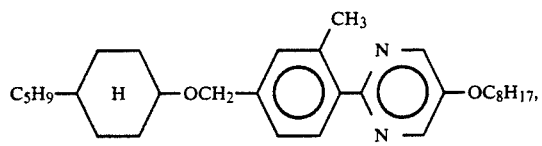
1-86

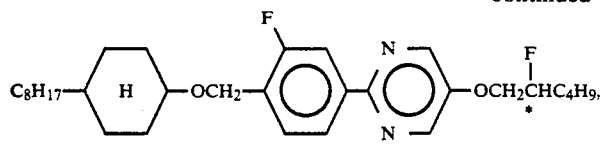
1-87
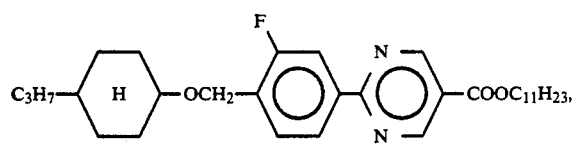
1-88
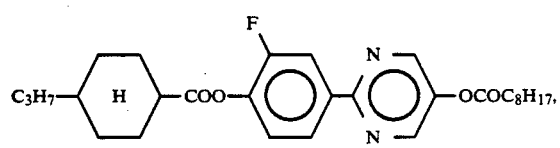
1-89
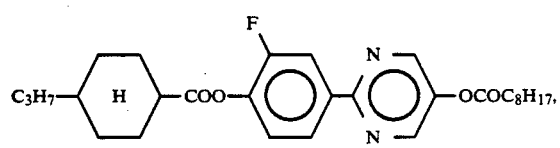
1-90
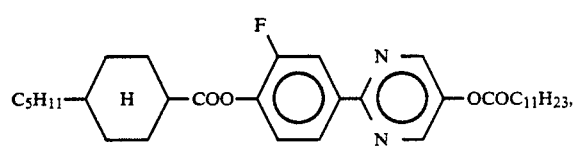
1-91
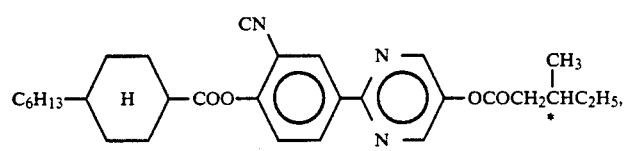
1-92
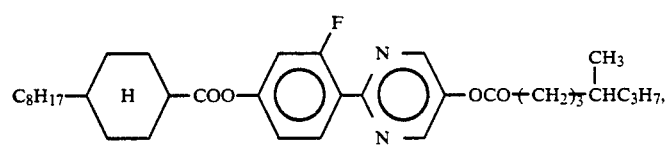
1-93
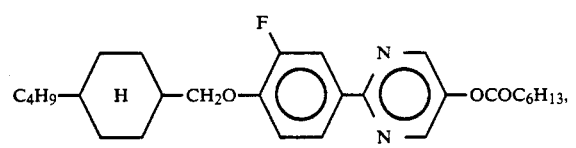
1-94
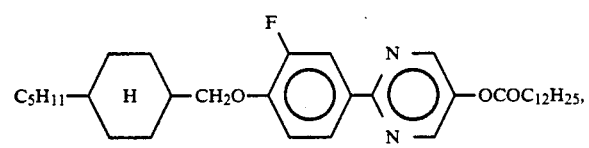
1-95
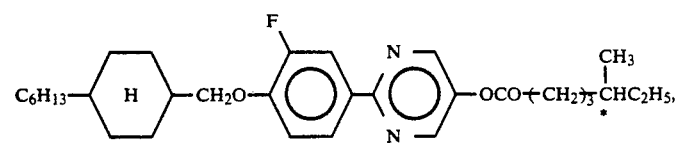
1-96
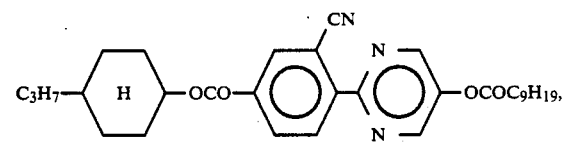
1-97
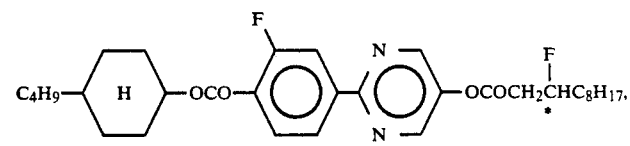

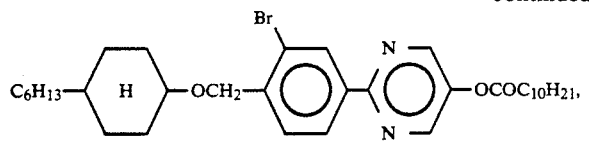
1-98
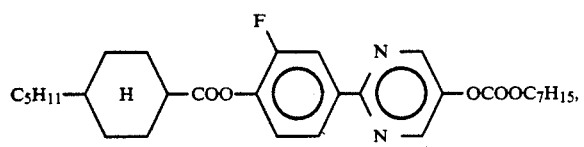
1-99
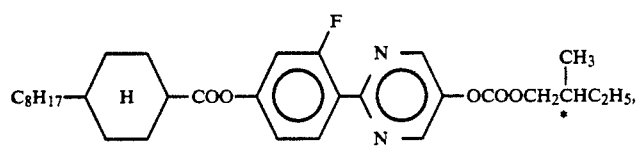
1-100
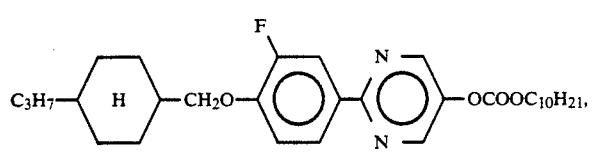
1-101
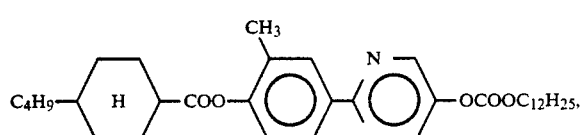
1-102
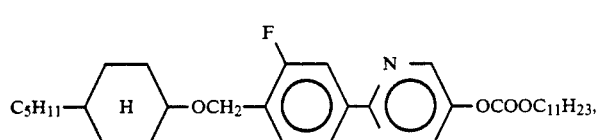
1-103
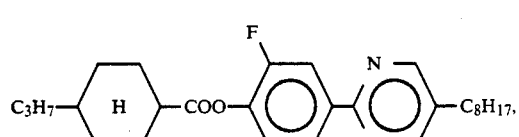
1-104
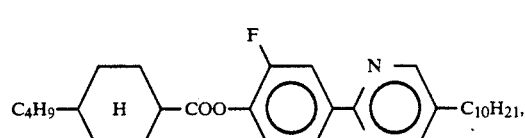
1-105
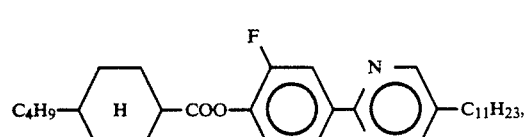
1-106
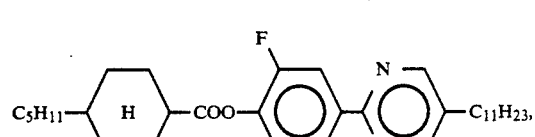
1-107
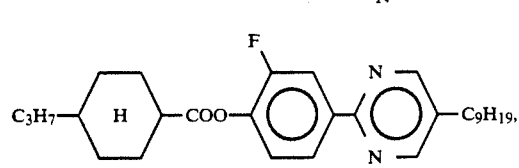
1-108

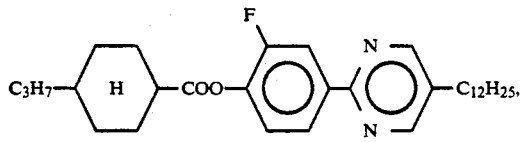
1-109
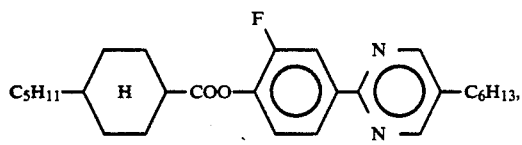
1-110
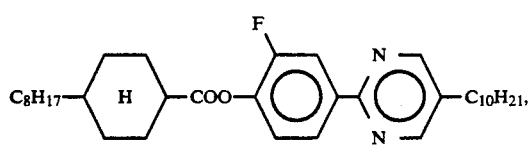
1-111
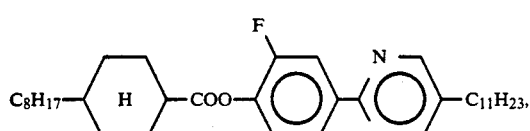
1-112
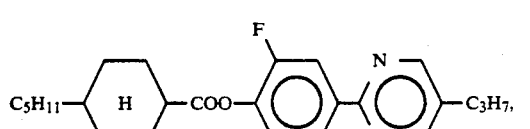
1-113
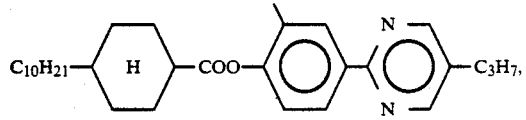
1-114
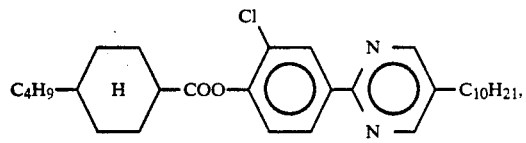
1-115
and
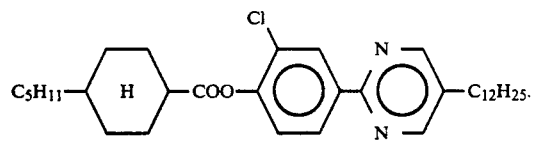
1-116
8. A liquid crystal device, comprising a pair of electrode plates and a liquid crystal composition according to claim 7 disposed between said electrode plates.
9. A liquid crystal composition according claim 2, wherein a mesomorphic compound of the formula (I) is selected from a group consisting of the following compounds:
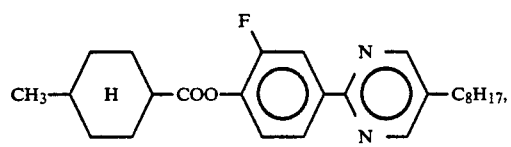
1-1
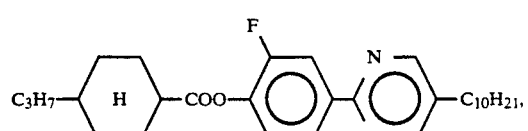
1-2

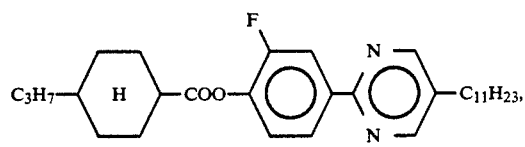  1-3
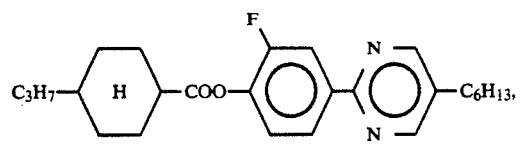  1-4
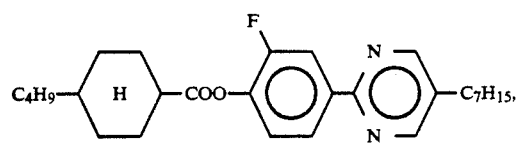  1-5
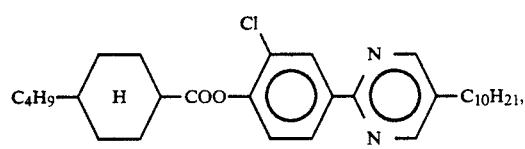  1-6
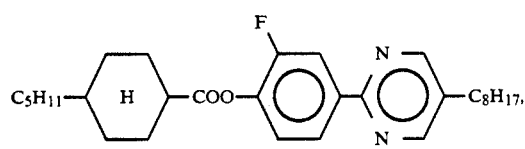  1-7
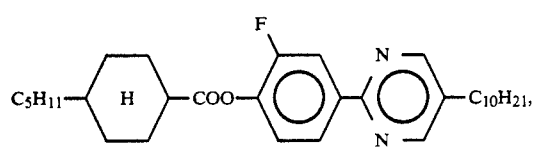  1-8
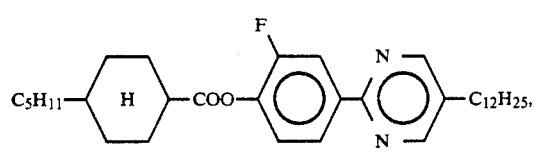  1-9
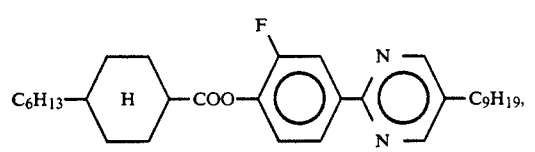  1-10
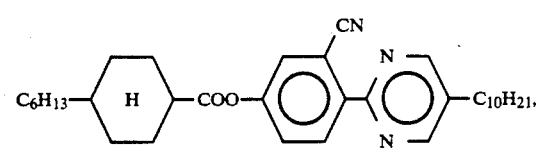  1-11
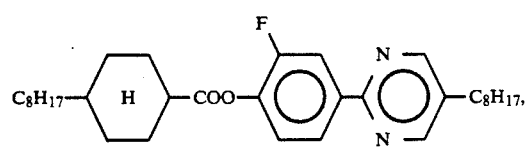  1-12
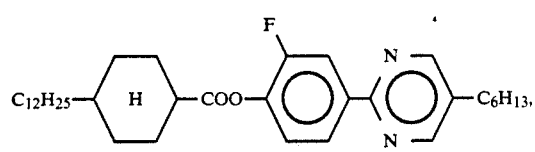  1-13

-continued
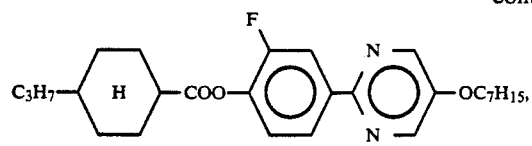 1-14
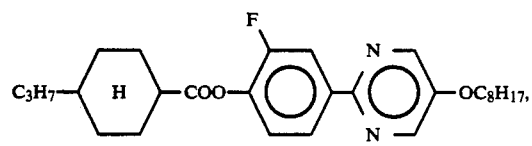 1-15
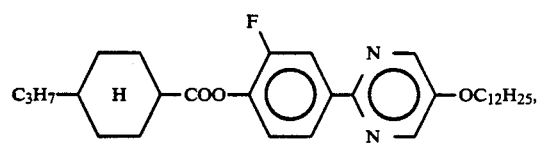 1-16
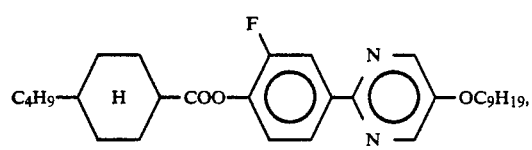 1-17
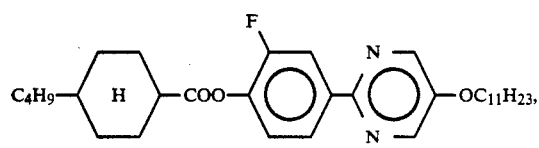 1-18
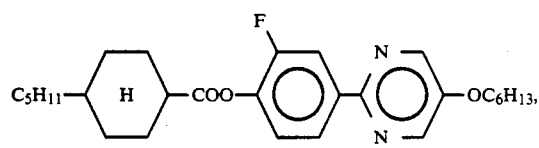 1-19
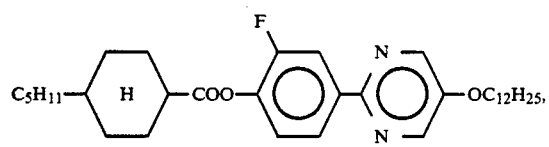 1-20
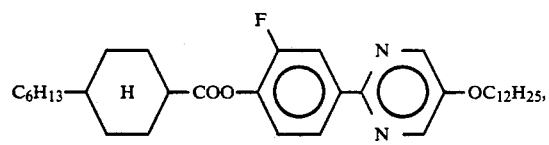 1-21
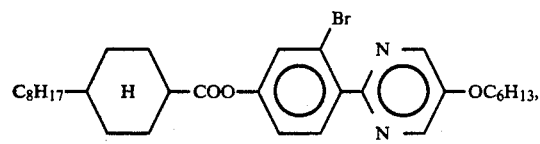 1-22
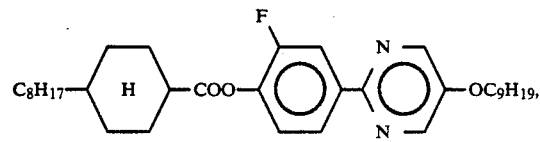 1-23
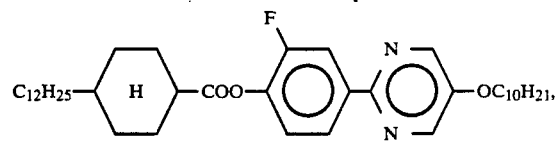 1-24

-continued
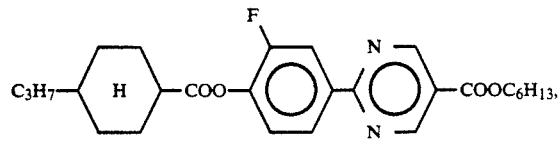 1-25
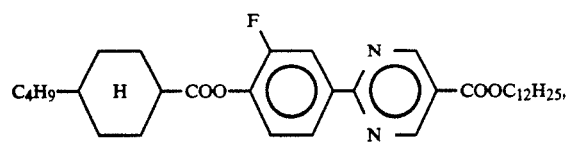 1-26
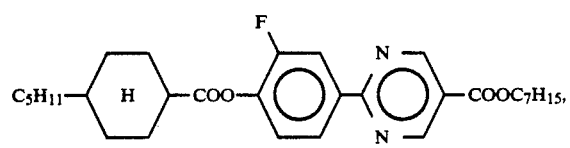 1-27
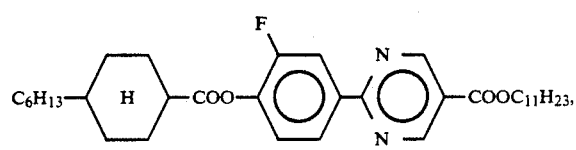 1-28
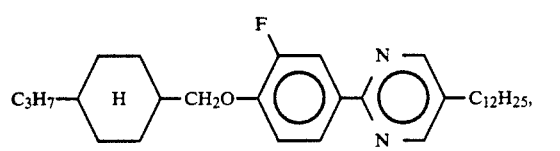 1-29
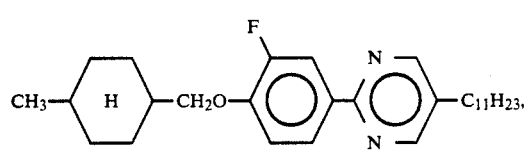 1-30
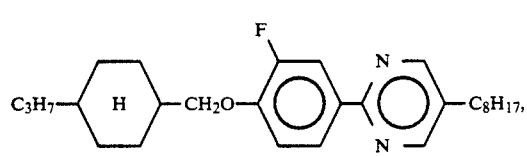 1-31
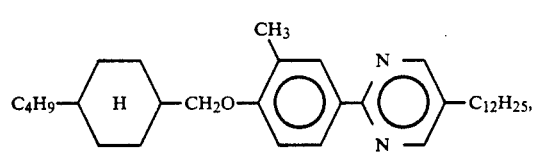 1-32
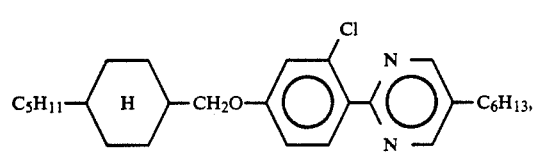 1-33
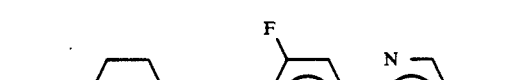 1-34
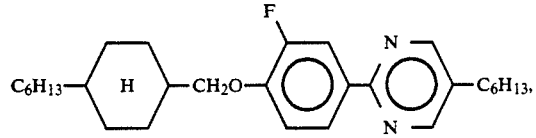 1-35

-continued
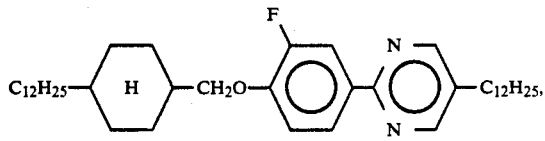 1-36
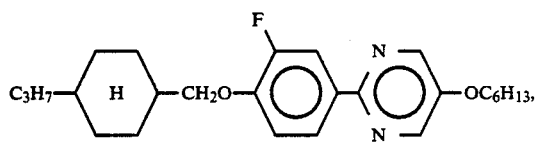 1-37
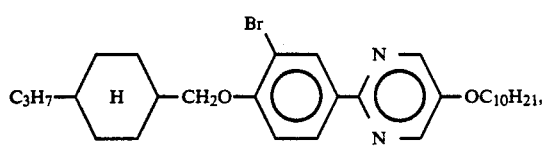 1-38
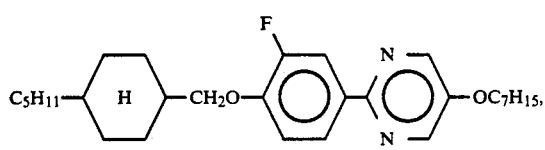 1-39
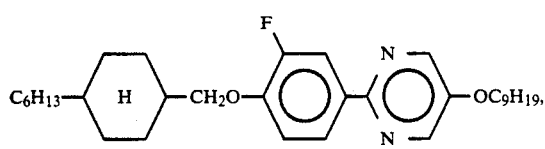 1-40
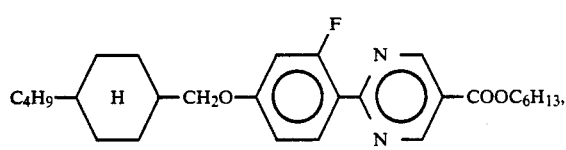 1-41
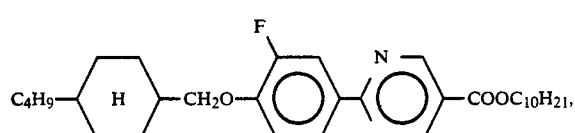 1-42
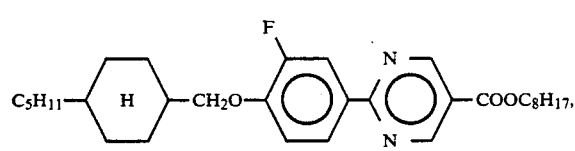 1-43
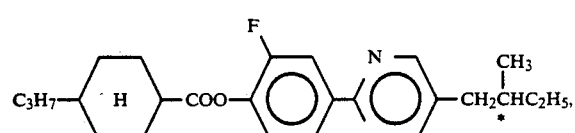 1-44
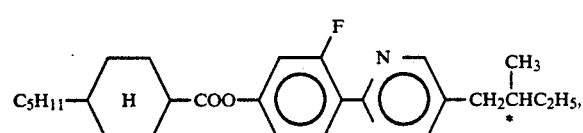 1-45
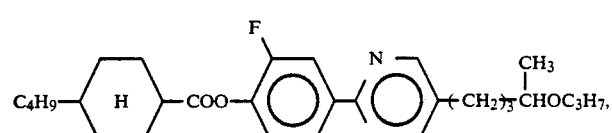 1-46

-continued
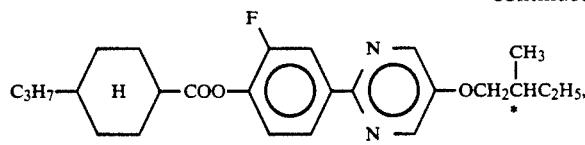 1-47
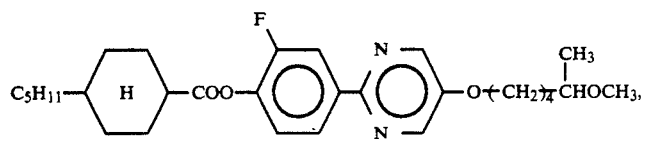 1-48
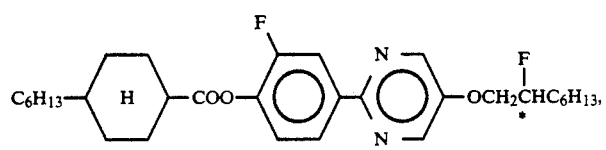 1-49
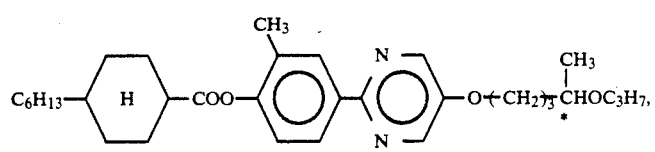 1-50
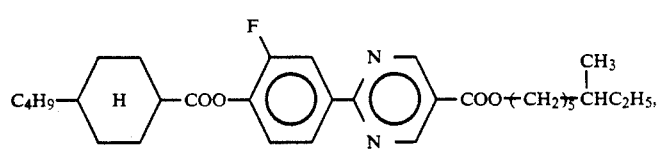 1-51
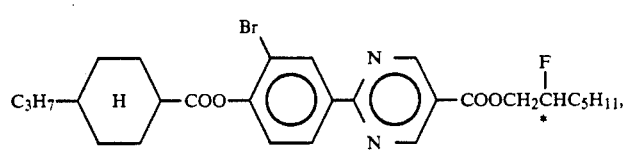 1-52
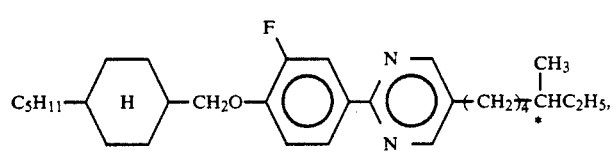 1-53
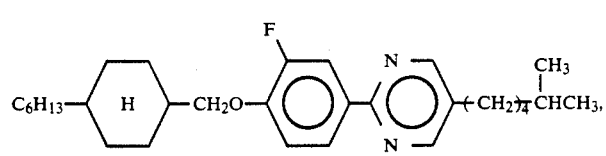 1-54
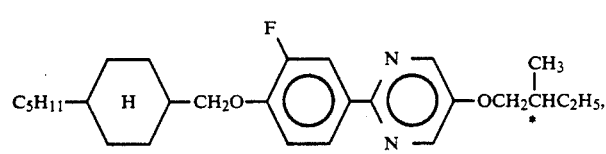 1-55
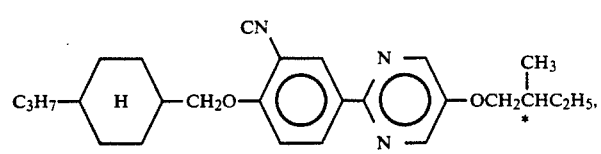 1-56
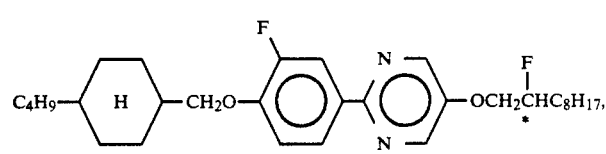 1-57

-continued
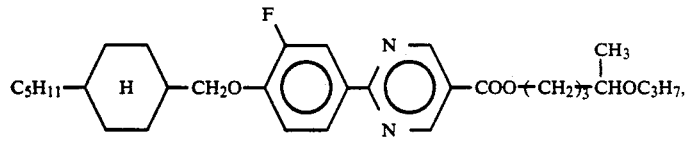
1-58
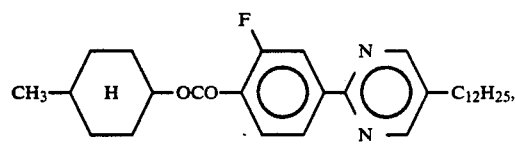
1-59
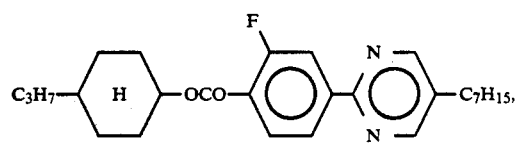
1-60
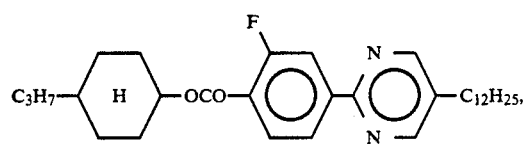
1-61
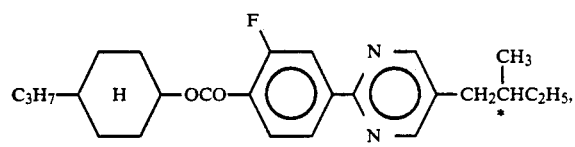
1-62
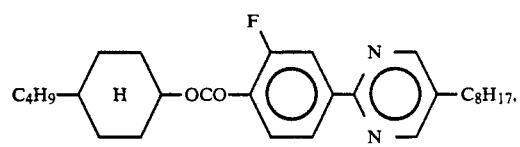
1-63
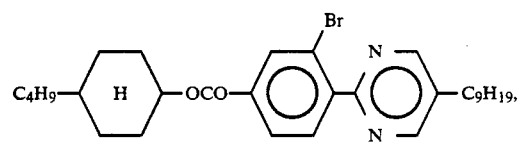
1-64
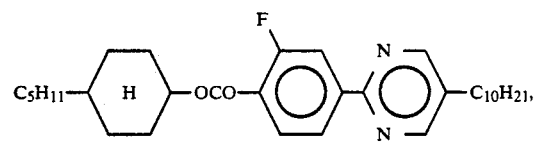
1-65
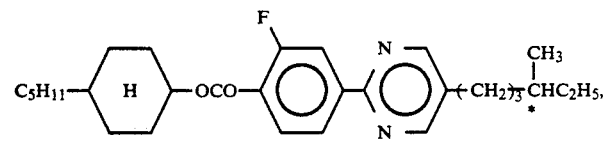
1-66
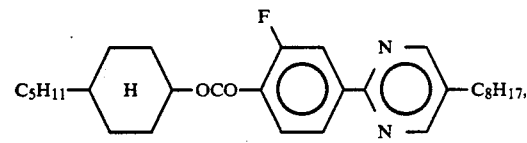
1-67
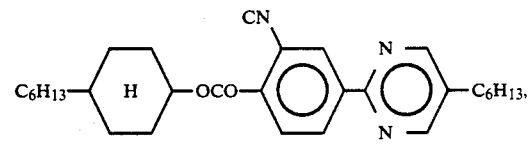
1-68

-continued
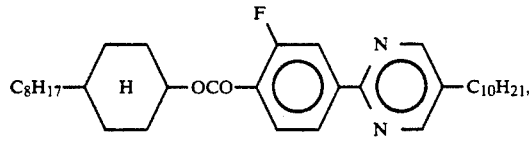 1-69
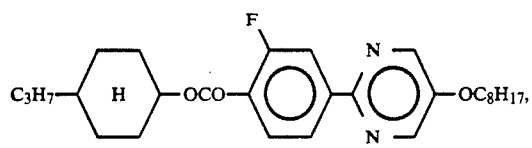 1-70
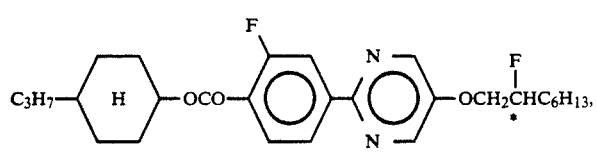 1-71
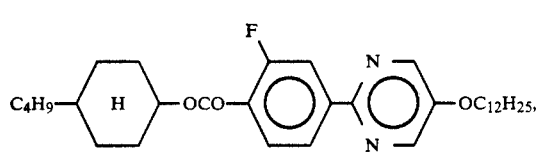 1-72
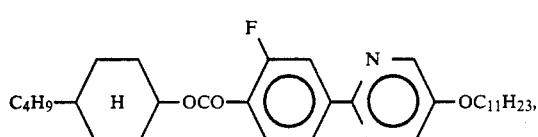 1-73
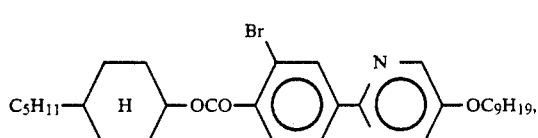 1-74
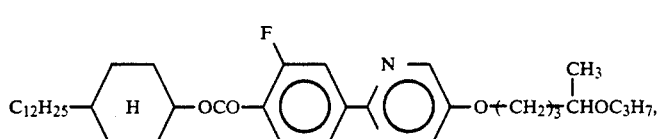 1-75
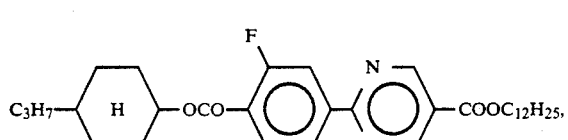 1-76
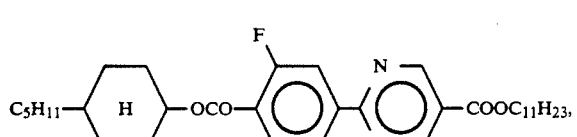 1-77
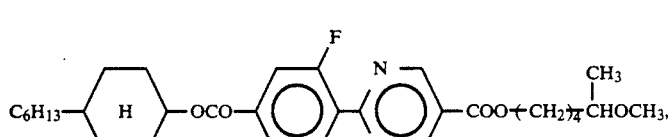 1-78
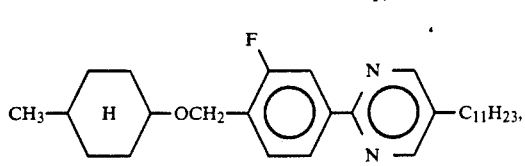 1-79

-continued
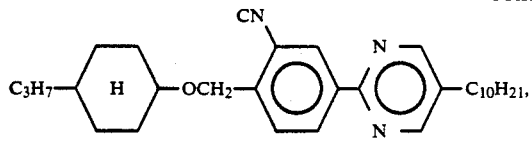 1-80
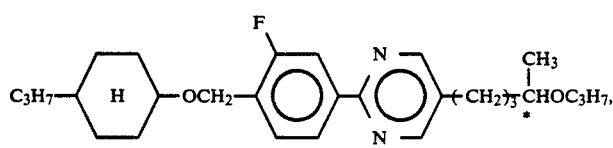 1-81
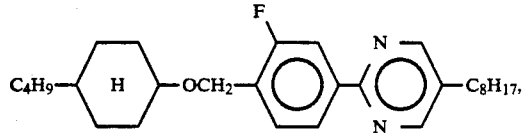 1-82
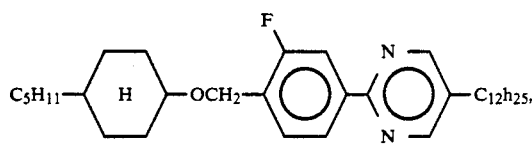 1-83
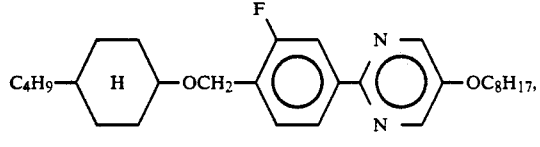 1-84
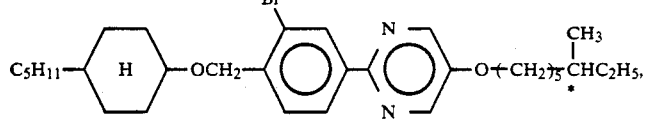 1-85
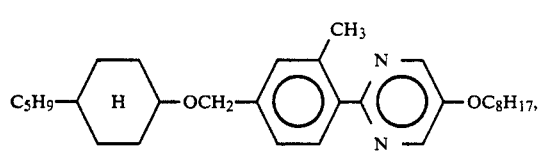 1-86
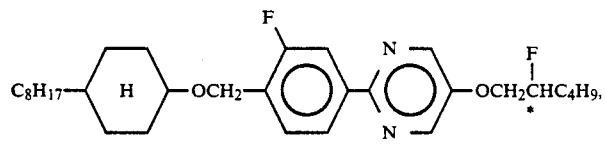 1-87
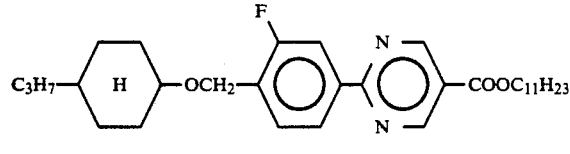 1-88
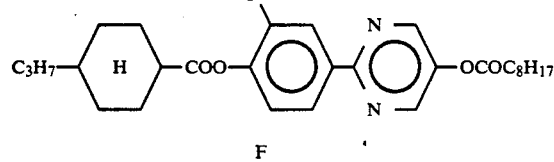 1-89
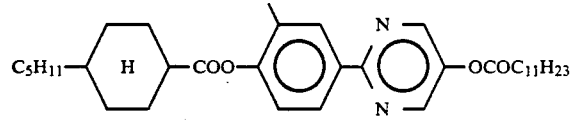 1-90

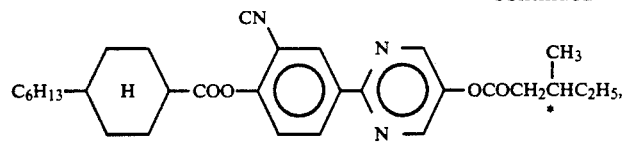
1-91
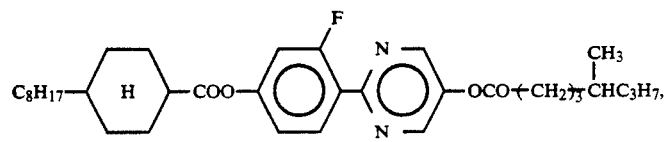
1-92
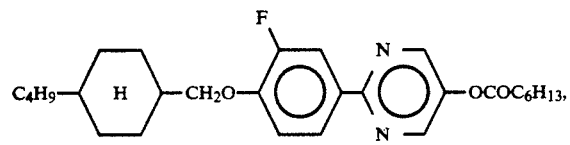
1-93
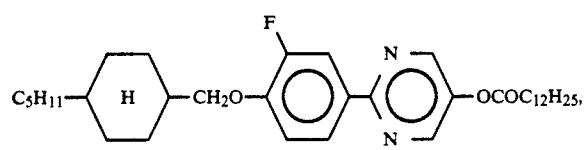
1-94
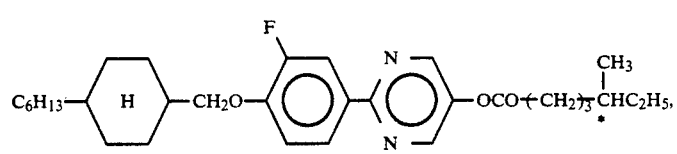
1-95
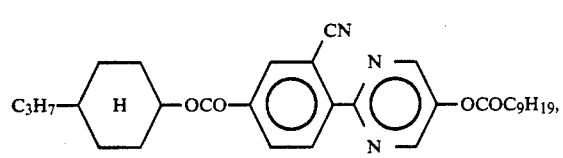
1-96
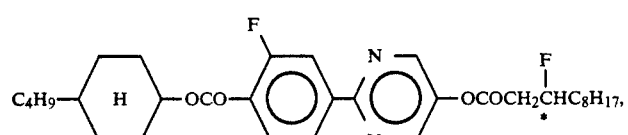
1-97
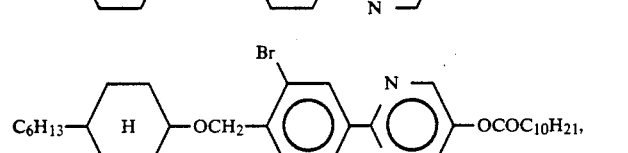
1-98
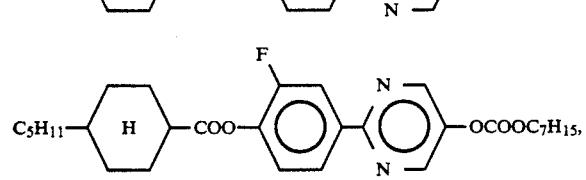
1-99
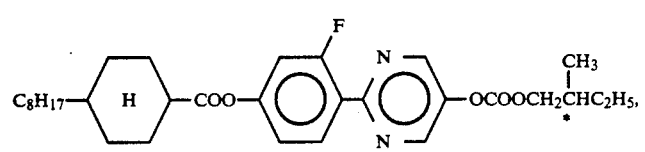
1-100
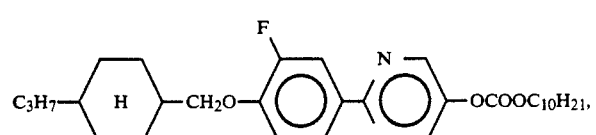
1-101

-continued
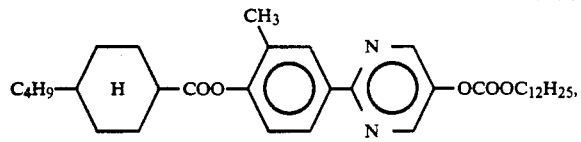 1-102
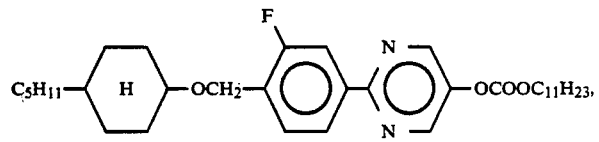 1-103
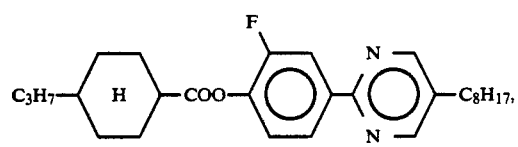 1-104
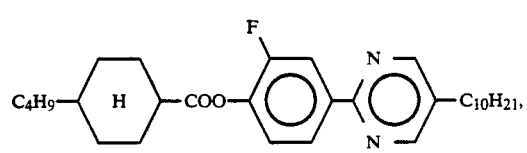 1-105
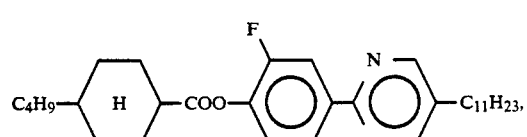 1-106
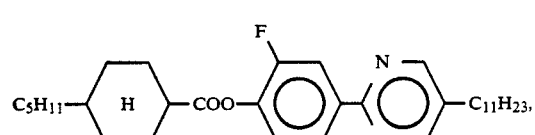 1-107
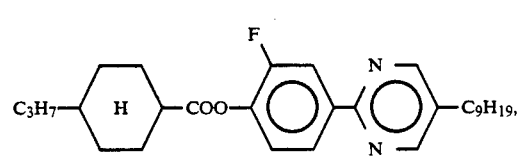 1-108
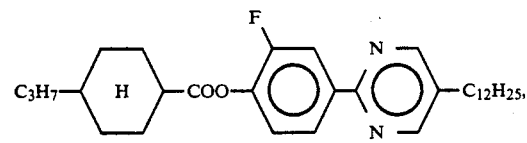 1-109
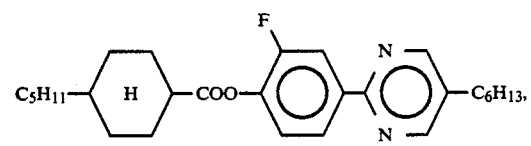 1-110
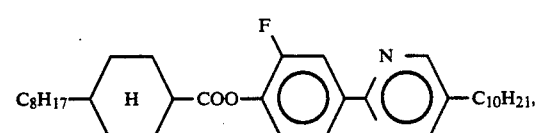 1-111
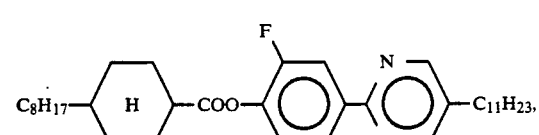 1-112

-continued
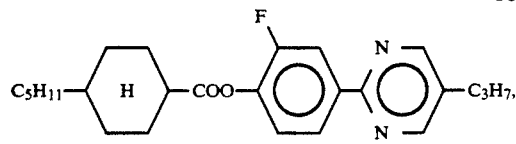 1-113
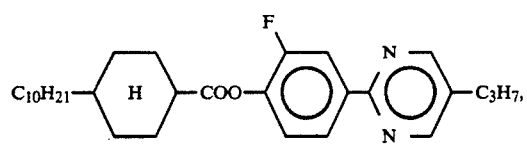 1-114
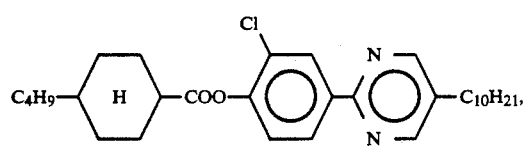 1-115
and
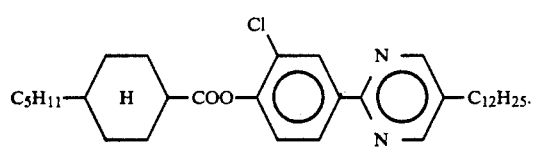 1-116
10. A liquid crystal device, comprising a pair of electrode plates and a liquid crystal composition according to claim 9 disposed between said electrode plates.
11. A liquid crystal composition according to claim 3, wherein a mesomorphic compound of the formula (I) is selected from a group consisting of the following compounds:
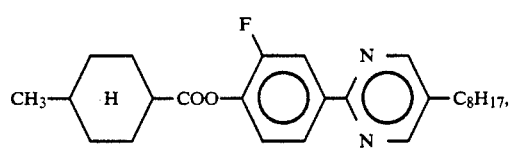 1-1
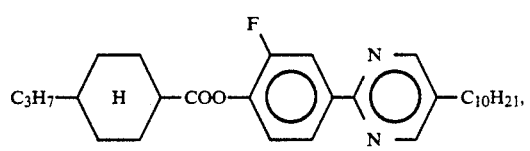 1-2
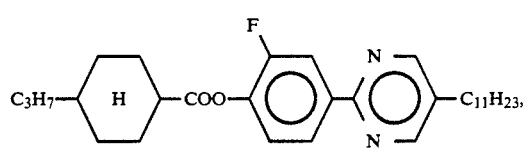 1-3
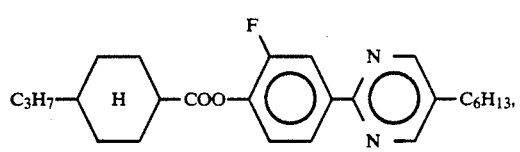 1-4
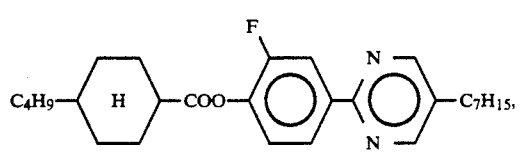 1-5
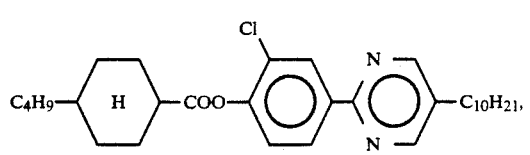 1-6

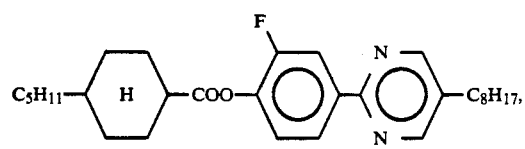
1-7
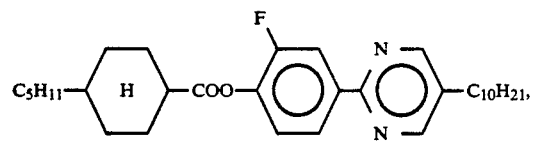
1-8
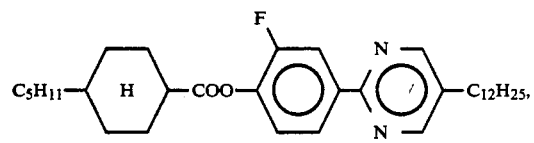
1-9
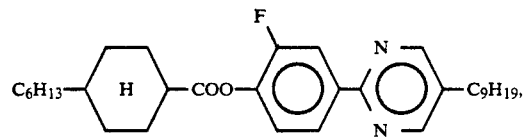
1-10
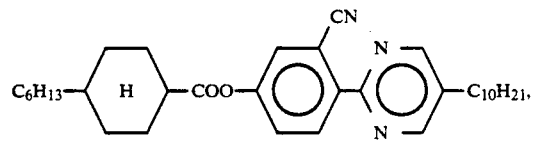
1-11
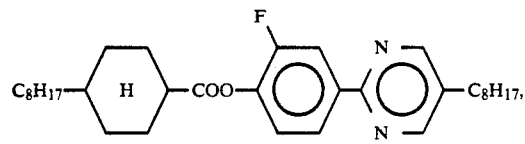
1-12
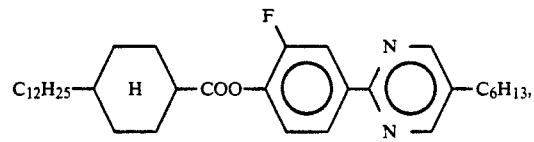
1-13
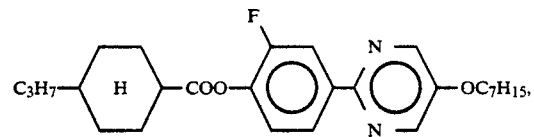
1-14
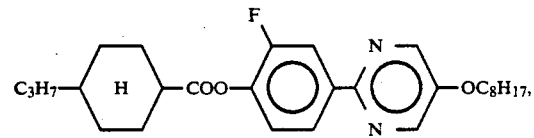
1-15
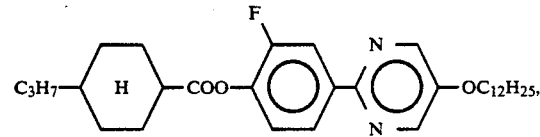
1-16
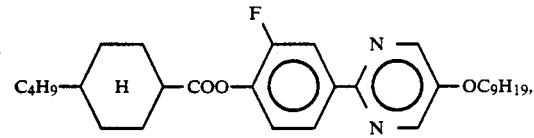
1-17

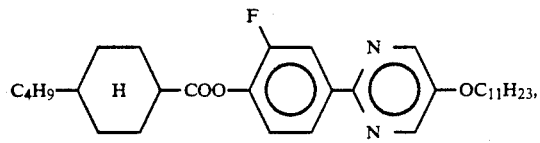
1-18
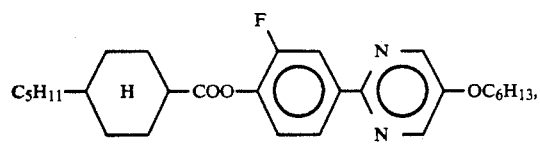
1-19
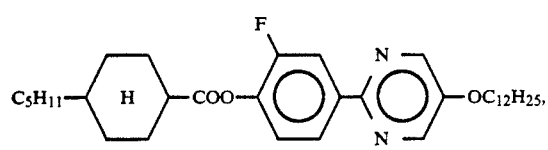
1-20
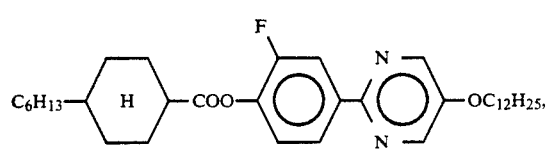
1-21
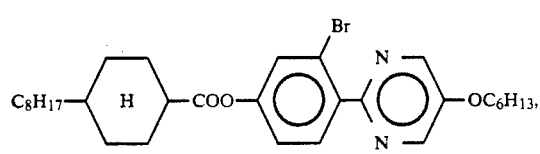
1-22
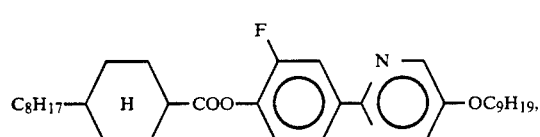
1-23
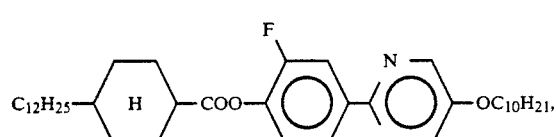
1-24
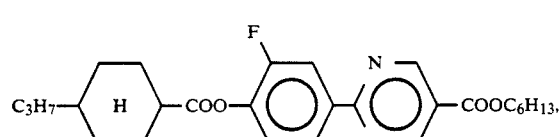
1-25
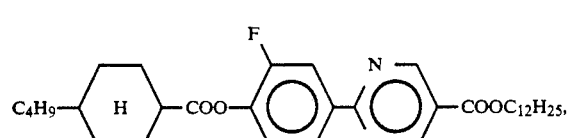
1-26
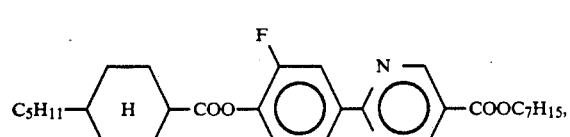
1-27
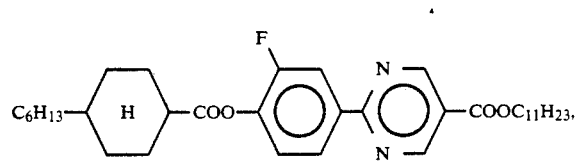
1-28

-continued
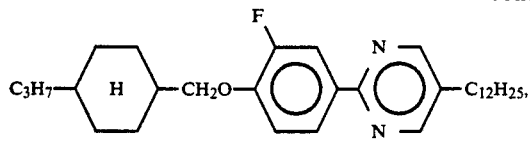
1-29
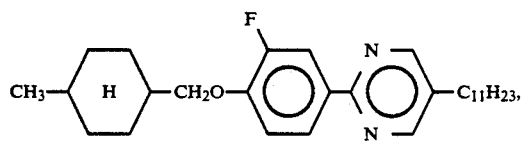
1-30
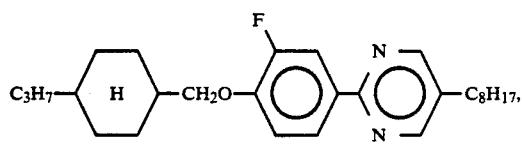
1-31
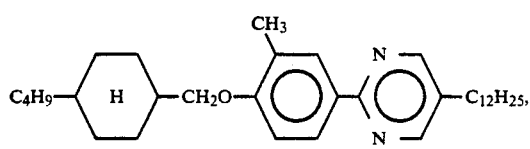
1-32
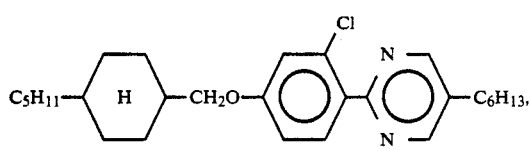
1-33
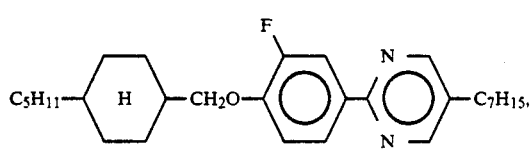
1-34
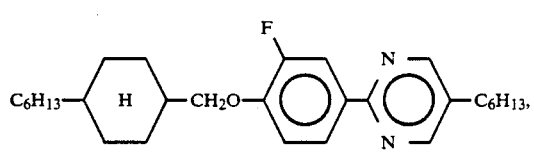
1-35
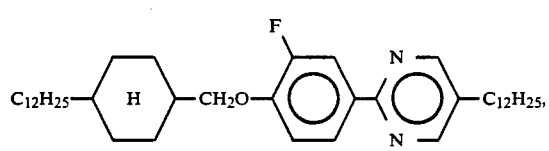
1-36
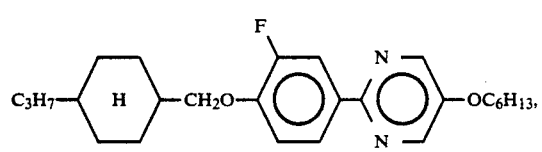
1-37
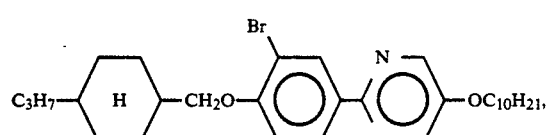
1-38
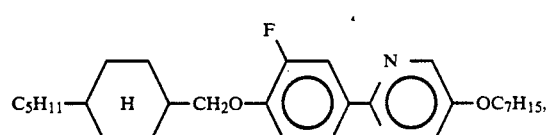
1-39

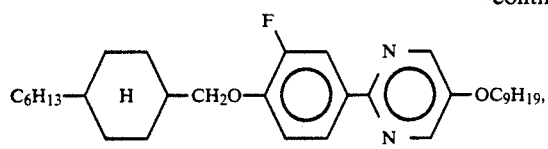
1-40
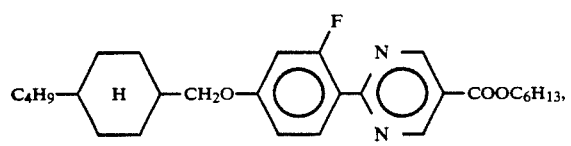
1-41
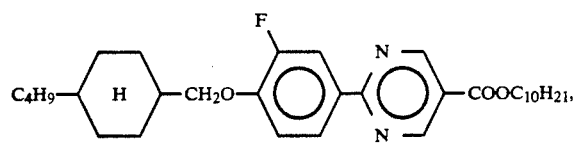
1-42
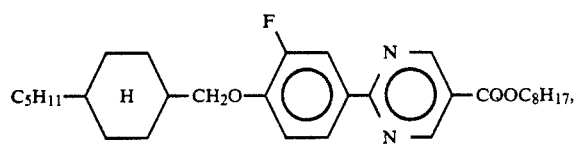
1-43
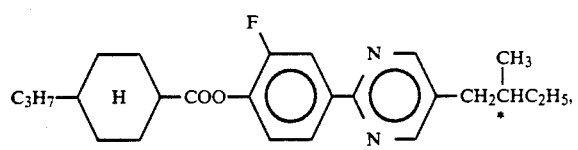
1-44
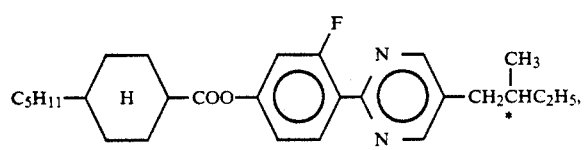
1-45
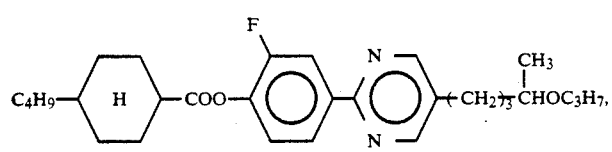
1-46
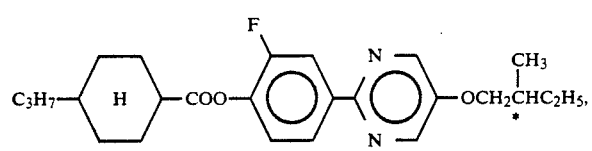
1-47
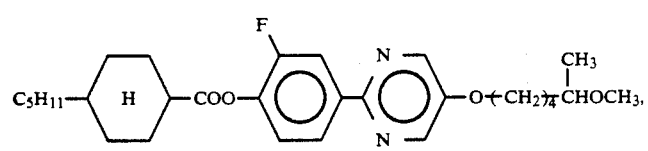
1-48
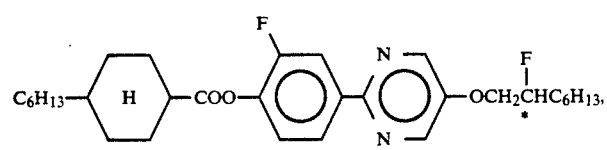
1-49
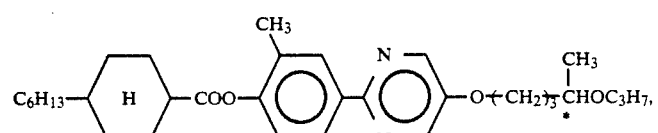
1-50

-continued
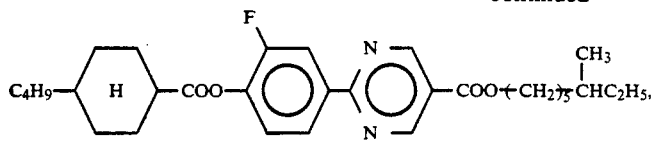 1-51
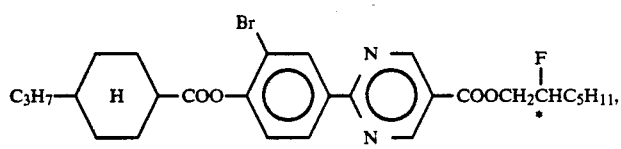 1-52
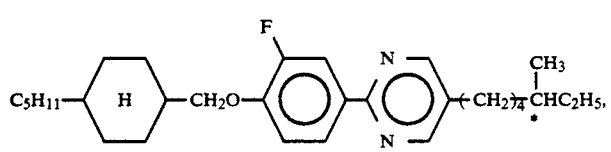 1-53
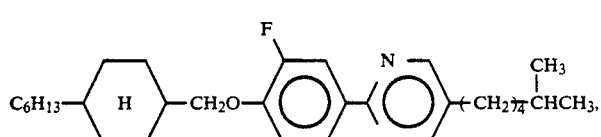 1-54
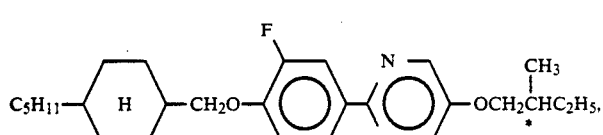 1-55
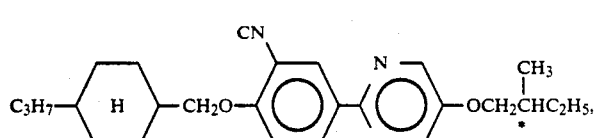 1-56
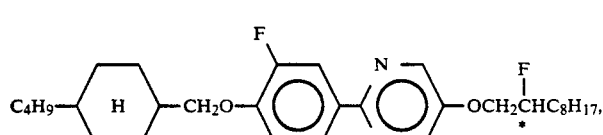 1-57
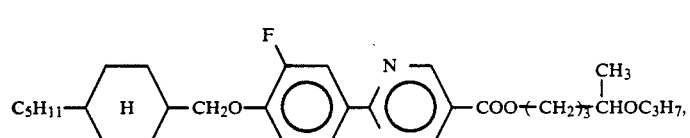 1-58
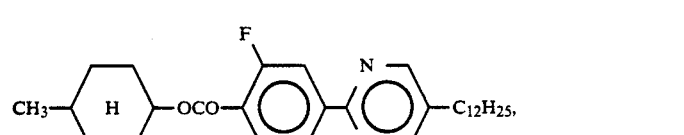 1-59
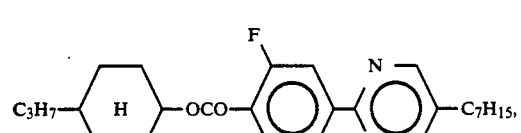 1-60
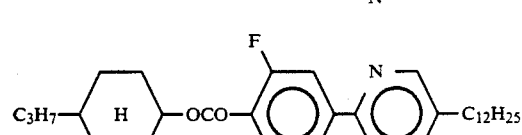 1-61

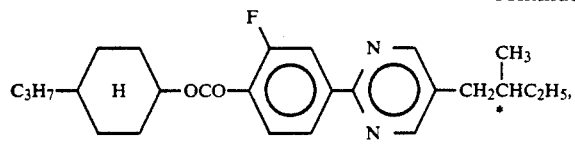 1-62
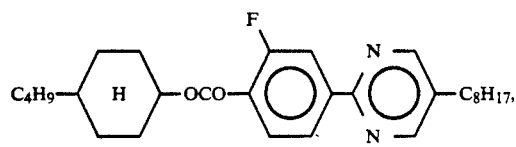 1-63
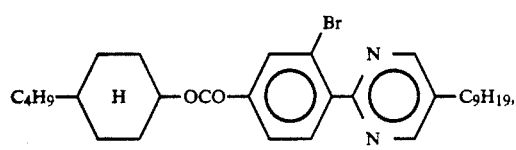 1-64
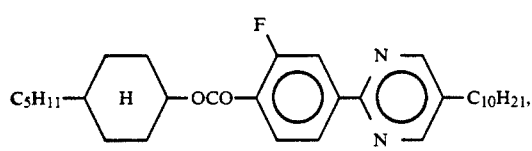 1-65
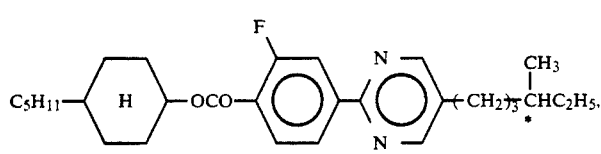 1-66
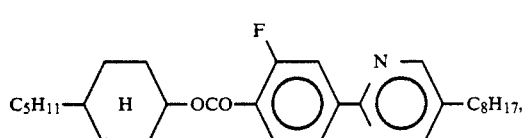 1-67
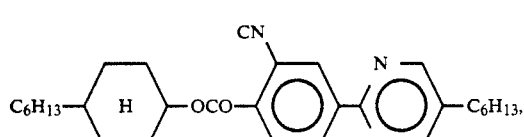 1-68
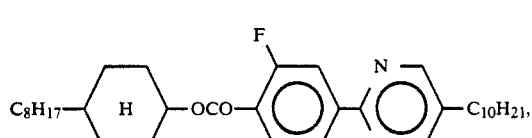 1-69
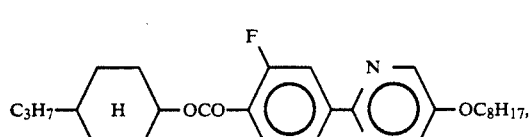 1-70
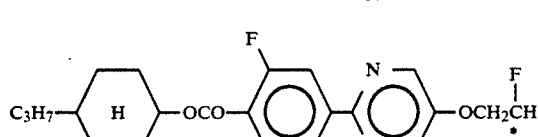 1-71
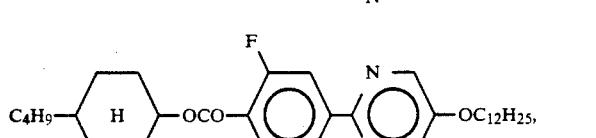 1-72

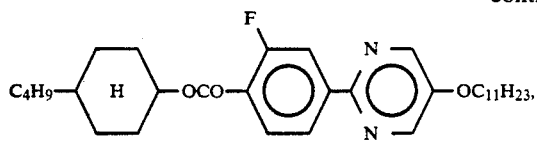 1-73
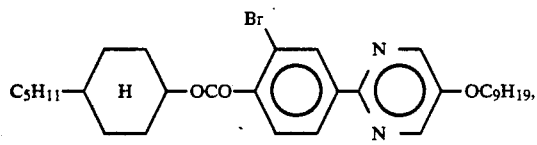 1-74
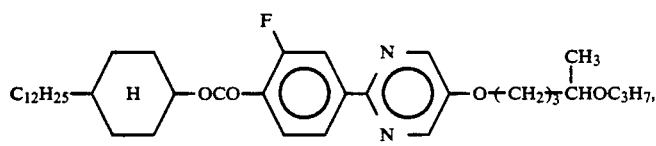 1-75
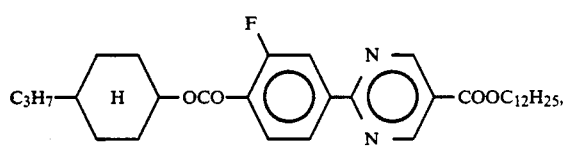 1-76
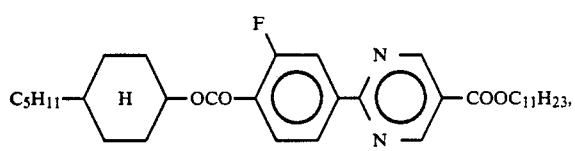 1-77
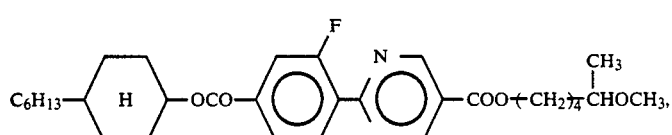 1-78
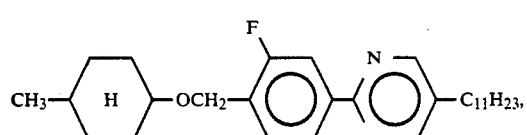 1-79
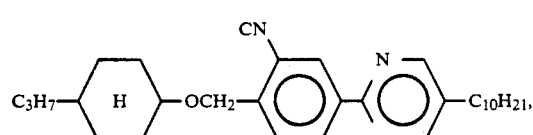 1-80
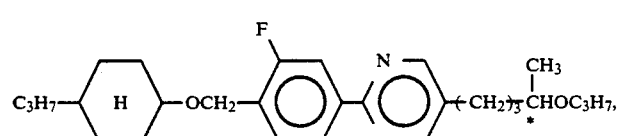 1-81
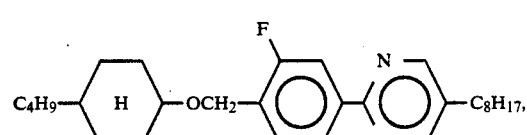 1-82
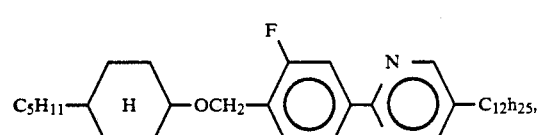 1-83

-continued
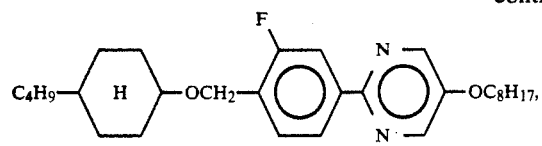 1-84
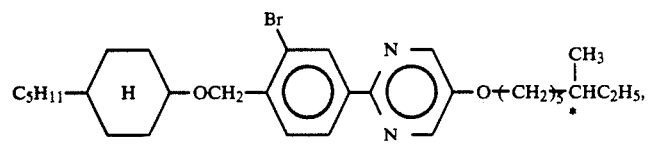 1-85
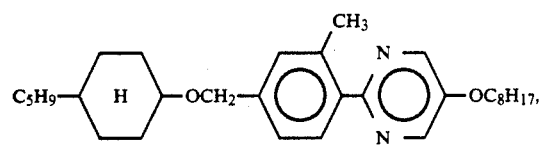 1-86
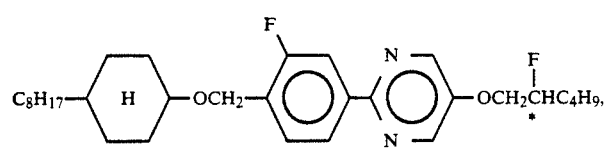 1-87
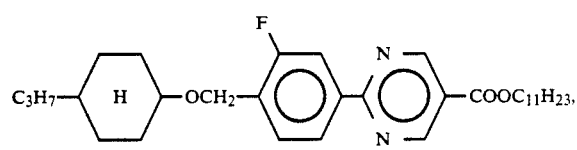 1-88
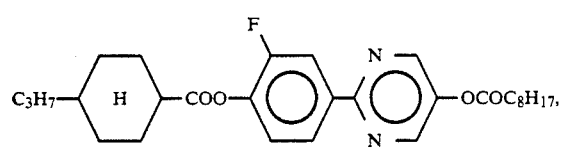 1-89
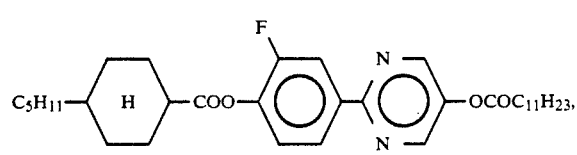 1-90
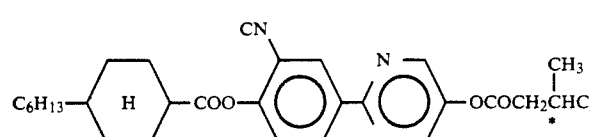 1-91
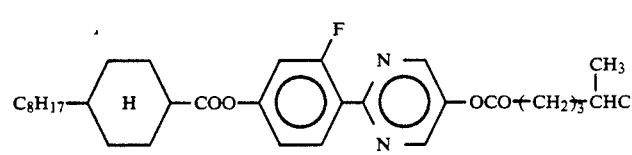 1-92
 1-93
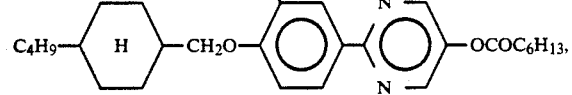 1-94
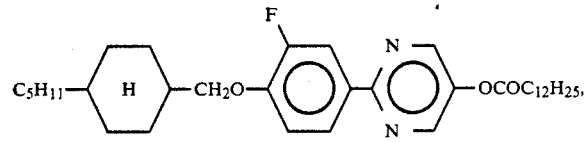

-continued
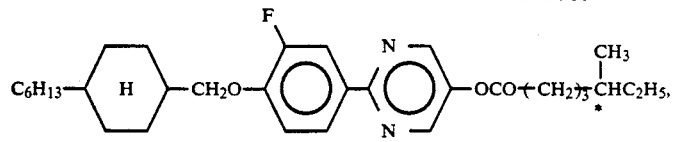 1-95
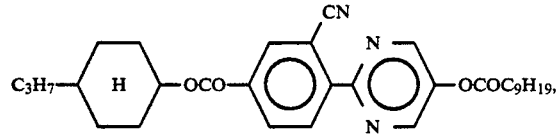 1-96
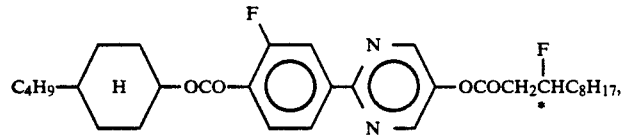 1-97
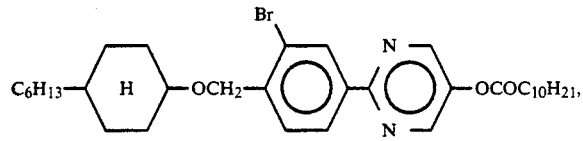 1-98
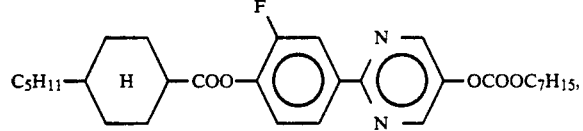 1-99
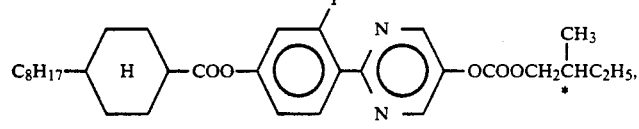 1-100
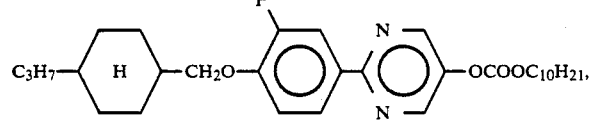 1-101
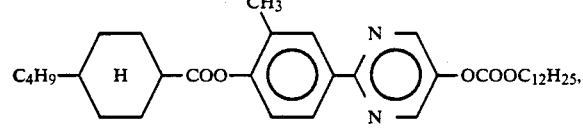 1-102
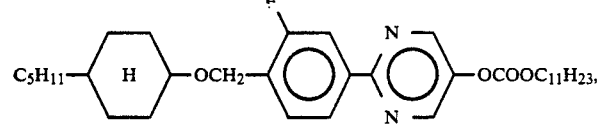 1-103
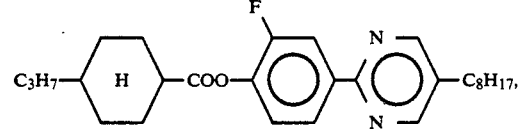 1-104
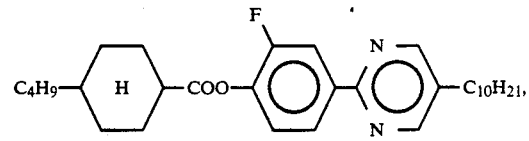 1-105

-continued
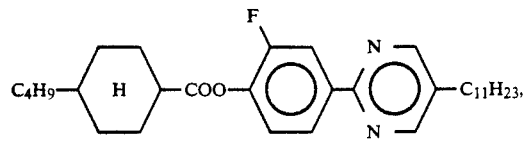 1-106
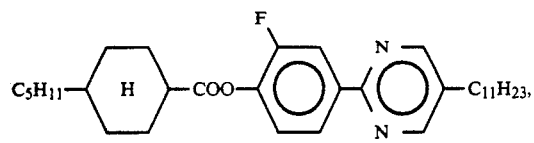 1-107
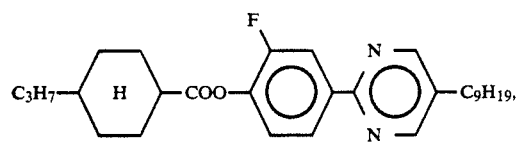 1-108
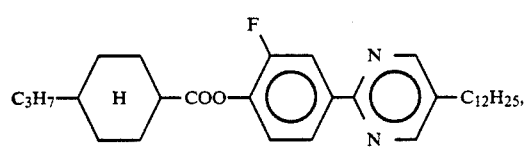 1-109
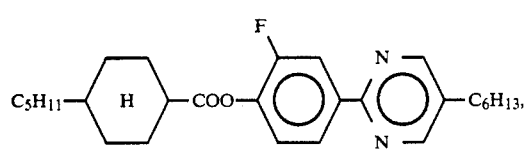 1-110
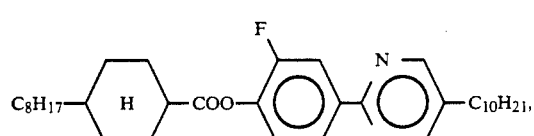 1-111
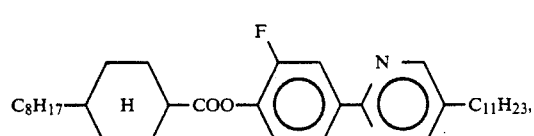 1-112
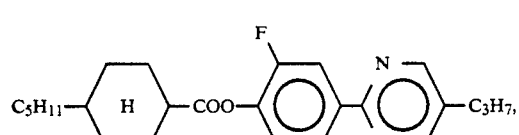 1-113
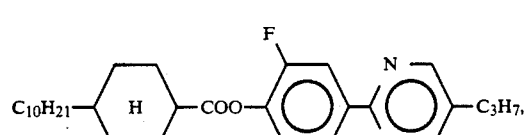 1-114
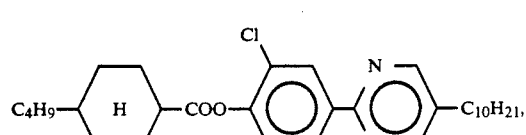 1-115
and 1-116

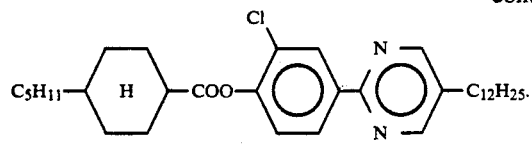

12. A liquid crystal device, comprising a pair of electrode plates and a liquid crystal composition according to claim 11 disposed between said electrode plates.

13. A liquid crystal composition according to claim 1, which comprises a third mesomorphic compound which is different from said formulae (I) and (II), said composition comprising 1-300 wt. parts each of a compound having said formula (I) and a compound having said formula (II) per 100 wt. parts of said third mesomorphic compound.

14. A liquid crystal composition according to claim 1, which comprises a third mesomorphic compound which is different from said formulae (I) and (II), one compound from each of said formulae (I) and (II) and at least one additional compound from at least one of formula (I) or formula (II), all said compounds of formulae (I) and (II) being present in a total amount of 1-500 wt. parts per 100 wt. parts of third mesomorphic compound which is different from said formulae (I) and (II).

15. A liquid crystal composition according to claim 1, which has a chiral smectic phase.

16. A liquid crystal device according to claim 4, which further comprises an alignment control layer on said electrode plates.

17. A liquid crystal device according to claim 16, wherein said alignment control layer has been subjected to rubbing.

18. A liquid crystal device according to claim 4, wherein said pair of electrode plates are disposed with a spacing therebetween sufficiently small to release the helical structure of the liquid crystal.

19. A liquid crystal composition according to claim 2, which comprises a third mesomorphic compound which is different from said formulae (I) and (III), said composition comprising 1-300 wt. parts each of a compound having said formula (I) and a compound having said formula (III) per 100 wt. parts of said third mesomorphic compound.

20. A liquid crystal composition according to claim 2, which comprises a third mesomorphic compound which is different from said formulae (I) and (III), one compound from each of said formulae (I) and (III) and at least one additional compound from at least one of formula (I) or formula (III), all said compounds of formulae (I) and (III) being present in a total amount of 1-500 wt. parts per 100 wt. parts of said third mesomorphic compound which is different from said formulae (I) and (III).

21. A liquid crystal composition according to claim 2, which has a chiral smectic phase.

22. A liquid crystal device according to claim 5, which further comprises an alignment control layer on said electrode plates.

23. A liquid crystal device according to claim 22, wherein said alignment control layer has been subjected to rubbing.

24. A liquid crystal device according to claim 5, wherein said pair of electrode plates are disposed with a spacing therebetween, sufficiently small to release the helical structure of the liquid crystal.

25. A liquid crystal composition according to claim 3, which comprises a third mesomorphic compound which is different from said formulae (I) and (II) and (III), said composition comprising 1-300 wt. parts each of a compound having said formula (II) and a compound having said formula (III) per 100 wt. parts of said third mesomorphic compound.

26. A liquid crystal composition according to claim 3, which comprises a third mesomorphic compound which is different from said formulae (I), (II) and (III), one compound from each of said formulae (I), (II) and (III) and at least one additional compound from at least one of formula (I), formula (II) or formula (III), all compounds of formulae (I), (II) and (III) being present in a total amount of 1-500 wt. parts per 100 wt. parts of said third mesomorphic compound which is different from said formulae (I), (II) and (III).

27. A liquid crystal composition according to claim 3, which has a chiral smectic phase.

28. A liquid crystal device according to claim 6, which further comprises an alignment control layer on said electrode plates.

29. A liquid crystal device according to claim 28, wherein the alignment control layer has been subjected to rubbing.

30. A liquid crystal device according to claim 6, wherein said pair of electrode plates are disposed with a spacing therebetween sufficiently small to release the helical structure of the liquid crystal.

* * * * *

UNITED STATES PATENT AND TRADEMARK OFFICE
CERTIFICATE OF CORRECTION

PATENT NO. : 5,250,219
DATED : October 5, 1993
INVENTOR(S) : SHOSEI MORI, ET AL.

It is certified that error appears in the above-identified patent and that said Letters Patent is hereby corrected as shown below:

COLUMN 1

Line 51, "so called" should read --so-called--.

COLUMN 2

Line 21, "U.S. Patent No. 4367924, instance," should read --U.S. Patent No. 4,367,924, etc.). In this instance,--.

COLUMN 3

Line 65, "linearn" should read --linear--.
Line 67, "$C_1-D_{12}$" should read --$C_1-C_{12}$--.

COLUMN 4

Line 17, "$-O(CH_2)_xO-CH_2-;$" should read -- $-O(CH_2)_kO-CH_2-;$ --.

COLUMN 5

Line 48, "the-above" should read --the above--.

COLUMN 6

Line 68, "(II-Viii)" should read --(II-viii)--.

COLUMN 19

Formula 1-48, " $\begin{array}{c} CH_3 \\ | \\ -(CH_2)_4CHOCH_3 \end{array}$ " should read -- $\begin{array}{c} CH_3 \\ | \\ O-(CH_2)_4CHOCH_3 \end{array}$ --.

UNITED STATES PATENT AND TRADEMARK OFFICE
CERTIFICATE OF CORRECTION

PATENT NO. : 5,250,219
DATED : October 5, 1993
INVENTOR(S) : SHOSEI MORI, ET AL.

It is certified that error appears in the above-identified patent and that said Letters Patent is hereby corrected as shown below:

COLUMN 25

Formula 1-83, "$OC_{12}H_{25}$," should read --$C_{12}H_{25}$--.

COLUMN 27

Formula 1-94, "$OCOC_{12}H_{24}$" should read --$OCOC_{12}H_{25}$--.

COLUMN 38

Formula (2-65) (second occurrence) at Line 40, "(2-65)" should read --(2-65A)--.

COLUMN 44

Line 14, "1090 980," should read --1090, 980,--.
Line 37, "1250 1160," should read --1250, 1160,--.
Line 42, "ture" should read --tural--.

COLUMN 45

Formula (3-13), "$C_{12}H_{25}$" should read --$C_{12}H_{25}$—O--.

COLUMN 55

Formula (3-74), "$C_{12}H_{25}$—25" should read --$C_{12}H_{25}$—O--.

COLUMN 89

Line 47, "molecules 23 so that the dipole" should be deleted.
Line 48, "moments ($P\perp$) 24 are all" should be deleted.

UNITED STATES PATENT AND TRADEMARK OFFICE
CERTIFICATE OF CORRECTION

PATENT NO. : 5,250,219
DATED : October 5, 1993
INVENTOR(S) : SHOSEI MORI, ET AL.

Page 3 of 5

It is certified that error appears in the above-identified patent and that said Letters Patent is hereby corrected as shown below:

COLUMN 92

Line 22, "compound A" should read --composition A--.

COLUMN 93

Line 25, "(film" should read --film--.
Line 31, "15 second" should read --15 seconds--.

COLUMN 100

Ex. Comp. No. 23, "$C_8H_{17}O$" should read --$C_8H_{17}$--.

COLUMN 101

Ex. Comp. No. 24, "$C_{11}H_{23}$" should read --$C_{11}H_{23}O$--.

COLUMN 107

Line 21, "switching" should read --clear switching--.

COLUMN 119

Line 37, "5" should be deleted.

COLUMN 120

Line 54, "2-65" should read --2-54--.
Line 55, "2-94" should read --3-94--.

COLUMN 122

Line 26, "2-67 3-69" should read --2-67, 3-69--.

UNITED STATES PATENT AND TRADEMARK OFFICE
CERTIFICATE OF CORRECTION

PATENT NO. : 5,250,219

DATED : October 5, 1993

INVENTOR(S) : SHOSEI MORI, ET AL.

It is certified that error appears in the above-identified patent and that said Letters Patent is hereby corrected as shown below:

COLUMN 144

Ex. Comp. No. 2-2, "$OH_{10}H_{21}$" should read --$OC_{10}H_{21}$--.

COLUMN 153

Line 65, "composition" should read --composition,--.

COLUMN 154

Line 23, "—COO," should read -- —COO—,--.
Line 39, "composition" should read --composition,--.
Line 65, "1-18," should read --1-18--.

COLUMN 155

Line 67, "pounds" should read --pound--.

COLUMN 156

Line 12, "bond" should read --bond,--.

COLUMN 171

Formula 1-86, "$C_5H_9$" should read --$C_5H_{11}$-- and
"$OC_8H_{17}$," should read --$OC_6H_{13}$,--.

COLUMN 193

Formula 1-83, "$C_{12}h_{25}$," should read --$C_{12}H_{25}$,--.
Formula 1-86, "$C_5H_9$" should read --$C_5H_{11}$-- and
"$OC_8H_{17}$," should read --$OC_6H_{13}$,--.

UNITED STATES PATENT AND TRADEMARK OFFICE
CERTIFICATE OF CORRECTION

PATENT NO. : 5,250,219
DATED : October 5, 1993
INVENTOR(S) : SHOSEI MORI, ET AL.

Page 5 of 5

It is certified that error appears in the above-identified patent and that said Letters Patent is hereby corrected as shown below:

COLUMN 213

Formula 1-83, "$C_{12}h_{25}$," should read --$C_{12}H_{25}$,--.

COLUMN 215

Formula 1-86, "$C_5H_9$" should read --$C_5H_{11}$-- and "$OC_8H_{17}$," should read --$OC_6H_{13}$,--.

COLUMN 221

Line 25, "third" should read --said third--.

COLUMN 222

Line 22, "therebetween," should read --therebetween which is--.

Signed and Sealed this

Twenty-sixth Day of July, 1994

Attest:

BRUCE LEHMAN

Attesting Officer  Commissioner of Patents and Trademarks